(12) United States Patent
Pollesello et al.

(10) Patent No.: US 6,774,103 B1
(45) Date of Patent: Aug. 10, 2004

(54) COMPOUNDS FOR DEACTIVATING PHOSPHOLAMBAN FUNCTION ON CA-ATPASE (PHOSPHOLAMBAN INHIBITORS)

(75) Inventors: Piero Pollesello, Grankulla (FI); Martti Ovaska, Espoo (FI); Jukka Tenhunen, Klaukkala (FI); Jukka Vidgren, Helsinki (FI); Marjo Yliperttula-Ikonen, Espoo (FI); Carola Tilgmann, Jorvas (FI); Timo Lotta, Vantaa (FI); Juha Kaivola, Helsinki (FI)

(73) Assignee: Orion Corporation, Espoo (FI)

( * ) Notice: Subject to any disclaimer, the term of this patent is extended or adjusted under 35 U.S.C. 154(b) by 0 days.

(21) Appl. No.: 09/722,440

(22) Filed: Nov. 28, 2000

Related U.S. Application Data

(60) Division of application No. 09/252,063, filed on Feb. 18, 1999, now Pat. No. 6,538,022, which is a continuation-in-part of application No. 08/937,117, filed on Sep. 24, 1997, now abandoned.

(51) Int. Cl.$^7$ .......................... A61K 38/00; C07K 7/00; C07K 14/00

(52) U.S. Cl. ............... 514/9; 514/12; 514/15; 530/324; 530/327; 530/334; 530/317; 324/307

(58) Field of Search ............... 514/9, 12, 15; 530/324, 327, 334, 317, 417; 324/307

(56) References Cited

U.S. PATENT DOCUMENTS

| | | | |
|---|---|---|---|
| 3,259,635 A | 7/1966 | Ritter et al. | 260/343.2 |
| 3,515,721 A | 6/1970 | Ritter et al. | 260/247.2 |
| 4,349,566 A | 9/1982 | della Valle | 424/281 |
| 4,452,811 A | 6/1984 | della Valle | 424/281 |
| 5,741,821 A | 4/1998 | Roufogalis et al. | 514/734 |

FOREIGN PATENT DOCUMENTS

WO     WO 94/28886     12/1994

OTHER PUBLICATIONS

Arkin, I.T., et al., "Structural Perspectives of Phospholamban, a Helical Transmembrane Pentamer," *Annu. Rev. Biophys. Biomol. Struct.* 26:157–179, Annual Reviews, Inc. (Sep. 1997).

Ferrari, B., et al., "Development of Tetrazole Bioisosteres in Angiotensin II Antagonists," *Bioorg. & Med. Chem. Lett.* 4(1):45–50, Pergamon Press (1994).

Havel, T.F., et al., "Effects of Distance Constraints on Macromolecular Conformation. II. Simulation of Experimental Results and Theoretical Predictions," *Biopolymers* 18:73–81, John Wiley & Sons, Inc. (1979).

Hoh, J.F.Y., "Muscle fiber types and function," *Curr. Opin. Rheum.* 4:801–808, Current Science (1992).

Karplus, M., "Vicinal Proton Coupling in Nuclear Magnetic Resonance," *J. Am. Chem. Soc.* 85:2870–2871, American Chemical Society (1963).

Kohara, Y., et al., "Synthesis and Angiotensin II Receptor Antagonistic Activities of Benzimidazole Derivatives Bearing Acidic Heterocycles as Novel Tetrazole Bioisosteres," *J. Med. Chem.* 39:5228–5235, American Chemical Society (Dec. 1996).

Koradi, R., et al., "MOLMOL: A program for display and analysis of macromolecular structures," *J. Mol. Graphics* 14:51–55, Elsevier Science Inc. (Feb. 1996).

McIntyre, L., and Freeman, R., "Accurate Measurement of Coupling Constants by J Doubling," *J. Mag. Res.* 96:424–431, Academic Press, Inc. (1992).

Stopar, D., et al., "Local Dynamics of the M13 Major Cost Protein in Different Membrane–Mimicking Systems," *Biochem.* 35:15467–15473, Chemical Society (Dec. 1996).

Wishart, D.S., et al., "The Chemical Shift Index: A Fast and Simple Method for the Assignment of Protein Secondary Structure through NMR Spectroscopy," *Biochem.* 31:1647–1651, American Chemical Society (1992).

STN Database CAPLUS, Document No. 94:15493, Joshi, B.S., et al., "Evaluation of some naturally occurring and synthetic coumarins for hypotensive activity," (1980).

STN Database CAPLUS, Document No. 77:88302, Murakami, M., et al., "Bis(carboxymethoxy)–4–methylcoumarins," (1972).

STN Database CAPLUS, Document No. 114:42491, Verma, B.S., et al., "Studies of pesticides based on coumarin: Part 5. Synthesis and antifungal activity of substituted 2,3–dihydrocyclopenta[c][1] benzopyran–4(H)–ones," (1989).

STN Database CAPLUS, Document No. 97:216033, Winter, W., et al., "Tricyclic aryl ethers and medicines containing these compounds," (1982).

STN Database CAPLUS, Document No. 97:216005, Lesher, G.Y., and Philion, R.E., "3–Substituted–6–(lower alkyl)–5–(pyridinyl)–2(1H)–pyridinones, their cardiotonic use and intermediates therefor," (1982).

(List continued on next page.)

Primary Examiner—Christopher S. F. Low
Assistant Examiner—Chih-Min Kam
(74) Attorney, Agent, or Firm—Sterne, Kessler, Goldstein & Fox PLLC

(57) ABSTRACT

This invention relates to determining the three-dimensional structure of the cytosolic domain of phospholamban (PLB) and its active site from NMR data of sufficiently high resolution for the three-dimensional structure determination. The invention also relates to methods for rational drug design enabling the design of phospholamban inhibitors based on using the three-dimensional structure data provided on computer readable media, as analyzed on a computer system having suitable computer algorithms. The invention also relates to phospholamban inhibiting compounds with certain structural, physicochemical and spatial characteristics that allow for the interaction of said compounds with specific residues of the active site of phospholamban.

16 Claims, 12 Drawing Sheets

OTHER PUBLICATIONS

STN Database CAPLUS, Document No. 84:179971, Bartl, K., et al., "Synthesis of .DELTA.8–tetrahydrodibenzo[b,d]pyran–6–ones and their aminolysis to .DELTA.8–tetrahydrophenanthridine–6–ones," (1976).

STN Database CAPLUS, Document No. 84:179968, Chebaane, K., et al., "Synthesis of 2–arylnaphthalenes and of dibenzocoumarins. I. Synthesis of tetrahydrodibenzocoumarins, 2–(1–cyclohexenyl)naphthalenes and tetrahydrobenzocoumarins," (1975).

Ferguson, D.G., et al., "Localization of Phospholamban in Smooth Muscle Using Immunogold Electron Microscopy," *J. Cell Biol.* 107:555–562 The Rockefeller University Press (1988).

Gao, Y., et al., "Interaction of calmodulin with phospholamban and caldesmon: comparative studies by $^1$H–NMR spectroscopy," *Biochim. Biophys. Acta* 1160:22–34, Elsevier Science Publishers B.V. (1992).

Lalli, J., et al., "Targeted Ablation of the Phospholamban Gene Is Associated With a Marked Decrease in Sensitivity in Aortic Smooth Muscle," *Circulation Res.* 80:506–513, American Heart Association, Inc. (Apr. 1997).

Lindemann, J.P., et al., "β–Adrenergic Stimulation of Phospholamban Phosphorylation and $Ca^{2+}$–ATPase Activity in Guinea Pig Ventricles," *J. Biol. Chem.* 258:464–471, American Society of Biological Chemists, Inc. (1983).

Liu, L.H., et al., "Defective Endothelium–dependent Relaxation of Vascular Smooth Muscle and Endothelial Cell $Ca^{2+}$ Signaling in Mice Lacking Sarco(endo)plasmic Reticulum $Ca^{2+}$–ATPase Isoform 3," *J. Biol. Chem.* 272:30538–30545, American Society for Biochemistry and Molecular Biology, Inc. (Nov. 1997).

O'Neil, K.T., and DeGrado, W.F., "How calmodulin binds its targets: sequence independent recognition of amphiphilic α–helices," *TIBS* 15:59–64, Elsevier Science Publishers Ltd. (UK) (1990).

Sutliff, R.L., et al., "Functional and Biochemical Evidence for Modulation of Endothelial Cell Function by Phospholamban," *FASEB J.* 12:A957, Abstract No. 5546, Federation of American Societies for Experimental Biology (1998).

Peters, R., and McKinstry, R.C., "Three–Dimensional Modeling and Drug Development," *Bio/Technology* 12:147, 149–150, Nature Publishing Company (1994).

Wanke, L.A., and DuBose, R.F., "Designer Drugs: The Evolving Science of Drug Discovery," *Practice Management Quarterly* 18:13–22, Aspen Publication (1998).

PHOSPHOLAMBAN SEQUENCES

```
                       1         10         20         30
Human               MEKVQYLTRS AIRRASTIEM PQQARQKLQN
Pig, dog            MDKVQYLTRS AIRRASTIEM PQQARQNLQN
Rabbit, rat, mouse  MEKVQYLTRS AIRRASTIEM PQQARQNLQN
Chicken             MEKVQYITRS ALRRASTLEV NPQARQRLQE 40         50
Human               LFINFCLILI CLLLICIIVM LL
Pig, dog            LFINFCLILI CLLLICIIVM LL
Rabbit, rat, mouse  LFINFCLILI CLLLICIIVM LL
Chicken             LFVNFCLILI CLLLICIIVM LL
```

COMPOUNDS FOR DEACTIVATING PHOSPHOLAMBAN FUNCTION ON CA-ATPASE (PHOSPHOLAMBAN INHIBITORS)

This application is a divisional of application Ser. No. 09/252,063, filed Feb. 18, 1999, now U.S. Pat. No. 6,538,022, which is a continuation-in-part of U.S. application Ser. No. 08/937,117, filed Sep. 24, 1997, now abandoned. The entirety of each of these applications is incorporated by reference herein.

FIELD OF THE INVENTION

The present invention relates to determining the three-dimensional structure of phospholamban (PLB) using NMR data of sufficiently high resolution for three dimensional structure determination. The invention also relates to methods for rational drug design enabling the design of compounds for deactivating phospholamban based on using the three-dimensional structure data provided on computer readable media, as analyzed on a computer system having suitable computer algorithms. The invention also relates to phospholamban deactivating compounds with structural, physicochemical and spacial characteristics that allow for the interaction of said compounds with specific residues of phospholamban. The interaction prevents the inhibiting effect of phospholamban on Ca-ATPase, making these compounds useful for treating diseases where the Ca-pumping activity of the Ca-ATPase may be diminished, such as congestive heart disease.

BACKGROUND OF THE INVENTION

Phospholamban (PLB) is a low molecular weight protein (52 amino acids), present in cardiac, slow-twitch and smooth muscle, which can be phosphorylated by both cAMP- and $Ca^{2+}$/calmodulin-dependent phosphokinases. The amino acid sequences of phospholamban from different species are shown in FIG. 1. The phosphorylation/ dephosphorylation of phospholamban has been shown to regulate the $Ca^{2+}$-ATPase of the sarco/endoplasmic reticulum in myocytes (SERCA_2). It has been shown that phospholamban, in its non-phosphorylated form, binds to a specific region of the large loop in the cytoplasmic domain of SERCA_2 and inhibits this pump by lowering its affinity for $Ca^{2+}$, while the phosphorylated form does not inhibit SERCA_2.

It has been proposed that a region essential for functional association of phospholamban with $Ca^{2+}$-ATPase lies in the cytoplasmic domain of phospholamban, while the transmembrane region anchors PLB to the sarcoplasmic membrane.

During the last decade, efforts have been made to elucidate, at least partially, the secondary structure of PLB either by means of cross-linking experiments or by reconstitution of SERCA_2 with point-mutated PLB, or, finally, by obtaining direct structural information by circular dichroism, laser light scattering photometry—FRTR spectroscopy and NMR spectroscopy). Molecular modelling has been used to formulate hypotheses on the quaternary structure of the transmembrane region in the PLB pentamer. The structural information obtained has been recently reviewed (Arkin, I. T. et al. (1997) Annu. Rev. Biophys. Biomol. Struct., 26, 157–179).

Since PLB i) is an amphiphatic oligopeptide, ii) contains three cysteines, and iii) is prone to pentamerization also in vitro, it is not straightforward to find good conditions to study its structure and, in particular, an appropriate solvent system which prevents unspecific aggregation. Therefore, until now NMR studies have been carried out either on short PLB fragments or in organic solvents. In no cases has evidence of a tertiary structure for the cytosolic domain of PLB been found.

Inhibition of CaATPases may play a causative role in cardiac disorders where the calcium levels of myocytes are high. As phospholamban inhibits SR CaATPase this inhibition may be harmful in such disorders. A compound capable of relieving the inhibitory effects of phospholamban on cardiac SR $Ca^{2+}$-ATPase, e.g. by interrupting phospholamban-$Ca^{2+}$-ATPase interaction, would be potentially useful in the treatment of such disorders. There have been very few examples on compounds which can prevent the inhibition of CaATPase by phospholamban in the literature. Such compounds include anti-phospholamban antibodies, some large polyanionic oligopeptides and tannins. No small molecules with specific interactions with phospholamban has been reported.

In the present invention it has been found that phospholamban can assume a well characterized conformation in which it can bind a broad series of small compounds with common structural, physicochemical and spacial characteristics that allow an interaction of the said compounds with specific residues of phospholamban in the defined conformation. This interaction deactivates phospholamban and prevents its inhibiting effect on Ca-ATPase. The phospholamban deactivating compounds are potentially useful in the treatment of cardiac disorders, where the activation of the SR CaATPase is beneficial.

SUMMARY OF THE INVENTION

The present invention is based on our complete resolution of the three-dimensional structure of the entire cytosolic domain of phospholamban and the ligand binding site therein.

In one aspect the present invention provides compounds capable of relieving the inhibitory effects of phospholamban on cardiac SR $Ca^{2+}$-ATPase, such compounds thus acting as phospholamban deactivators through direct binding to the phospholamban protein. These componds have common structural, physicochemical and spacial characteristics that allow for the interaction of said compounds with specific residues of the ligand binding site of phospholamban.

In another aspect the present invention provides a method of deactivating phospholamban which comprises administering to a mammal in need thereof a compound of the invention, as well as a pharmaceutical preparation comprising a compound of the invention together with a pharmaceutically acceptable carrier.

In another aspect, the present invention provides methods for rational drug design enabling the design of phospholamban deactivators based on using the three-dimensional structure data of phospholamban cytosolic domain provided on computer readable media, as analyzed on a computer system having suitable computer algorithms.

In still another aspect, the present invention provides the three-dimensional structure of phospholamban cytosolic domain provided on computer readable media.

Other aspects of the present invention will be apparent to one of ordinary skill in the art from the following detailed description and examples relating to the present invention.

BRIEF DESCRIPTION OF THE FIGURES

FIG. 1 shows the amino acid sequences of phospholamban from different species (human (SEQ ID NO: 1), pig (SEQ ID NO: 2), dog (SEQ ID NO: 3), rabbit (SEQ ID NO: 4), rat (SEQ ID NO: 5), mouse (SEQ ID NO: 6), chicken (SEQ ID NO: 7)).

DETAILED DESCRIPTION OF THE INVENTION

Figure 2:
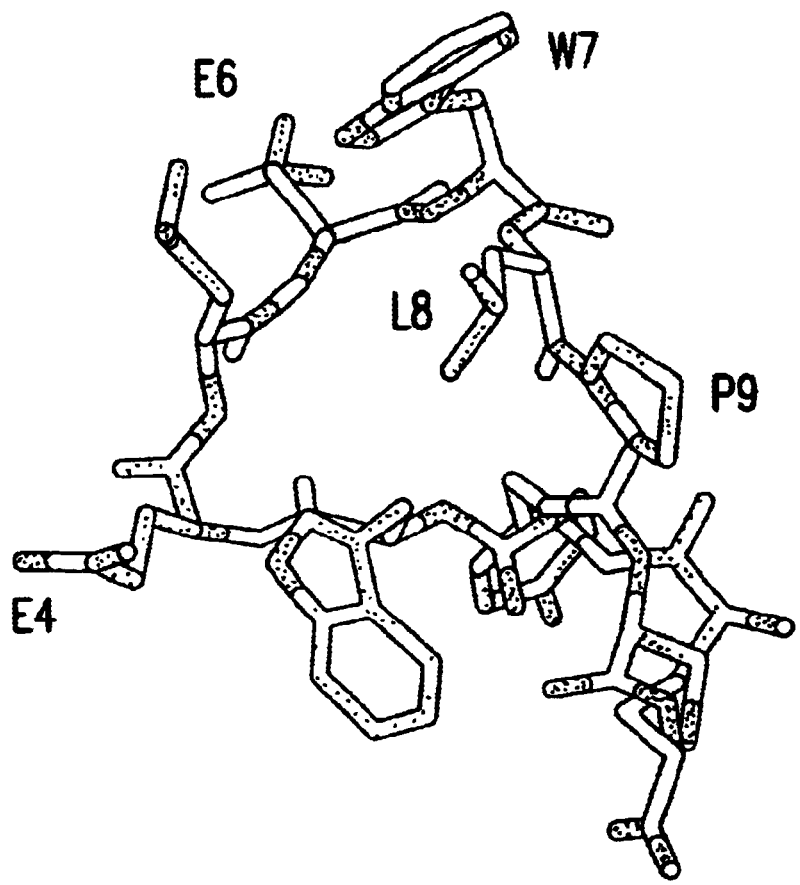
FIG. 2 is an illustration of the NMR structure of the cyclic peptide cP226 (SEQ ID NO: 10).

Structure of phospholamban (1–36) (SEQ ID NO:9)

The present invention is based on our complete resolution of the three-dimensional structure of the entire cytosolic domain of phospholamban (PLB) and the ligand binding site therein. It was possible to determine the structure of the phospholamban cytosolic domain using a method of NMR spectroscopy wherein the NMR data is of sufficiently high resolution for the three-dimensional structure determination. The method comprises providing the 1–36 a.a. fragment of phospholamban, which comprises the cytosolic domain and 6 amino acids of the transmembrane domain, for the NMR analysis in aqueous solution containing 30% trifluoroethanol. The three-dimensional structure can then be determined from the NMR data by distance geometry followed by simulated annealing. The method is described in detail in EXAMPLE 1.

It was found that phospholamban (1–36) (SEQ ID NO:9) fragment assumes a conformation characteristic of a helix-turn-helix motif. The residues of the turn are Ile18, Glu19, Met20, and Pro21, which are adjacent to the two phosphorylation sites Ser16 and Thr17. The proline is in a trans conformation. Both helices have predominantly charged and polar residues on one side, whereas the other is lipophilic. The hydrophilic side of the N-terminal helix faces always the lipophilic side of the C-terminal helix defining a pocket which could be described as an amphipathic armpit. This may mean that in order to interact with SERCA_2, PLB should assume a prolonged position (i.e. the axes of two α-helices should be nearly parallel), while in the bent conformation those charges would not be exposed to the ATPase but eventually to the surface charges of the phospholipid bilayer. The loose relative positioning of the two helices around the mobile central hinge domain is thus a functional feature of PLB. This flexibility may explain also why, in organic solvent, PLB can assume a prolonged structure.

The structure also reveal that the pocket between the hydrophilic side of the N-terminal helix and the lipophilic side of the C-terminal (defined as an amphipathic armpit) is an ideal target for small amphipathic drug molecules designed with the purpose of deactivating PLB by stabilizing its bent conformation. Such molecules would relieve the inhibitory effect of phospholamban on cardiac SR $Ca^{2+}$-ATPase, and therefore act as a PLB deactivator through direct binding to the active site of PLB.

Structure of cP226 (SEQ ID NO: 10)

In order to find a lead molecule which would interact with PLB a series of peptides were screened. It was found that a cyclic peptide of formula (pI) (SEQ ID NO: 8) was able to bind to PLB and activate the calcium intake in liposomes containing both SERCA_2 and PLB while being inactive in liposomes lacking PLB. It was concluded that the cyclic peptide of formula (pI) binds to unphosphorylated PLB and prevents the inhibition exerted by PLB on SERCA_2 thus acting as a PLB deactivator. The cyclic peptide (pI) has the structure:

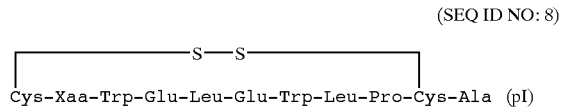

(SEQ ID NO: 8)

Xaa is preferably Tyr or Ala.

The cyclic peptide of formula (pl) wherein X is Tyr was named cP226 (SEQ ID NO: 10). In order to determine the ligand binding site of PLB, the tertiary structure of the cP226 (SEQ ID NO: 10) was resolved by NMR spectroscopy. The method used is described in detail in EXAMPLE 2. The three-dimensional structure of cP226 (SEQ ID NO: 10) show bend-coil-bend motif. The lipophilic side chains of Trp-3, Leu-5, Trp-7 and Leu-8 are clustered on one side of the cyclic peptide, leaving the most of the polar carbonyl and amine groups of the backbone on the other side. The three dimensional coordinates of the cyclic peptide cP226 (SEQ ID NO: 10) are provided in Table I annexed to the present application.

Structure of the complex cP226•PLB(1–36)

On the basis of the resolved tertiary structures of PLB(1–36) (SEQ ID NO: 9) and its ligand cP226 (SEQ ID NO: 10) it was possible to prepare a model of the complex cP226•PLB(1–36) by molecular modelling. The three-dimensional model describes the interactions between PLB(1–36) (SEQ ID NO: 9) and its ligand which are important in binding of ligands to the cytosolic domain of PLB.

The NMR-solved structures of PLB(1–361 (SEQ ID NO: 9) and cP226 (SEQ ID NO: 10) were used as templates for the building of the complex. cP226 (SEQ ID NO: 10) was docked interactively with help of molecular graphics and guided by possible interactions between the two peptides. The structure of cP226 (SEQ ID NO: 10) shows that the peptide has two negative side chains (Glu4 and Glu-6) on one side while the other side is hydrophobic (Trp-7, Leu-8, Pro-9) (FIG. 2). In PLB(1–36) (SEQ ID NO: 9) there is a cluster of three positive side chains (Arg-9, Arg-13, Arg-14) opposed by a mainly hydrophobic surface of the C-terminal helix (e.g. Leu-28, Leu-31, Phe-32, Phe-35) (FIG. 3). cP226 (SEQ ID NO: 10) was manually docked onto PLB(1–36) (SEQ ID NO: 9) so that Glu4 and Glu-6 come to contact with Arg-9, Arg-13 and Arg-14, while at the same time Trp-7, Leu-8 and Pro-9 are near the hydrophobic surface of PLB C-terminal helix. This gave the starting point for an energy refinement of the complex.

The energy of the obtained complex was minimized by InsightII using the general valence force field (gvff93). Rough minimization was made by the steepest descents method, followed by conjugate gradients and the Newton method.

Figure 4:
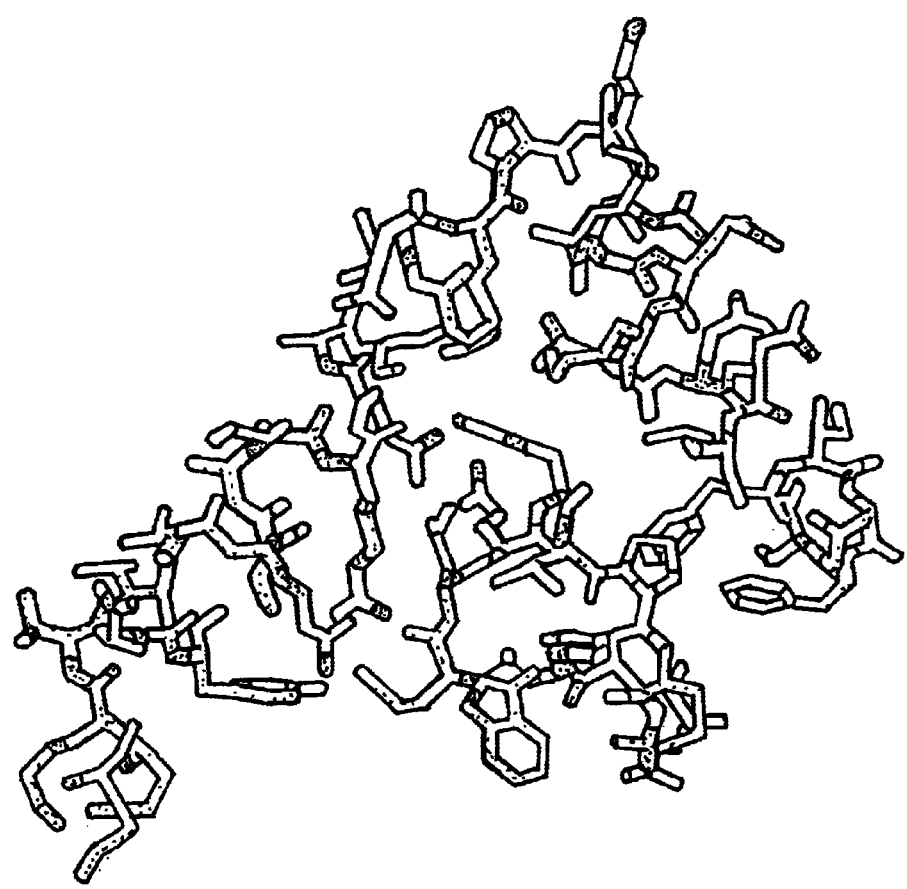
FIG. 4 is an illustration of the model structure of the complex between PLB(1–36) (SEQ ID NO: 9) and cyclic peptide cP226 (SEQ ID NO: 10).

The structure of the energy minimized complex cP226•PLB(1–36) is shown in FIG. 4. The final total energy of the complex was 113 kcal/mol (non-bond dispersion energy –1574 kcal/mol, coulomb energy –690 kcal/mol).

Figure 5:
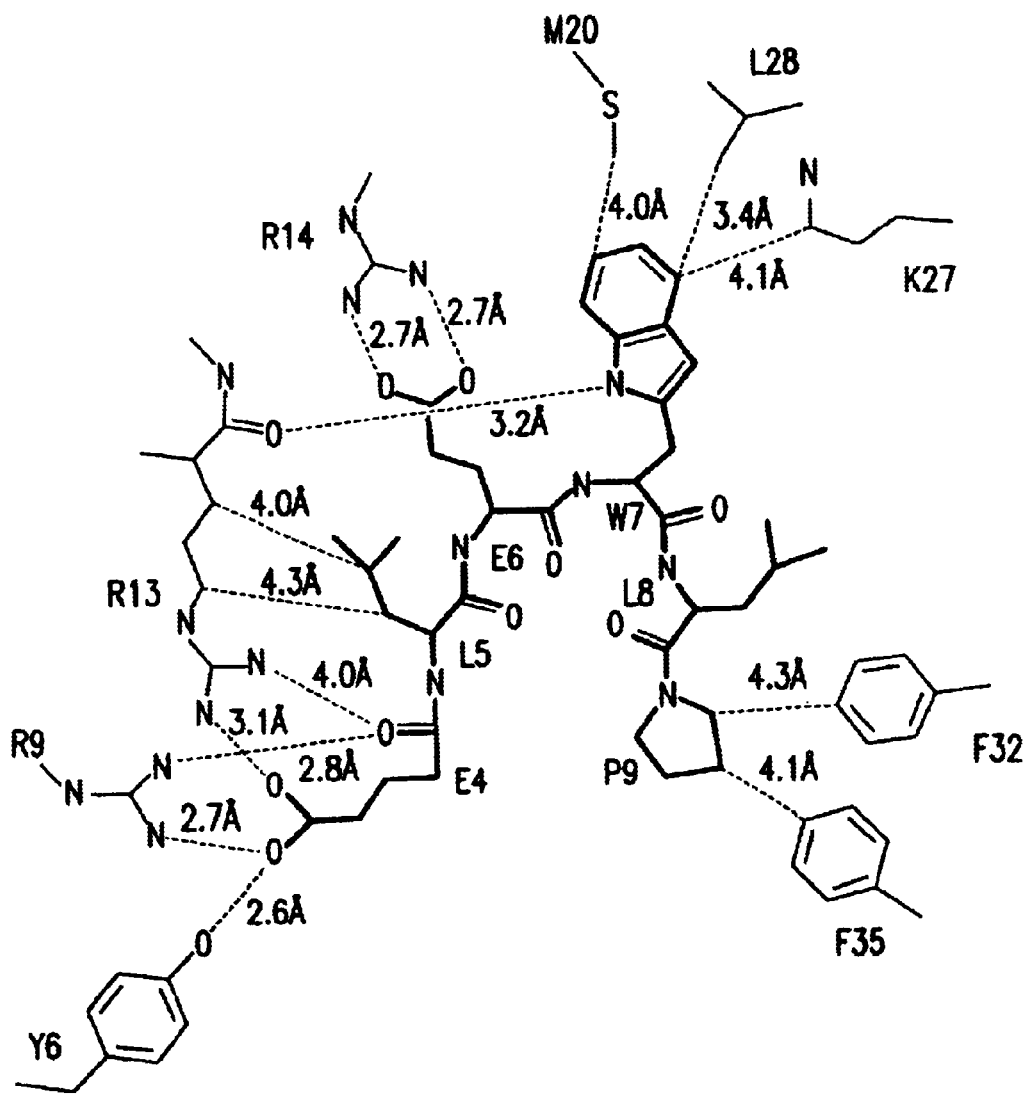
FIG. 5 is an illustration of the main interactions of cP226 (SEQ ID NO: 10) with PLB(1–36) (SEQ ID NO: 9) in the model of the binary complex. The distances between the heavy atoms capable for electrostatic binding, H-bonding, or hydrophobic interactions are shown.
Figure 6:
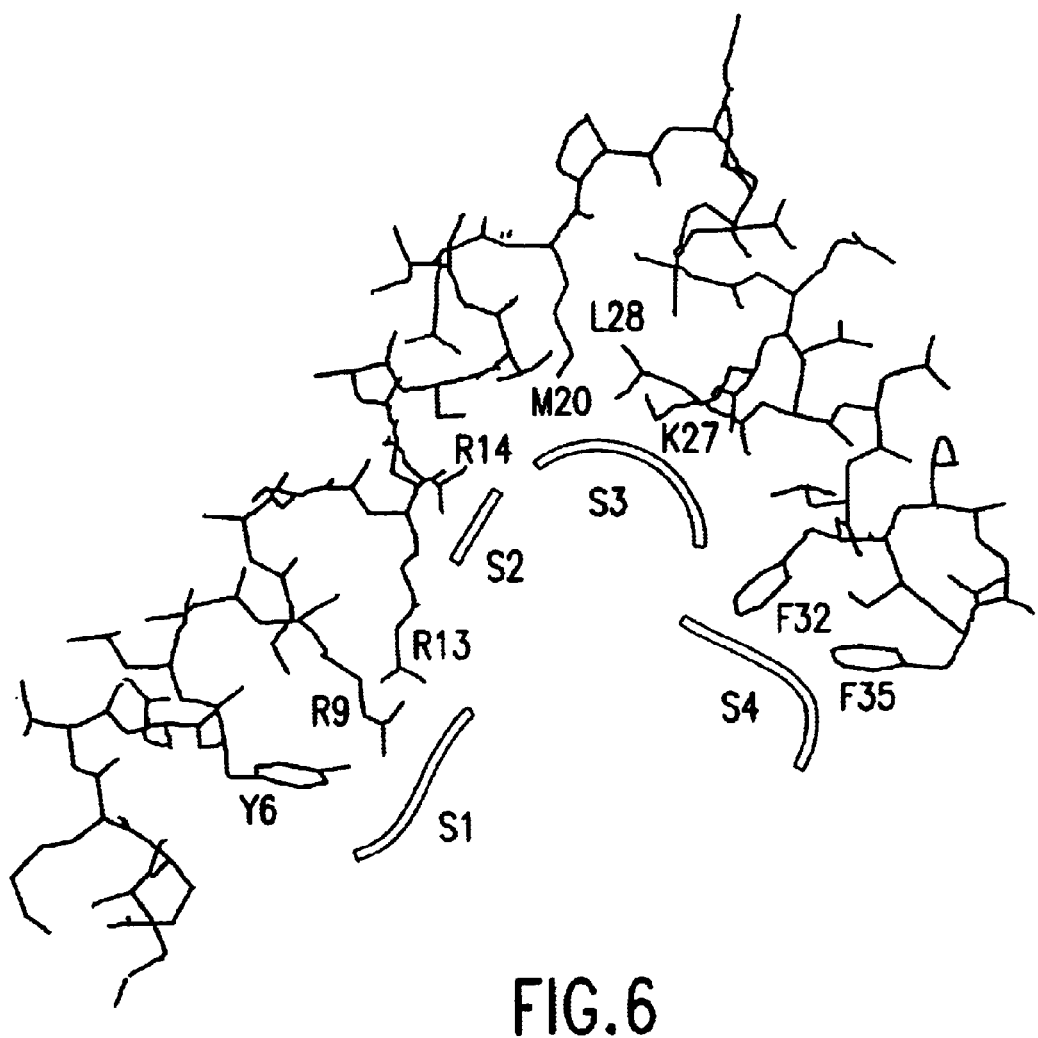
FIG. 6 is an illustration showing the PLB amino acid side chains which form the binding site for ligands, divided to four interactions sites denoted as S1–S4.

A schematic sketch of the binding mode of cP226 (SEQ ID NO: 10) to PLB is shown in FIG. 5. The binding can be described by four binding sites (S1–S4) which bind Glu4, Glu-6, Trp-7 and Pro-9, respectively (Table 11, FIG. 6). Glu-4 has electrostatic/H-bonding interactions with Tyr-6, Arg-9 and Arg-13 (S1), Glu-6 binds to Arg-14 (S2), Trp-7 is buried in a hydrophobic pocket (S3) formed mainly by Met-20, Lys-27 and Leu-28 and Pro-9 binds to a hydrophobic cleft (S4) formed mainly by Phe-32 and Phe-35. Besides, Leu-5 is lined by the hydrophobic part of the side chain of Arg-13 and NH of the indole of Trp-7 can form an H-bond to the carbonyl of Arg-13. The positive N-terminal amino group (NH3+) is near the hydrophobic binding site S4.

TABLE II

Binding of cP226 (SEQ ID NO: 10) to PLB

| Site | PLB | cP226 (SEQ ID NO: 10) |
| --- | --- | --- |
| S1 | Tyr-6, Arg-9, Arg-13 | Glu-4 |
| S2 | Arg-14 | Glu-6 |
| S3 | Met-20, Lys-27, Leu-28 | Trp-7 |
| S4 | Phe-32, Phe-35 | Pro-9 |

Thus, the term "binding site S1" is defined as the space surrounded by amino acid residues Tyr-6, Arg-9 and/or Arg-13, particularly —OH group of Tyr-6, guanidinium group of Arg-9 and/or guanidinium group of Arg-13.

The term "binding site S2" is defined as the space surrounded by amino acid residue Arg-14, particularly guanidinium group of Arg-14.

The term "binding site S3" is defined as the space surrounded by amino acid residues Met-20, Lys-27 and/or Leu 28, particularly the side chains thereof.

The term "binding site S4" is defined as the space surrounded by amino acid residues Phe-32 and/or Phe-35, particularly the phenyl groups thereof.

Figure 8:
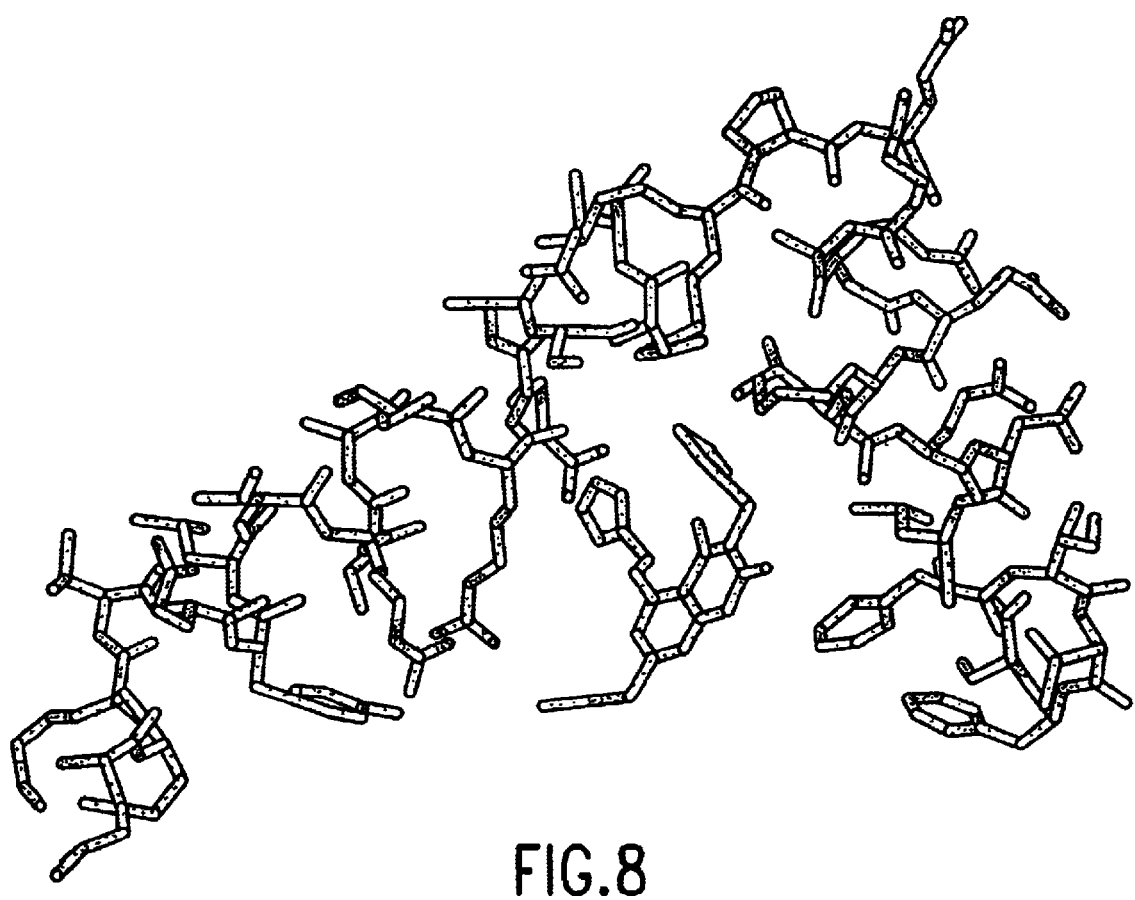
FIG. 8 is an illustration of the superposition of compound of Example 1c onto the PLB structure.

The three dimensional atom coordinates of phospholamban (1–36) (SEQ ID NO:9) in a conformation which allows binding of cyclic peptide cP226 (SEQ ID NO: 10) are disclosed in Table III annexed to the present application. The three dimensional atom coordinates of the complex between phospholamban (1–36) (SEQ ID NO:9) and the cyclic peptide cP226 (SEQ ID NO: 10) are disclosed in Table IV annexed to the present application. FIG. 8 is an illustration of the superposition of one compound of the invention (compound of Example 1c) onto the PLB structure.

Rational Drug Design

Structure determination methods are also provided by the present invention for rational drug design (RDD) of PLB ligands. Such drug design uses computer modeling programs that calculate different molecules expected to interact with the determined binding sites or other structural or functional domains of PLB. These molecules can then be produced and screened for activity in deactivating PLB according to methods of the present invention.

The present invention reveals the ligand binding site of PLB cytosolic domain heretofor unknown and comprises a distinct three dimensional arrangement of atoms. The atom coordinates of PLB (1–36) (SEQ ID NO: 9) in a conformation which allows binding of a PLB deactivator of the invention to the PLB cytosolic domain are disclosed in Table III. This structure for the first time enables the structure-based design of highly active PLB deactivators. The structure of PLB cytosolic domain provided herein permits the screening of known molecules or designing of new molecules which bind to the ligand binding site of PLB cytosolic domain, via the use of computerized evaluation systems. For example, computer modeling systems are available in which the atomic coordinates of PLB cytosolic domain and the ligand binding site thereof as provided in Table III can be used as input. Thus, a computer readable medium may be encoded with data representing the coordinates of Table HI in this process.

The present invention provides a method for identifying a PLB deactivator comprising the steps of:
i) providing atom coordinates of the structure of PLB cytosolic domain or portion thereof in a computerized modeling system, ii) identifying compounds which are capable of interacting with said structure, and iii) testing the compounds identified or analogs derived therefrom for the activation of CaATPase in the presence of phospholamban.

In particular, the present invention provides a method for identifying a PLB deactivator comprising the steps of:
i) providing the atom coordinates of the structure of PLB cytosolic domain or portion thereof in a computerized modeling system, ii) identifying compounds which are capable of interacting with at least three of the binding sites S1, S2, S3 and S4 of the PLB cytosolic domain, and iii) testing the compounds identified or analogs derived therefrom for the activation of CaATPase in the presence of phospholamban.

In particular, the present invention provides a method for identifying a PLB deactivator comprising the steps of:
i) providing atom coordinates of the structure of PLB cytosolic domain or portion thereof in a conformation which allows binding of a PLB deactivator to PLB cytosolic domain, in a computerized modeling system, ii) identifying compounds which are capable of said interaction iii) testing the compounds identified or analogs derived therefrom for the activation of CaATPase in the presence of phospholamban.

In the method of the invention candidate molecules may be obtained by carrying out computer-aided molecular design using the three-dimensional structure of the PLB cytosolic domain particularly when complexed with a PLB inhibitor, and in particular the three-dimensional structure at and/or around the binding sites S1 to S4, and synthesising the molecules so-designed.

In the method of the invention candidate molecules can be tested for their ability to deactivate phospholamban, for example, using assays which are described in detail in EXAMPLE 3 or modification thereof.

The invention also provides a computer readable medium having stored therein atom coordinates of the structure of the PLB cytosolic domain or portion thereof in a conformation which allows binding of a PLB deactivator to the PLB cytosolic domain.

As used herein, "computer readable media" refers to any medium which can be read and accessed directly by a computer. Such media include, but are not limited to: magnetic storage media, such as floppy discs, hard disc storage medium, and magnetic tape; optical storage media-such as optical discs or CD-ROM; electrical storage media such as RAM and ROM; and hybrids of these categories such as magnetic/optical storage media. A skilled artisan can readily appreciate how any of the presently known computer readable media can be used to create a manufacture comprising computer readable medium having stored therein atom coordinates of the structure of the PLB. The choice of the data storage structure will generally be based on the means chosen to access the stored information. Variety of data processor programs and formats can be used to store the atom coordinate data of the present invention on the computer readable medium.

By providing computer readable media having stored therein atom coordinate data of the structure of the PLB, a skilled artisan can routinely access the atom cordinate data of the structure of the PLB cytosolic domain or portion thereof. Computer algorithms are publicly and commercially available which allow a skilled artisan to access this data provided on a computer readable medium and analyze it for structure determination and/or rational drug design. See, e.g. Biotechnology Software Directory, Mary Ann Liebert Publ., New York (1995).

Structural atom coordinates of the PLB (1–36) (SEQ ID NO: 9) presented in Table m may be stored in a computer readable form on a computer readable storage medium for display as a three-dimensional shape or for other uses involving computer-assisted manipulation of the structural coordinates they define. For example, data defining the three dimensional structure of a PLB cytosolic domain or portions thereof may be stored in a computer readable storage medium, and may be displayed as a graphical three-dimensional representation of the protein structure, typically using a computer capable of reading data from said storage medium and programmed with instructions for creating the representation from such data. The invention thus encompasses a machine, such as a computer, having memory which contains data representing the structural coordinates of the PLB protein of the invention, e.g. coordinates presented in Table III, together additional optonal data and instructions for manipulating such data. Such data can be used for a variety of purposes, such as the rational drug design. The invention encompasses the coordinates of Table III as well as any translation or rotation or the like thereof which maintains the internal coordinates, i.e. which maintains their intrinsic, internal relationship. Those skilled in the art will appreciate that the coordinates may be subjected to other transformations including, e.g. molecular mechanics calculations such as dynamic simulation, minimization, etc. For example, a first set of computer readable data defining the three-dimensional structure of PLB cytosolic domain or a portion thereof is combined with a second set of computer readable data defining the structure of a candidate molecule using a computer programmed with instructions for evaluating the ability of the candidate molecule to associate PLB cytosolic domain protein and/or the location and/or orientation of such association.

The protein structure encoded by the data may be displayed in a graphical format permitting visual inspection of the structure, as well as visual inspection of the structures association with candidate molecules. Alternatively, more quantitative of computational methods may be used. For example, one method of this invention for evaluating the ability of a candidate molecule to associate with PLB cytosolic domain comprises the steps of i) employing computational means to perform a fitting operation between the candidate molecule and the binding sites of PLB, and ii) analyzing the results of said fitting operation to quantify the association between the candidate molecule and the binding sites of PLB.

One method of this invention provides for selecting from a database of chemical structures a compound capable of binding to PLB cytosolic domain. The method starts with structural coordinates defining the three dimensional structure of PLB cytosolic domain or portion thereof. Binding sites of that three dimensional structure are characterized with respect of the favorability of interactions with one or more functional groups. A database of chemical structures is then searched for candidate compounds containing functional groups disposed for favorable interaction with the PLB based on the prior characterization. Compounds having structures which best fit the points of favorable interaction with three dimensional structure are thus identified.

Computer programs for viewing three dimensional structures or manipulating atom coordinates are available and well known for one skilled in the art.

Phospholamban Deactivating Compounds

The invention provides phospholamban deactivating compounds being capable of associating with any three of the binding sites S1, S2, S3 and S4 of the PLB cytosolic domain. In particular, the invention provides a phospholamban deactivating compound comprising at least any three of the following:

(a) a first electronegative moiety being capable of associating with the S1 binding site of the PLB cytosolic domain when the deactivator is bound thereto said binding site comprising Tyr-6, Arg-9 and/or Arg-13, (b) a second electronegative moiety being capable of associating with the S2 binding site of the PLB cytosolic domain when the deactivator is bound thereto said binding site comprising Arg-14, and (c) a first hydrophobic moiety being capable of associating with the S3 binding site of the PLB cytosolic domain when the deactivator is bound thereto said binding site comprising Met-20, Lys-27 and/or Leu-28.

(d) a second hydrophobic moiety being capable of associating with the S4 binding site of the PLB cytosolic domain when the deactivator is bound thereto said binding site comprising Phe-32 and/or Phe-35.

In particular, the invention provides a phospholamban deactivating compound comprising at least any three of the following:

(a) a first electronegative moiety being capable of forming a hydrogen bond with the—OH group of Tyr-6, a salt bridge with the guanidinium group of Arg-9 and/or a salt bridge with the guanidinium group of Arg-13, of the PLB cytosolic domain when the deactivator is bound thereto, (b) a second electronegative moiety being capable of forming a salt bridge with the guanidinium group of Arg-14, of the PLB cytosolic domain when the deactivator is bound thereto, (c) a first hydrophobic moiety being capable of associating with a hydrophobic pocket created by Met-20, Lys-27 and/or Leu-28, of the PLB cytosolic domain when the deactivator is bound thereto and.

(d) a second hydrophobic moiety being capable of associating with a hydrophobic pocket created by Phe-32 and/or Phe-35, of the PLB cytosolic domain when the deactivator is bound thereto.

In particular, the invention provides a phospholamban deactivating compound comprising:

(a) a first electronegative moiety being capable of forming a hydrogen bond with the—OH group of Tyr-6, a salt bridge with the guanidinium group of Arg-9 and/or a salt bridge with the guanidinium group of Arg-13, of the PLB cytosolic domain when the deactivator is bound thereto,
(b) a second electronegative moiety being capable of forming a salt bridge with the guanidinium group of Arg-14, of the PLB cytosolic domain when the deactivator is bound thereto and
(c) a first hydrophobic moiety being capable of associating with a hydrophobic pocket created by Met-20, Lys-27 and/or Leu-28, of the PLB cytosolic domain when the deactivator is bound thereto and.

Therefore, for a phospholamban deactivator of to the invention, at least three of the first electronegative moiety of (a), the second electronegative moiety of (b), the first hydrophobic moiety of (c) and the second hydrophobic moiety of (d) are capable of forming said hydrogen bond and/or salt bridges of (a), said salt bridge of (b), said associations with the hydrophobic pocket of (c), and said associations with the hydrophobic pocket of (d), respectively, with said groups or hydrophobic pockets of PLB, at the same time.

Phospholamban deactivating compounds of the invention include, but are not limited to, compounds of formula (I) or (II):

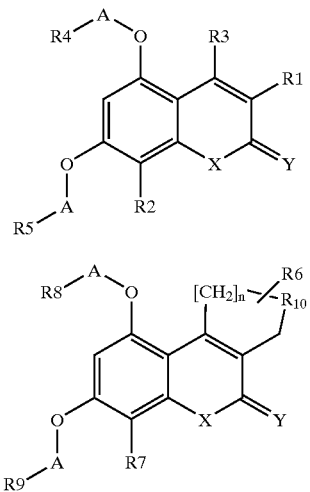

in which $R_1$ is hydrogen, alkyl, alkenyl, aryl, arylalkyl, hydroxyalkyl, halogenalkyl, alkoxy, $COR_{10}$, $CONR_{10}R_{11}$, $OR_{10}$, $S(O)_m R_{10}$, $NR_{10}COR_{11}$ or $NR_{10}R_{11}$, where $R_{10}$ is hydrogen, alkyl, alkenyl, aryl, arylalkyl, hydroxyalkyl, halogenalkyl, alkoxy or hydroxy and $R_{11}$ is hydrogen, alkyl, aryl, arylalkyl, alkoxy, aryloxy, hydroxy or acyl, or in case where X is $NR_{11}$, can $R_1$ also be carboxylalkyl, $R_6$ is hydrogen, alkyl, alkenyl, aryl, arylalkyl, $R_2$ and $R_7$ mean hydrogen, alkyl, aryl, arylalkyl, alkenyl, $COR_{10}$, $CONR_{10}R_{11}$, halogen, trifluoromethyl, nitro or cyano, where $R_{10}$ and $R_{11}$ are defined as above, $R_3$ is hydrogen, alkyl, aryl or arylalkyl, A means alkyl or substituted alkyl, m is 0–2 and n is 1–3, Y means O, $NR_{11}$ or S, where R11 is the same as above, X means O, $NR_{11}$ or S, where R11 is the same as above, $R_4$, $R_5$, $R_8$ and $R_9$ mean independently one of the following groups:

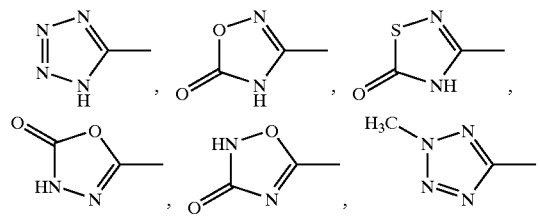

or in case where X is $NR_{11}$, can $R_4$, $R_5$, $R_8$ and $R_9$ also independently mean HOOC—, $R_{12}$OOC—, $H_2$NCO— or HOHNCO— wherein $R_{12}$ means alkyl, arylalkyl or aryl, and wherein each aryl residue defined above by itself or as part of another group may be substituted, and pharmaceutically acceptable salts and esters thereof. The compounds of formula (I) or (II) share the structural features which allow them to associate with the ligand binding site of PLB cytosolic domain thereby relieving the the inhibitory effects of PLB on cardiac SR $Ca^{2+}$-ATPase.

Compounds of formula (I) or (II) can be prepared from the 1,3-dihydroxy substituted heteroaromatics by alkylation of the dihydroxy compounds by suitable alkylating agents, for example by chloroacetonitrile or bromoacetic ester according to the following Scheme 1, wherein $R_1$, $R_2$, $R_3$, X and Y are the same as defined above, R' is a protecting group for the hydroxyl, e.g. methyl, benzyl or tetrahydropyranyl.

SCHEME 1

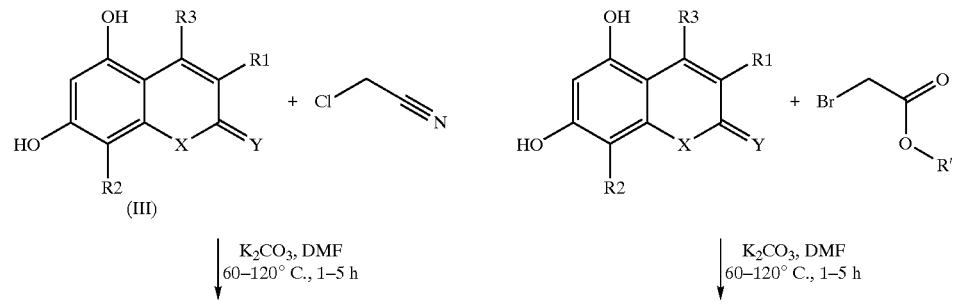

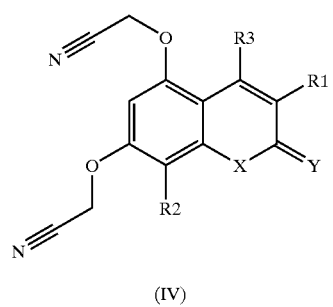
(IV)
NAN₃, NH₄Cl, DMF
80–120° C., 1–3 h
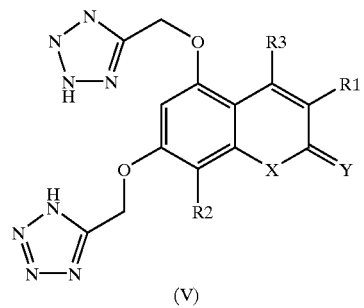
(V)
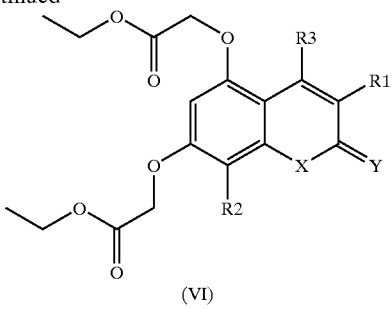
(VI)
NaOH or HCl
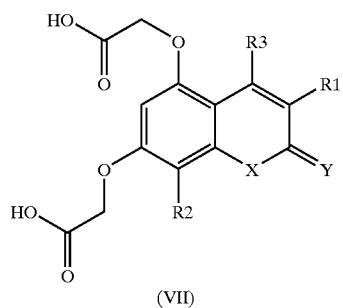
(VII)
The cyano compound (IV) described above is used to prepare the 1,2,4-oxadiazole and 1,2,4-thiadiazole derivatives using the methods described in Kohara et al. (1996) J. Med. Chem., 39, 5228–5235.
The syntheses are shown in Scheme 2, wherein $R_1$, $R_2$, $R_3$, X and Y are the same as defined above.
SCHEME 2
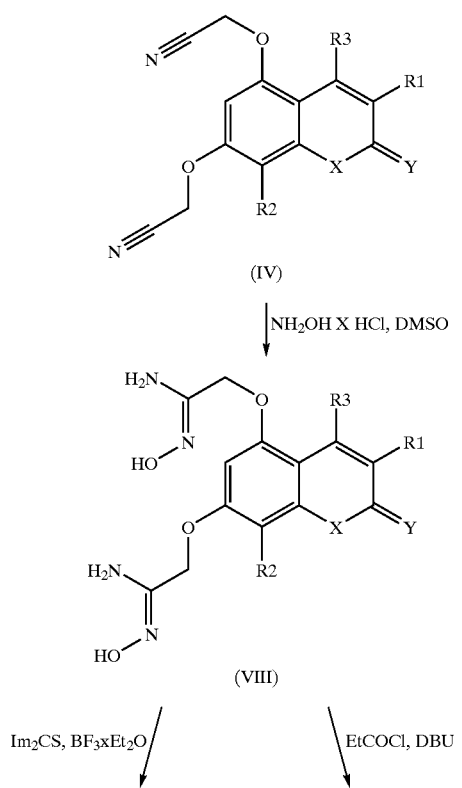

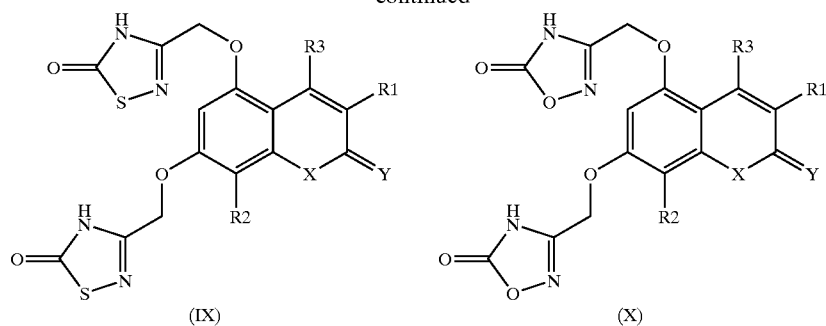

(IX) (X)

The other heterocyclics as groups $R_4$, $R_5$, $R_8$ and $R_9$ are prepared as described in Feffari, B. et al. (1994) Bioorg. Med. Chem. Lett., 4, 45–50.

The dihydroxyaromatics (III) are made by use of the literature methods. The coumarins (XIV), (XVI) and (XX) are made by the use of the Knoevenagel condensation or von Pechmann reaction as presented in Scheme 3 and 4, where $R_1$, $R_2$ and $R_3$, are the same as defined above, Z is alkyl, aryl, arylalkyl or alkenyl and R' is a protecting group for the hydroxyls e.g. methyl, benzyl or tetrahydropyranyl.

SCHEME 3

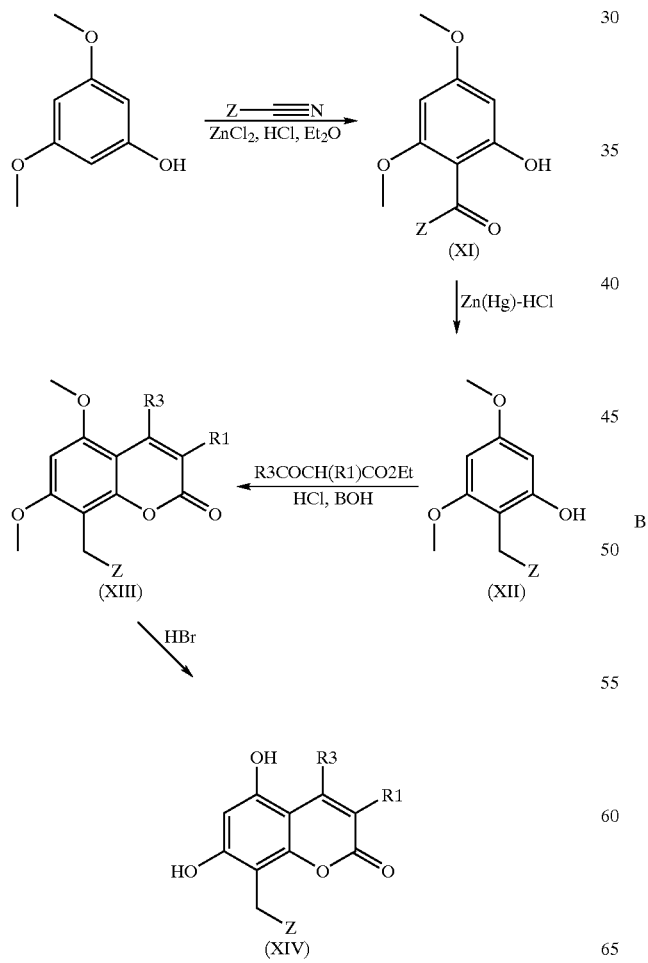

SCHEME 4

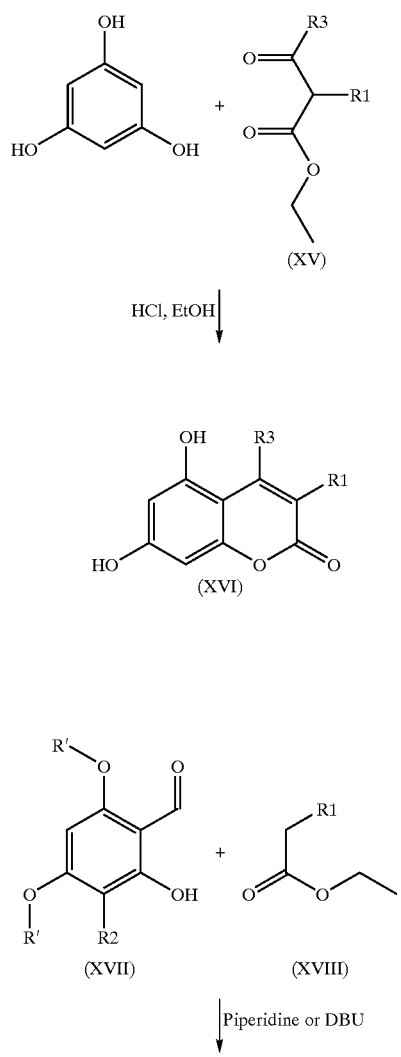

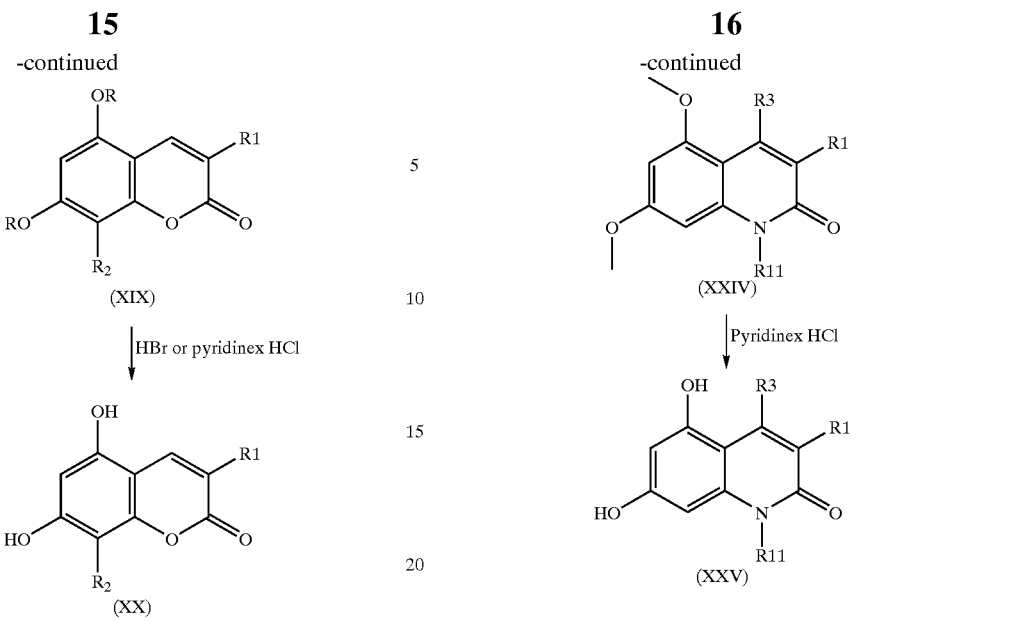

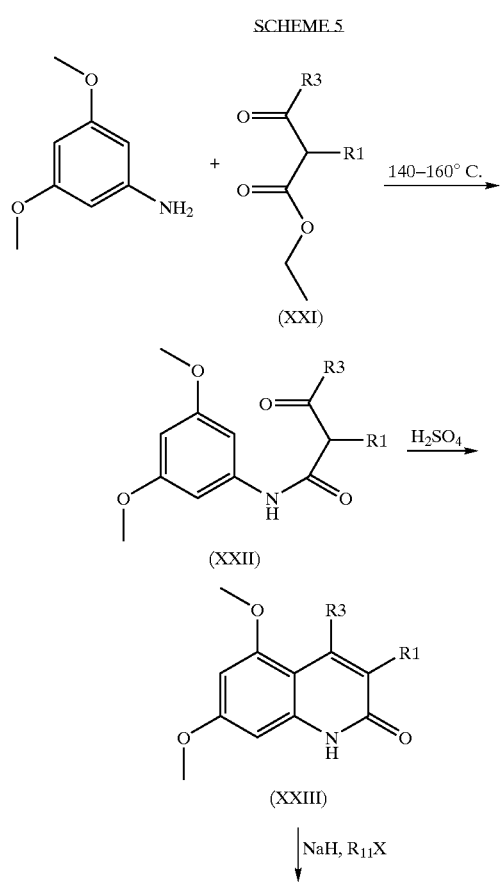

The quinolinones are prepared by the Knorr reaction as described in Scheme 5, wherein $R_1, R_{11}$ and $R_3$ are the same as defined above, X is a halogen.

The cyclic compounds (II) can be prepared correspondingly from compound (XXXI) which can be prepared according to the Scheme 6, wherein $R_2$ and $R_6$ are the same as defined above, R' is a protecting group for the hydroxyls e.g. methyl, benzyl or tetrahydropyranyl.

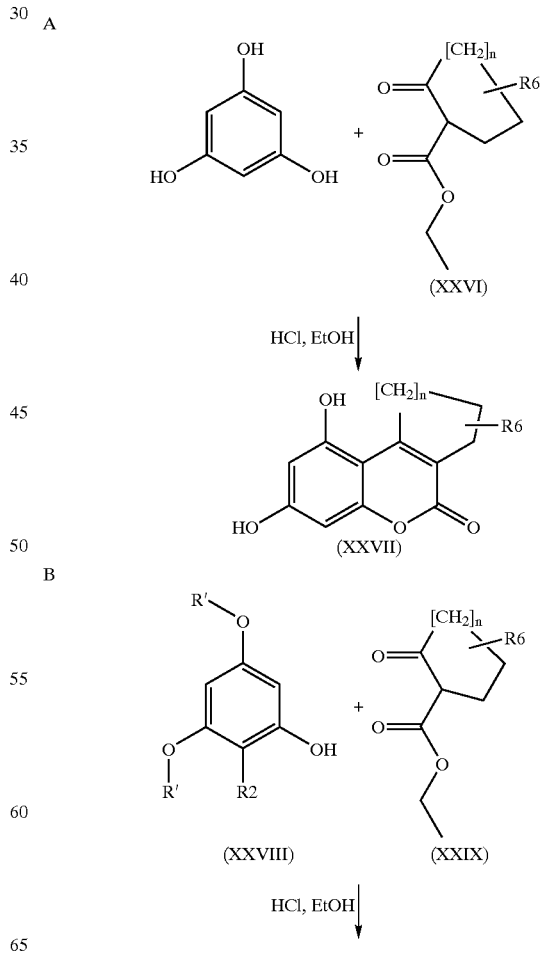

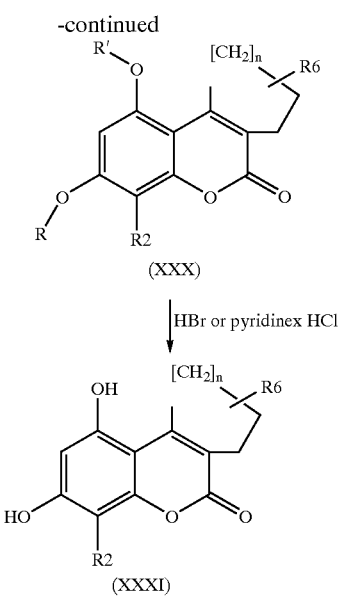

Cyclic quinolinone compounds (II) can be prepared correspondingly from (XXVI) using Scheme 5.

Salts and esters of the compounds, when applicable, may be prepared by known methods. Physiologically acceptable salts are useful as active medicaments, however, preferred are the salts with alkali or alkaline earth metals. Physiologically acceptable esters are also useful as active medicaments. Examples are the esters with aliphatic or aromatic alcohols.

The term "alkyl" as employed herein by itself or as part of another group includes both straight and branched chain radicals of up to 18 carbon atoms, preferably 1 to 8 carbon atoms, most preferably 1 to 4 carbon atoms. The term "lower alkyl" as employed herein by itself or as part of another group includes both straight and branched chain radicals of 1 to 7, preferably 1 to 4, most preferably 1 or 2 carbon atoms. Specific examples for the alkyl and lower alkyl residues, respectively, are methyl, ethyl, propyl, isopropyl, butyl, tert. butyl, pentyl, hexyl, octyl, decyl and dodecyl including the various branched chain isomers thereof.

The term "acyl" as employed herein by itself or as part of another group refers to an alkylcarbonyl or alkenylcarbonyl group, the alkyl and alkenyl groups being defined above.

The term "aryl" as used herein by itself or as part of another group refers to a monocyclic or bicyclic group containing from 6 to 10 carbon atoms in the ring portion. Specific examples for aryl groups are phenyl, naphtyl and the like. "Aroyl" means in a corresponding way an arylcarbonyl group.

The term "alkoxy" as employed herein by itself or as part of another group includes an alkyl group as defined above linked to an oxygen atom. "Aryloxy" means in a corresponding way an aryl group linked to an oxygen atom.

The term "substituted" as used herein in connection with various residues refers to halogen substituents, such as fluorine, chlorine, bromine, iodine or trifluoromethyl group, amino, alkyl, alkoxy, aryl, alkyl-aryl, halogen-aryl, cycloalkyl, alkylcycloalkyl, hydroxy, alkylamino, alkanoylamino, arylcarbonylamino, nitro, cyano; thiol, or alkylthio substituents.

The "substituted" groups may contain 1 to 3, preferably 1 or 2, most preferably 1 of the above mentioned substituents.

Compound of the invention may be administered to a patient in therapeutically effective amounts which range usually from about 0.1 to 500 mg per day depending on the age, weight, condition of the patient, administration route and the phospholamban deactivator used. The compounds of the invention can be formulated into dosage forms using the principles known in the art. It can be given to a patient as such or in combination with suitable pharmaceutical excipients in the form of tablets, dragees, capsules, suppositories, emulsions, suspensions or solutions. Choosing suitable ingredients for the composition is a routine for those of ordinary skill in the art. It is evident that suitable carriers, solvents, gel forming ingredients, dispersion forming ingredients, antioxidants, colours, sweeteners, wetting compounds and other ingredients normally used in this field of technology may be also used. The compositions containing the active compound can be given enterally or parenterally, the oral route being the preferred way. The contents of the active compound in the composition is from about 0.5 to 100 %, preferably from about 0.5 to about 20 %, per weight of the total composition.

The following Examples serve purely as an illustration of the various aspects of this invention, and is not intended to be limiting the present invention.

EXAMPLE 1

Structure of the Cytosolic Domain of Phospholamban

Phospholamban (1–36) (SEQ ID NO: 9) synthesis, purification and characterization The cytosolic part of phospholamban peptide having the amino acid sequence MEKVQYLTRSAIRRASTI-EMPQQARQKLQNLFINFC (SEQ IN NO: 9) was synthesized with an automated peptide synthesizer (Perkin-Elmer, Applied Biosystems 431A) using the fluorenylmethoxycarbonyl strategy. The synthesis was started from the hydrophobic C-terminal end. The side chain protecting groups employed during the synthesis were: Trityl (Trt) for Asn, Gln, and Cys, tert-Butoxy (OtBu) for Glu, tert-Butyl (tBu) for Ser, Thr and Tyr, tert-Butoxycarbonyl (Boc) for Lys and 2,2,5,7,8-Pentamethyl chroman-6-sulphonyl (Pmc) for Arg. The amount of the preloaded resin was 100 μmol and the quantity of the amino acids at each step of the synthesis was 1 mmol. This is a 10 times excess as compared to the amount of the resin loaded.

The peptide cleavage from the resin support (originally preloaded Wang resin) was performed in methylene chloride containing 5% TFA, 0.2% B-mercaptoethanol, 0.2% thio anisole and 0.2% dimethylsulfide. Cleavage of the side chain protection of the peptide was carried out in a mixture of ethanedithiol:thioanisole:water:trifluoroaceticacid=250 μl: 500 μl: 500 μl: 10 ml for 1.5 hours at room temperature. After that the peptide was precipitated and washed three times with diethylether, and lyophilized.

The synthesized crude phospholamban (1–36) (SEQ IN NO: 9) peptide was prepurified by high performance liquid chromatography (HPLC) technique with an analytical reversed phase (RP) column ($C_8$, 20 μm, 4.6 mm×30 mm i.d. Perkin-Elmer, Applied Biosystems Brownlee TM column). A linear gradient of acetonitrile (0–100% in 30 min.) in 0.1% TFA was used for elution.

The repurified peptide was futher purified by HPLC RP-chromatography using a $C_{18}$ Kromasil, 5 μm (1.0×25 cm) column. The peptide was eluted using a stepwise gradient of acetonitrile, 0.075% TFA (3–30%, in 10 min, 30–50% in 120 min.) in 0.1% TFA.

The purified phospholamban (1–36) peptide (SEQ IN NO: 9) was characterized by SDS-PAGE followed by Coomassie brilliant blue staining. Western blot analysis was done by using the commercial monoclonal anti-PLB antibody (Upstate Biotechnology). The purified RP-chromatography peaks containing the peptide was further analyzed by mass spectrometry (MALDI-TOF) in reflector mode with a BIFLEX™ mass spectrometer using a 337 nm nitrogen laser. The samples were applied in a solution containing 30% acetonitrile/0.1% TFA together with a droplet of sinapinic acid matrix for mass spectrometry analysis. The total amount of purified protein was estimated according to Bradford and also based on RP-chromatography using β-lactoglobulin as a standard reference. The purified peptides were lyophilized and the dry powder was estimated by weight before analysis of the 3-dimensional structure.

Obtaining NMR Spectra of Phospholamban (1–36) (SEQ IN NO: 9)

$^1$HNMR spectra were acquired at 400.13 MHz and at 599.86 MHz on a Bruker ARX400 and a Varian UNITY 600 NMR spectrometer respectively. 1D and 2D NMR spectra were obtained for a 3 mM solution of the 36-a.a. fragment of PLB in the solvent mixture $H_2O:D_2O:d_3$-TFE (63:7:30) containing 6 mM $d_{10}$-DTT to prevent disulphide formation. The pH was adjusted to 3.00±0.02 (uncorrected for deuterium isotope effects) with microliter amounts of NaOD. COSY, TOCSY (30–90 ms) and NOESY (40–400 ms) spectra were recorded at 2, 7, 17 and 27° C., by the States-TPPI method using a spectral width of 8.5 ppm. The 2D data was weighted and Fourier transformed to 2 k×1 k real point matrices. The transmitter presaturated (2.0 s) residual solvent line was reduced by deconvolution. The spectra were referenced to the residual solvent signal (4.75 ppm at 27° C., –10 ppb/° C.). A series of ten ID spectra was acquired at different temperatures (ranging from 2 to 47° C.).

Assignment of the NMR Spectra of Phospholamban (1–36) (SEQ ID NO:9)

The spin-system and sequential assignments were derived according to Wüthrich, K. et al. (1986) NMR of Proteins and Nucleic Acids, John Wiley & Sons, Inc., New York, by use of COSY, TOCSY and NOESY spectra acquired at 12, 17 and 27° C. Differences in the temperature dependences of the amido proton chemical shifts were sufficient to unravel resonance overlap. Stereospecific assignments for non-degenerated methylenes were deduced from coupling constants $J_{H\alpha H\beta}$ measured from the COSY spectra and from intra residual NOE-cross peak intensities.

Phospholamban (1–36) (SEQ ID NO:9) Structure Generation and Refinement

A series of NOESY spectra was acquired at 17° C. with five different mixing times (50, 80, 120, 160, and 200 ms). The integrated cross peak intensities (1) were used in a NOESY-built-up-analysis. Distance restraints were extracted from the inital slope of a second-order polynomial curve fitted to the volumes of the cross peaks integrated from the NOE-series, with the initial condition $I_{(\tau m=0)}=0$. Intra methylene and sequential NOEs served for the calibration. The distances were initially classified as short (1.8–2.5 Å), medium (1.8–3.5 Å) or long (3.0–6.0 Å) for the generation of the first set of structures. When a distance could not be calculated from the built-up curve, owing to a partial (>20%) overlap, a poor signal-to-noise ratio or disturbances, it was only required that the distance was <5.0 Å. The upper bounds were extended by 1.0 Å for each pseudo atom. The restraint data were supplemented with distance restraints, which were based on strong, medium and weak NOEs, from the 150 ms NOE-spectrum acquired at 12° C.

Coupling constants (J) were measured by the J-doubling method (McIntyre, L. et al. (1992) J Magn Reson 96, 425–431) from fine structures of COSY cross peaks.

Dihedrals φ and χ, which were characterised by intermediate J, were not constrained but small and large $J_{NH\alpha}$ and $J_{H\alpha H\beta}$ were related to staggered conformers (±30 degrees) on the basis of Karplus functions and intra residual NOEs (Karplus, M. (1963) J. Am. Chem. Soc., 85, 2870). The H—H distance and dihedral angle restraints were calculated and the data were imported into the software InsightII (Molecular Simulations, Inc.) in order to generate, evaluate and refine the structures. Simulated NOESY spectra were back calculated. The protein coordinate files were analysed by the software PROMOTIF v2.0 (Hutchinson, G. (1995), v2.0 Ed., available by anonymous ftp on 128.40.46.11).

Structures were generated by distance geometry (DGII) followed by simulated annealing (force field AMBER) (Havel, T. et al. (1979) Biopolymers 18, 73). A set of structures was computed. The structures with the least restraint violations were used to back calculate NOE-matrices. If the Hα-chemical shift of consequent residues in the segment characterised by NOEs typical of α-helices departed from the corresponding random coil value more than –0.2 ppm, also the correspondent dihedrals ψ were constrained (±60 degrees). A new set of structures was subsequently calculated. From this new family of structures only those structures with no violations over 0.2 Å were accepted.

Assignment Results

The complete spin-system and sequential assignments were obtained under the experimental conditions described. The assignments are listed in Table V (annexed to the present application) showing H-chemical shifts of PLB (1–36) (SEQ ID NO:9) in 54% $H_2O$/6% $D_2O$/30% $d_3$-TFE, pH 3.05 at 17° C., wherein the staggered conformations are denoted by a line under the chemical shift of $C_\beta H$ in an anti-configuration and by a dashed line in a gauche-configuration (–60 degree) to $C_\alpha H$.

Figure 7:
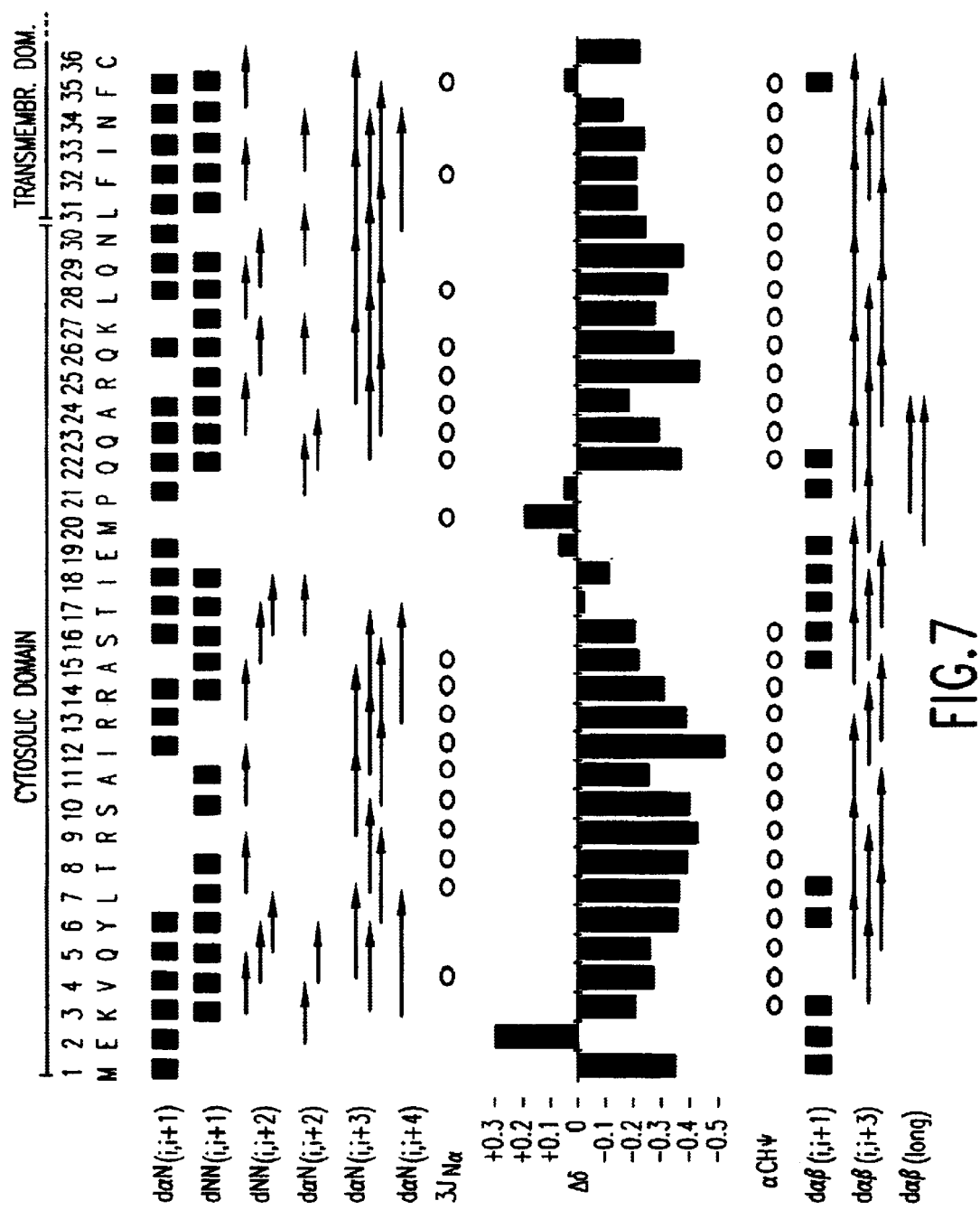
FIG. 7 is the summary of the observed sequential and medium-range NOE connectivities for PLB(1–36) (SEQ ID NO: 9).

FIG. 7 is a summary of the observed sequential and medium-range NOE connectivities for PLB(1–36) (SEQ ID NO: 9) in 54% $H_2O$/6% $D_2O$/30% $d_3$-TFE, at pH 3.05 at 17° C., wherein assignments were made from NOESY spectra acquired at 120, 160 and 200 ms mixing times. Sequential NOEs are represented by shaded blocks. Medium-range NOEs are represented by arrows connecting the appropriate residues. Open circles denote $^3J_{NH\alpha CH}$ coupling constants smaller than 7 Hz. The secondary shift (Δδ) of αCH is defined as the difference between the observed chemical shift and the random coil chemical shift for each residue. Negative (upfield) Δδ values are associated with α-helical secondary structure and positive (downfield) Δδ values with β-structure according to Wishart et al., Biochemistry (1992), 31, 1647–1651.

In total 723 NOEs were assigned. All the 34 possible intra NH—$C_\alpha$H correlations were observed in the finger print region. Most of the corresponding NOEs were fairly strong and comparable to sequential $NH_{i+1}$-$C_\alpha H_i$ NOEs (FIG. 7). Many sequential $NH_i$-$NH_{i+1}$ and $NH_i$—$NH_{i+2}$ NOEs were present. Numerous $C_\alpha H_i$—$NH_{i+3}$ and some $C_\alpha H_i$—$NH_{i+4}$ NOEs were crowded in the finger print region of the NOESY spectra. Furthermore, there were a number of $C_\alpha H_i$—$C_\beta H_{i+3}$ cross peaks. NOEs derived from interactions longer than i>i+4 were observed only for protons of Met20.

J-couplings between NH and $C_\alpha$H were small for most residues. Due to overlap of resonances or weak intenstity of COSY cross peaks it was not possible to measure accurate values for all residues but the couplings were below 7–8 Hz with the exception of the residues at the N- and C-terminus and in the center of PLB (1–36) (SEQ ID NO: 9).

The central region of the PLB(1–36) (SEQ ID NO: 9) does not show a helical character. Namely, the $\delta_{C\alpha H}$ values of the residues Glu19, Met20 and Pro21 were not significantly smaller than their random coil values. Glu19 and Met20 were mostly devoid of the NOEs typical of a helical structure, and there were unambiguous strong sequential NOEs between $C_\alpha H$ of Glu19 and NH of Met20, and between $C_\alpha H$ of Met20 and $C_\delta Hs$ of Pro21. Furthermore, the NOE between $C_\alpha H$ of Ile18 and NH of Glu19 is strong, even when partially buried in the crowded finger print region. All this implies that the central region of PLB(1–36) (SEQ ID NO: 9) assumes an extended-like conformation. The extended segment is, nevertheless, short. Thr17 and Gln22 show NOEs and coupling constants characteristic of residues in an α-helix, and there are NOEs from the side chain protons of Glu19 and Met20 to the protons of the adjacent residues in the N- and C-terminal helices. We conclude that the N- and C-terminal α-helices are separated by a turn at Ile18, Glu19, Met20, and Pro21. The proline is in a trans-conformation. A tight turn, which would result the axes of the N- and C-terminal helices being parallel, is not possible. There were no unambiguous NOEs between the N- and C-terminal helices.

Structure of PLB (1–36) (SEQ ID NO: 9)

The structure of PLB (1–36) (SEQ ID NO: 9) was determined from 599 distances and 50 dihedral restraints excluding those that were defined more accurately by the covalent structure alone. These redundant NOE-derived restraints were consistent with the covalently imposed distance limits, which indicated that the calibration of distances was reasonable. On average there were 16.6 non-trivial NOE-derived restraints per residue. The residues Lys3-Ile18 of the N-terminal helix had on average a few restraints less per residue than the residues Gln22-Cys36 in the C-terminal helix. This is at least partly due to the fact that there were on average more protons with non-degenerated shifts per residue in the C-terminal helix than in the N-terminal helix (Table V). For the residues Ile18-Pro21, which confine the turn, there were about as many restraints per residue as there were for the residues in the N-terminal helix.

Figure 9:
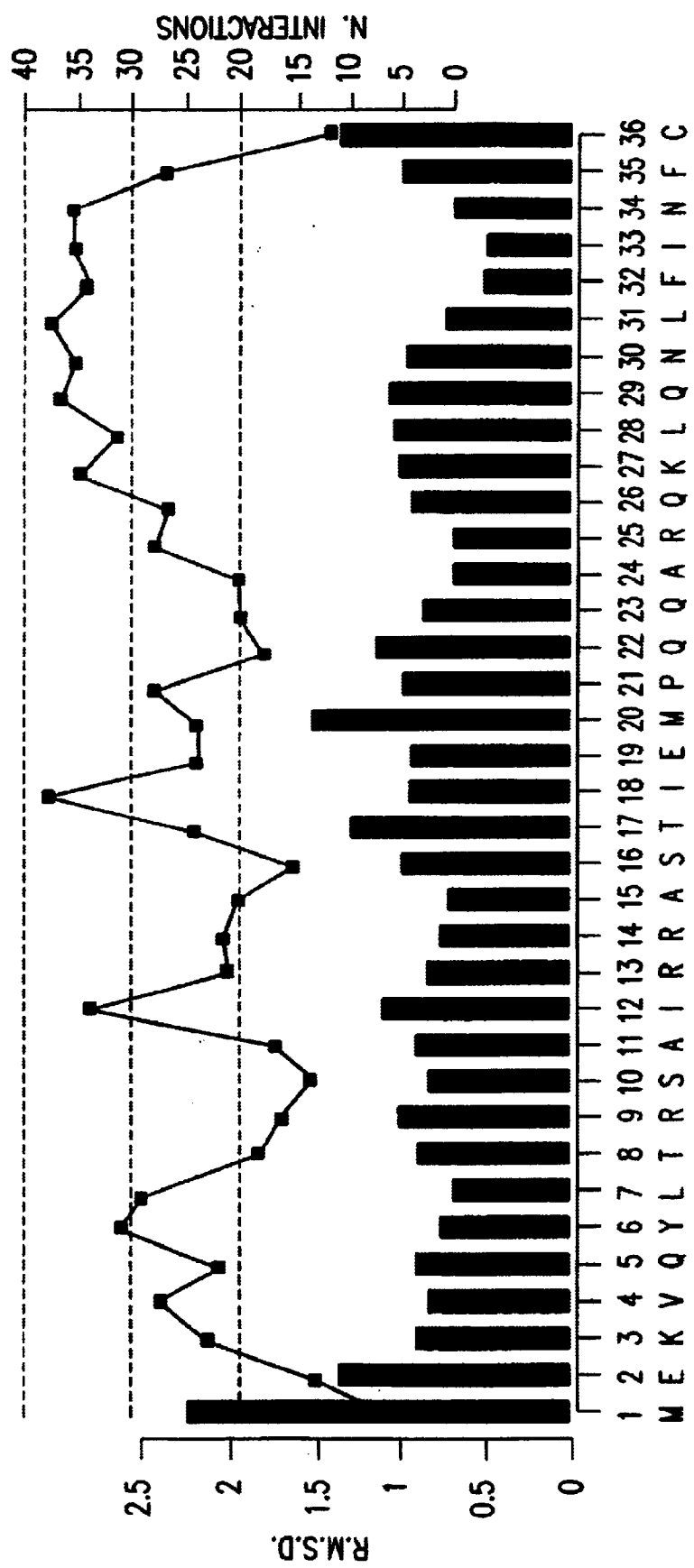
FIG. 9 shows the quality of the structure of PLB(1–36) (SEQ ID NO: 9) obtained by NOE data. RMSD per residue and the number of restraints per residue is shown.

The structure generation resulted in a family of structures all of which show a helix-turn-helix motif. The root mean square deviation was computed from the family of 20 structures with no distance violations above 0.2 Å and no dihedral violations. FIG. 9 shows the quality of the structure of PLB(1–36) (SEQ ID NO: 9) obtained by NOE data wherein RMSD per residue and the number of restraints per residue is shown.

Since no unambiguous long range NOEs were found between the N- and C-terminal helices, the family of structures displayed a dispersion of atomic coordinates in the remote parts of the N- and C-terminal helices. The mutual orientation of the helices was constrained only by the short range distance restraints in the turn. Therefore, RMSD per residue was computed separately i) for the N-terminal helix plus the turn (a.a. 1–21) and ii) for the C-terminal helix plus the turn (18–36). The RMSD represented roughly an inverse correlation with the number of restraints per residue, as expected. In average the atoms in the N-terminal helix were defined to a precision of 1.3 Å (backbone only) and of 2.3 Å (all atoms) and in the C-terminal helix to a precision of 0.8 Å (backbone only) and of 1.9 Å (all atoms). The smallest number of distance violations (below 0.2 Å) were observed for structures in which the segment from Cα of Glu19 to Cα of Pro21 is extended, the side chain of Met20 sticks out approximately parallel to the C-terminal helix and the side chain of Glu19 points almost in the opposite direction. In these structures, the plane of the peptide bond Ile18-Glu19 is approximately orthogonal to the plane of the extended segment. Owing to the structural mobility of the turn, the family of structures displays a dispersion in the relative position of the N- and C-terminal helices. The dispersion is, nevertheless, limited. When the different structures of the family are superimposed on the Cα of the residues in the C-terminal helixes, the axe of the N-terminal is dispersed in a cone with an opening of approximatively 90 degrees, and with a relative angle of about 80 degrees. Similar mutual orientations for two sequential helices, one of which transmembran and the other anfiphatic, have been found or hypothized for many small membrane bound proteins or peptides (Stopar, D. et al. (1996) Biochemistry, 35 (48), 5467–5473).

In some of the structures, the side chain εNH of Arg9, Arg13 and Arg14, whose chemical shifts are nearly independent of T, make hydrogen bonds with the adjacent side chain oxygen of Ser10, Ser16 and Thr17. For Arg25, with large $\Delta\delta N$ (T), there were no obvious candidates for hydrogen bond donors. The side chain $NH_2$ of the glutamines and asparagines could form hydrogen bond net works parallel to the helical axis.

With regards to the phosphorylation of PLB, we find important that the phosphorylation site Ser16 is readily accessible and exposed to the solvent. Thr17, on the N-terminal helix, is facing the C-terminal helix and appears less exposed to the solvent than Ser16. Due to the pitch of the α-helix, Arg13 and Arg14 are also exposed with orientations that lag 60 degrees in phase with respect to Ser16 and Thr17 on the same side of the helix. The presence of positively charged residues in the vicinity of a serine or threonine residue is often seen in a substrate for phosphokinases (e.g. in Troponin I).

Figure 3:
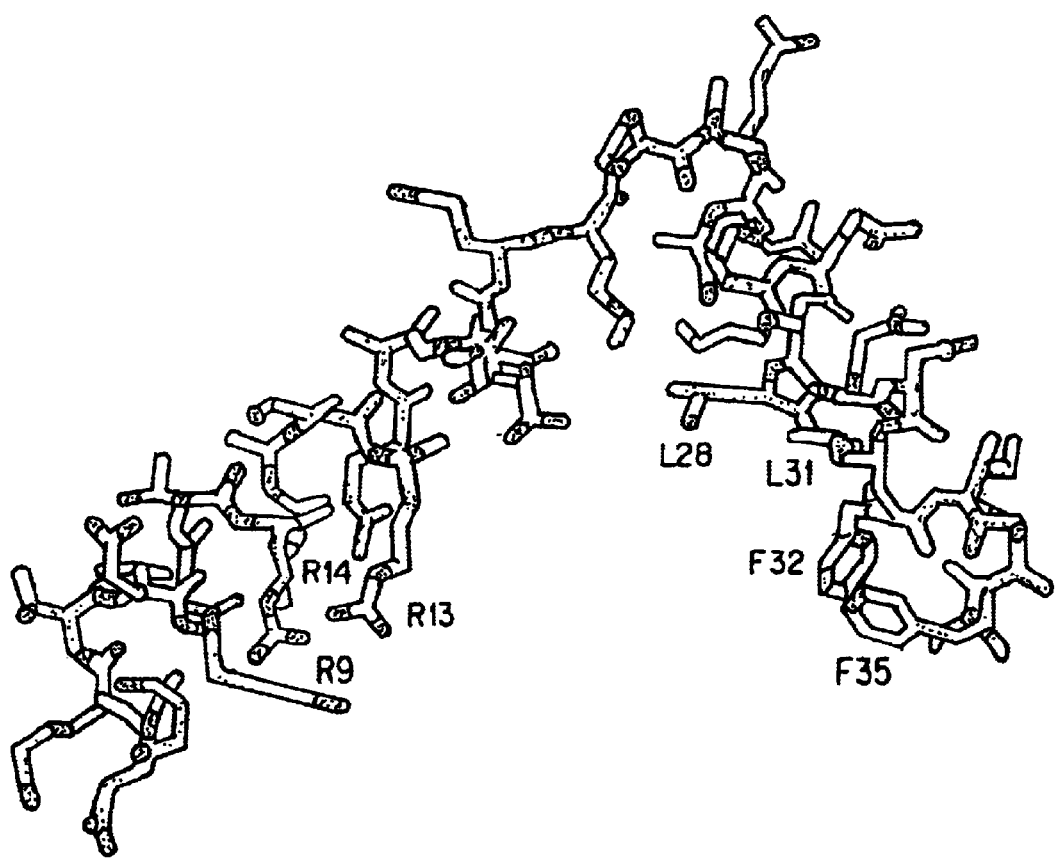
FIG. 3 is an illustration of the NMR structure of PLB (1–36) (SEQ ID NO: 9).

We find that one side of the N-terminal helix is predominantly polar or hydrophilic. The same is true for the C-terminal helix, whose polar residues are located on one side while leaving the other side dominated by lipophilic side chains. Owing to the relative orientation of the helices, it can be noted that the hydrophilic side of the N-terminal helix faces always the lipophilic side of the C-terminal helix. This defines a pocket which could be described as an amphipathic armpit. In this pocket, the relative position of the polar residues on the N-terminal and of the lipophilic residues on the C-terminal can be conveniently described by use of two centroids calculated by averaging the coordinates of selected side chains. The coordinates of the side chains of Arg13, Arg9 and Tyr6 were used to build the centroid relative to the N-terminal and the coordinates of the side chains of Phe32 and Phe35 were used to build up the centroid relative to the C-terminal. The distance between these two centroids was calculated for every structure of the family and was 18.5±4.5 Å. The refined structure of PLB (1–36) (SEQ ID NO: 9) is shown in FIG. 3.

EXAMPLE 2

Structure Of The Cyclic Peptide cP226 (SEQ ID NO: 10)

Peptide Synthesis, Cyclization and Purification

The linear peptide having the amino acid sequence CYWELEWLPCA (SEQ ID NO: 10) was synthesized with an automated peptide synthesizer (Perkin-Elmer, Applied Biosystems 431A) using the fluorenylmethoxycarbonyl-strategy. The synthesis was started from the carboxy-terminal end. The side chain protecting groups employed during the synthesis were: Trityl (Trt) for Cys, tert-Butoxy (OtBu) for Glu, and tert-Butyl (tBu) for Tyr.

The amount of the preloaded resin was 100 μmol and the quantity of the amino-acids at each step of the synthesis was 1 mmol.

The peptide cleavage from the resin support (originally preloaded Wang resin) as well as cleavage of the side chain pretection groups was carried out in a mixture of ethanedithiol:thioanisole:water:trifluoroaceticacid=250 µl: 500 µl :500 µl: 10 ml for 1.5 hours at room temperature. After that the peptide was precipitated and washed three times with diethylether, and lyophilized.

The amino-acids and the preloaded resins used for the peptide synthesis were obtained from Novabiochem. Trifluoroacetic-acid (TFA) was produced by Perkin-Elmer, ethanedithiol (EDT) and thioanisole were manufactured by Fluka.

The cyclic peptide cP226 (SEQ ID NO: 10) was reconstituted from the linear CYWELEWLPCA peptide (SEQ ID NO: 10) by dissolving 0.5 mg/ml the purified peptide into 10 mM $(NH_4)_2CO_3$ and the oxidation of the SH groups of the two cyteine residues to form intramolecular disulphide bridge was achieved by leaving the solution at room temperature for 1–2 days. The reaction was followed by HPLC chromatography from the peaks of the linear and the cyclic peptide was varied as a fuction of time.

The peptides, both the linear and the cyclic cP226 (SEQ ID NO: 10), were purified and separated by reverse phase HPLC-chromatography (C8, Aquqpore Octyl, 30 µm, 10×100 mm, Perkin-Elmer) using 30 min linear gradient from 0.1% TFA to 100% acetonitrile. The obtained peptides were characterized by mass spectrometry.

NMR Spectra of cP226 (SEQ ID NO: 10)

$^1$H-NMR spectra were acquired at 400.13 MHz and at 599.86 MHz on a Bruker ARX400 and a Varian UNITY 600 NMR spectrometer respectively. 1D and 2D NMR spectra were obtained for a 1 mM solution of the cyclic peptide in water. The pH was adjusted to 6.50±0.02 (uncorrected for deuterium isotope effects) with microliter amounts of NaOD. COSY, TOCSY (30–90 ms) and NOESY (200–400 ms) spectra were recorded at 5, 10, 15 and 27° C., by the States-TPPI method, using a spectral width of 8.5 ppm. The 2D data was weighted and Fourier transformed to 2 k ¥1 k real point matrices. The transmitter presaturated (2.0 s) residual solvent line was reduced by deconvolution. The spectra were referenced to the residual solvent signal (4.75 ppm at 27° C., –10 ppb/° C.).

Assignment of the NMR Spectra of cP226 (SEQ ID NO: 10)

The spin-system and sequential assignments were derived according to Wüthrich as in EXAMPLE 1, by use of COSY, TOCSY and NOESY spectra acquired at 5, 10 and 27° C. Differences in the temperature dependences of the amido proton chemical shifts were sufficient to unravel resonance overlap. Stereospecific assignments for non-degenerated methylenes were deduced from coupling constants $J_{H\alpha H\beta}$ measured from the COSY spectra and from intra residual NOE-cross peak intensities.

cP226 (SEQ ID NO: 10) Structure Generation And Refinement

A series of NOESY spectra was acquired at 10° C. with different mixing times (200, 300, 400 ms). The integrated cross peak intensities (1) were used in a NOESY-built-up-analysis. Distance restraints were extracted from the inital slope of a second-order polynomial curve fitted to the volumes of the cross peaks integrated from the NOE-series, with the initial condition $I_{(\tau m=0)}=0$. Intra methylene and sequential NOEs served for the calibration. The distances were initially classified as short (1.8–2.5 Å), medium (1.8–3.5 Å) or long (3.0–6.0 Å) for the generation of the first set of structures. When a distance could not be calculated from the built-up curve, owing to a partial (>20%) overlap, a poor signal-to-noise ratio or disturbances, it was only required that the distance was <5.0 Å. The upper bounds were extended by 1.0 Å for each pseudo atom. The restraint data were supplemented with distance restraints, which were based on strong, medium and weak NOEs, from the 300 ms NOE-spectrum acquired at 10° C.

Coupling constants (J) were measured by the J-doubling method from fine structures of COSY cross peaks. Dihedrals φ and χ, which were characterised by intermediate J, were not constrained but small and large $J_{NH\alpha}$ and $J_{H\alpha H\beta}$ were related to staggered conformers (±30 degrees) on the basis of Karplus functions and intra residual NOEs. The H—H distance and dihedral angle restraints were calculated. Finally, the data were imported into the software InsightII (Molecular Simulations, Inc.) in order to generate, evaluate and refine the structures. Simulated NOESY spectra were back calculated. The protein coordinate files were analysed by the software PROMOTIF v2.0.

Structures were generated by distance geometry (DGII) followed by simulated annealing (force field AMBER). A set of 30 structures was computed. The structures with the least restraint violations were used to back calculate NOE-matrices. Based on the comparison of the back-calculated and experimental NOE-spectra it became possible to unambiguously identify more NOEs and impose corresponding distance restraints. A new set of 30 structures was subsequently calculated. From this new family, 12 structures with at most one violation larger than 0.3 Å were selected and examined further. The distance restraints corresponding to well-resolved cross peaks were refined by an iterative relaxation matrix method (IRMA) based on a structure without restraint violations (>0.2 Å, >0 deg). The upper bounds were kept within at least 10% of the exact distance given by IRMA to take into account the uncertainty in $\tau_c$. The refined restraint set was subsequently used to refine the coordinates by simulated annealing.

The resulting final family of 12 structures was visualized by the graphic software MOLMOL (Koradi, R. et al. (1996) J Mol Graphics 14, 51–55).

Assignment results

The complete spin-system and sequential assignments were obtained under the experimental conditions described. It was necessary to run the NOESY experiments at low temperature (<10° C.) and with relatively long mixing time (>300 ms) to induce enough magnetization transfet and visualize the cross peaks. The assignments are listed in Table VI.

cP226 (SEQ ID NO: 10) spectra displayed chemical shift dispersion over 8.5 ppm. $C_\alpha H$ shifts ranged from 3.9 to 4.7 ppm and most of the NH shifts were confined between 7.8 and 8.5 ppm, but for Tyr2 and Leu8 the NH resonances were shifted up-field, to 6.9 and 7.3 ppm respectively. There were no signals of methyl groups at very high field (>0 ppm).

Figure 10:
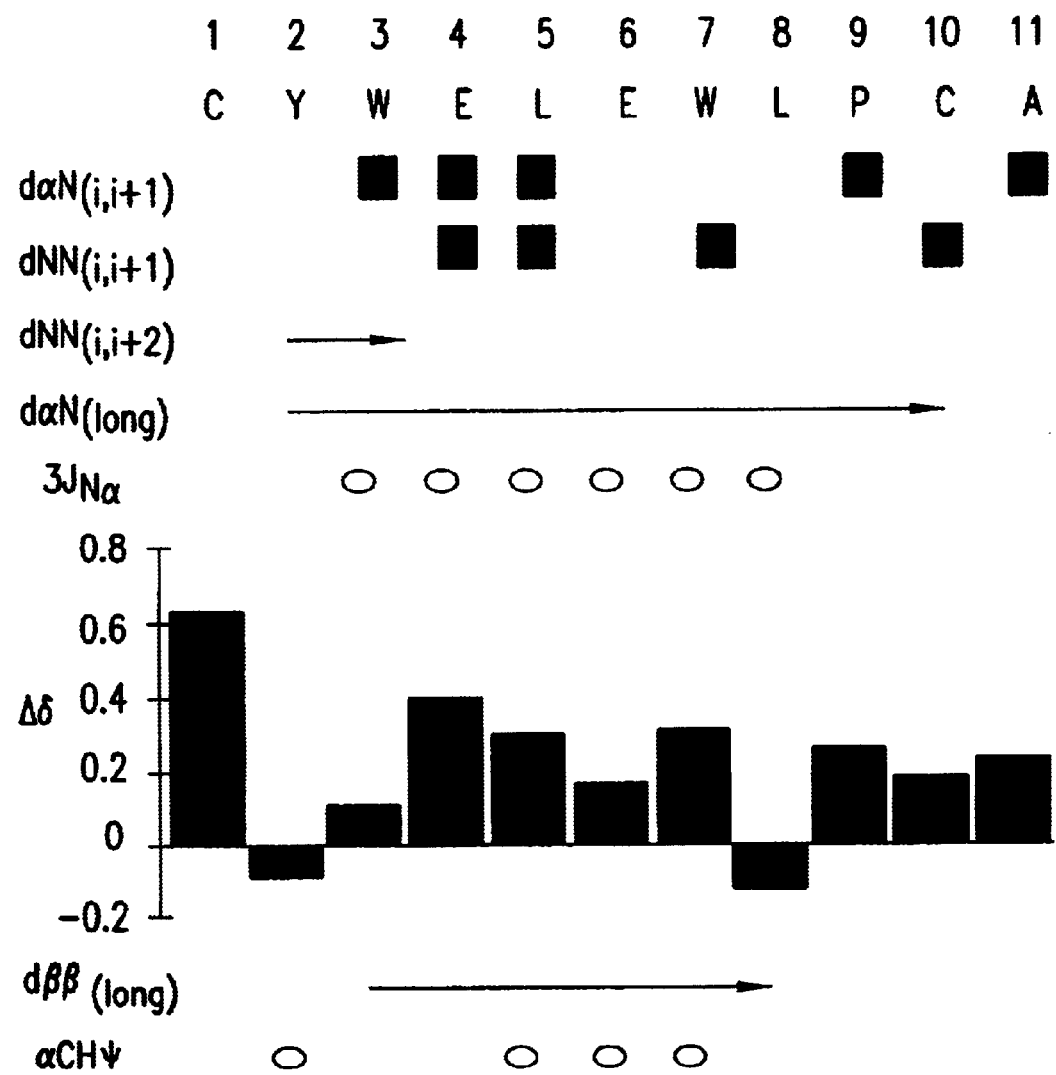
FIG. 10 is the summary of the observed sequential and medium-range NOE connectivities for cP226 (SEQ ID NO: 10).

FIG. 10 is a summary of the observed sequential and medium-range NOE connectivities for CP226 (SEQ ID NO: 10) in 90% $H_2O/10\%$ $D_2O$, pH 6.50 at 10° C. The assignments were made from NOESY spectra acquired at 300 and 400 ms mixing times. Sequential NOEs are represented by shaded blocks. Medium-range NOEs are represented by arrows connecting the appropriate residues. Open circles denote $^3J_{NH\alpha CH}$ coupling constants bigger than 8 Hz. The secondary shift (Δδ) of αCH is defined as the difference between the observed chemical shift and the random coil chemical shift for each residue. Negative (upfield) and positive (downfield) Δδ values are associated to the secondary structure according to Wishart et al., Biochemistry (1992), 31, 1647–1651.

In total 120 NOEs were assigned. Not all the 9 possible intra NH—CαH correlations were observed in the finger print region. Most of the corresponding NOEs were fairly weak. Only four sequential $NH_i$—$NH_{i+1}$ and one $NH_i$—$NH_{i+2}$ NOEs were present. Some $NH_{i+n}$—$C_\beta H_i$ were visible in the NOESY spectra and facilitated the sequential assignment. The secondary shift ($\Delta\delta$) of $\alpha CH$, defined as the difference between the observed chemical shift and the random coil chemical shift for each residue, gave evidence of bended structure (FIG. 10). NOEs derived from interactions longer than i>i+4 (across the cycle) were observed for protons of the side chains of Trp3 and Leu8 and for protons of Tyr2 and Cys10.

J-couplings between NH and $C_\alpha H$ (measured from the COSY cross peaks) were large for most residues. The couplings for all residues were above 8 Hz, suggesting that the $\phi$ angles have predominantly values of 120±30°.The proline was in a trans-conformation.

Structure of cP226 (SEQ ID NO: 10)

The structure of cP226 (SEQ ID NO: 10) was determined from 110 distances and 8 dihedral restraints excluding those that were defined more accurately by the covalent structure alone. These redundant NOE-derived restraints were consistent with the covalently imposed distance limits, which indicated that the calibration of distances was reasonable. On average there were 10 non-trivial NOE-derived restraints per residue. The residues in the central part of the peptide (from Trp3 to Leu8) had more restrain per residue than the average. This is at least partly due to the fact that there were on average more protons with non-degenerated shifts per residue in that zone.

The structure generation resulted in a family of structures all of which show bend-coil-bend motif (MOLMOL). The root mean square deviation was computed from the family of 12 structures with no distance violations above 0.3 Å and no dihedral violations. The small distance restraint violations occurred primarily among the side chain groups, e.g. the tyrosine side chain. This may be a result of excessive mobility in these parts, which could give rise to non-simultaneous NOEs. RMSD per residue was computed and represented roughly an inverse correlation with the number of restraints per residue, as expected. In average the atoms were defined to a precision of 0.96 Å (backbone only) and of 2.02 Å (all atoms) and, if calculated only for the portion from Trp3 to Trp7, to a precision of 0.72 Å (backbone only) and of 1.87 Å (all atoms) (Table VII).

The lipophilic side chains of Trp3, Leu5, Trp7 and Leu8 were clustered on one side of the cyclic peptide, leaving the most of the polar carbonyl and amine groups of the backbone on the other side.

The structure of CP226 (SEQ ID NO: 10) shown in this report was docked on the structure of PLB (1–36) (SEQ ID NO: 9) described above. The comparison of the two structures confirm the hypothesis that the two glutamate residues on CP226 (SEQ ID NO: 10) may partecipate to the binding by coupling with Arg9 and Arg 13 on PLB (1–36) (SEQ ID NO: 9), exposing the lipophilic cluster of CP226 (SEQ ID NO: 10) to the lipophilic outer part of the C-terminal helix of PLB(1–36) (SEQ ID NO: 9).

Figure 11:
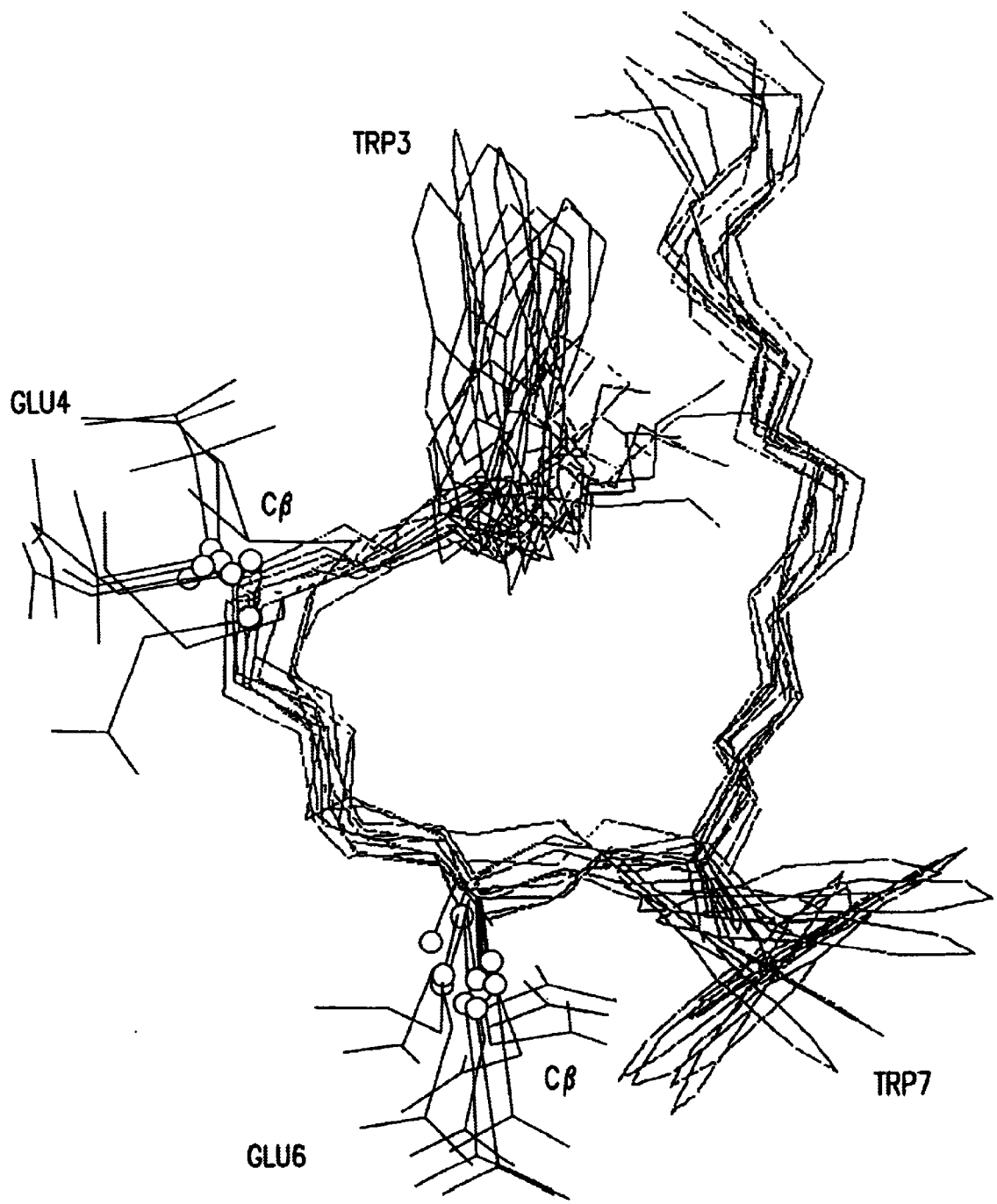
FIG. 11 is an illustration of the family of 12 structures of cP226 (SEQ ID NO: 10) deduced from NMR data.

FIG. 11 shows a family of 12 structures of CP226 (SEQ ID NO: 10) deduced from NMR data. The backbones, the heavy atoms of the Trp3 and Trp7 side chains, the heavy atoms of the Glu4 and Glu6 side chains, the carbon β of Glu4 and Glu6 is shown. The distance between the beta carbons of the two glutamate residues (FIG. 11) was highly conservative (8.3±0.9 Å). This information can be useful to design small molecules in which two acetate residues mimic the position of Glu4 and Glu6 on CP226 (SEQ ID NO: 10). In the same way, the distance of the lipophilic cluster from the two glutamate residues will also be useful in the drug design process.

EXAMPLE 3

Activity Assays

Experiment 1

Effect on Calcium Uptake into the SR Vesicles Prepared from Cardiac and Fast Skeletal Muscle The inhibitory effect of a given compound on phospholamban can be demonstrated by measuring the effect of the compound on calcium uptake into the SR vesicles prepared from cardiac tissue and into SR vesicles prepared from fast skeletal muscle (psoas m.). Both kind of SR vesicles contain $Ca^{2+}$-ATPase but the vesicles from the fast skeletal muscle do not contain phospholamban (Hoh JFY, "Muscle fiber types and function", Current Opinion in Rheumatology, 4:801–808, 1992). An increase in the calcium uptake into the SR vesicles prepared from cardiac tissue but not into the SR vesicles prepared from fast skeletal muscle indicates that the compound relieves the inhibitory effect of phospholamban on SR $Ca^{2+}$-ATPase and thus acts as a phospholamban inhibitor. Since phospholamban represses both the rates of relaxation and contraction in the mammalian heart through its inhibitory effects on the cardiac SR $Ca^{2+}$-ATPase, a compound relieving these effects is potentially useful in the treatment of heart failure.

Method

Guinea pigs (10–12) were decapited. Their hearts or the psoas muscles were excised, washed in ice-cold 0.9% NaCl and cut into pieces in a buffer containing 20 mM Tris-maleate, 0.3 M sucrose, pH 7.0. Thereafter tissue pieces were homogenized with Polytron and further with Potter (10 strokes). The homogenate was centrifugated at 1000 g for 15 min at 4° C. The supernatant was collected and the pellet was resuspended into 5 ml of the buffer (20 mM Tris-maleate, 0.3 M sucrose, pH 7.0) and recentrifugated at 1000 g for 10 min at 4° C. The obtained supernatant was combined with the earlier collected supernatant and centrifugated once again at 10 000 g for 20 min at 4° C. The final supernatant was filtered into a bottle equipped with a magnetic stirrer. KCl was added to the filtered supernatant to achieve the final concentration of 0.6 M (at 4° C.). The obtained solution was centrifugated at 100 000 g for 60 min at 4° C. The pellet was suspended in 5 ml of the buffer containing 20 mM Tris-maleate, 0.3 M sucrose, pH 7.0 and centrifugated at 100 000 g for 60 min at 4° C. The obtained pellet was suspended in 5 ml of buffer containing 20 mM Tris-maleate, 0.3 M sucrose, 0.1 M KCl, pH 7.0 and stored at −80° C. until use. The protein concentration was also measured in order to standardise the separately prepared vesicle preparations.

In the calcium uptake assay, the fluorescent indicator, fluo-3 was used to detect the decrease of the extravesicular $Ca^{2+}$-concentration, when the SR $Ca^{2+}$ATPase was transferring $Ca^{2+}$ from the extravesicular space into the SR-vesicles.

The SR-vesicles obtained above (50 µg protein/ml) were pre-incubated with or without the test compound at 37° C. for 5 min in the assay buffer containing 40 mM imidazole, 95 mM KCl, 5 mM $NaN_3$, 5 mM $MgCl_2$, 0.5 mM EGTA, 5 mM potassium oxalate, 2 µM ruthenium red, 5 µM fluo-3, pH 7.0. The free calcium was adjusted to 0.1 µM or to 0.04 µM by $CaCl_2$. The reaction was initiated by adding ATP (5 mM). The final reaction volume was 1.5 ml. The fluorescence of reaction mixture was measured for 3 min by using the excitation and emission wavelengths of 510 nm and 530 nm, respectively.

Results

Figure 12A:
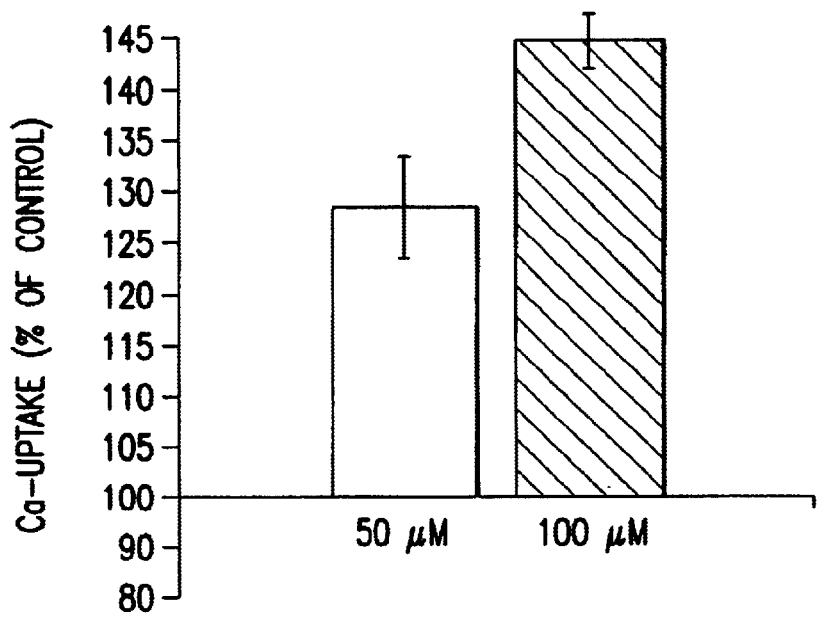
FIGS. 12A and 12B show the effect of the compound of Example 1c (50 and 100 µM) on the $Ca^{2+}$ uptake rate into the cardiac (A) and fast skeletal muscle (B) SR vesicles.
Figure 12B:
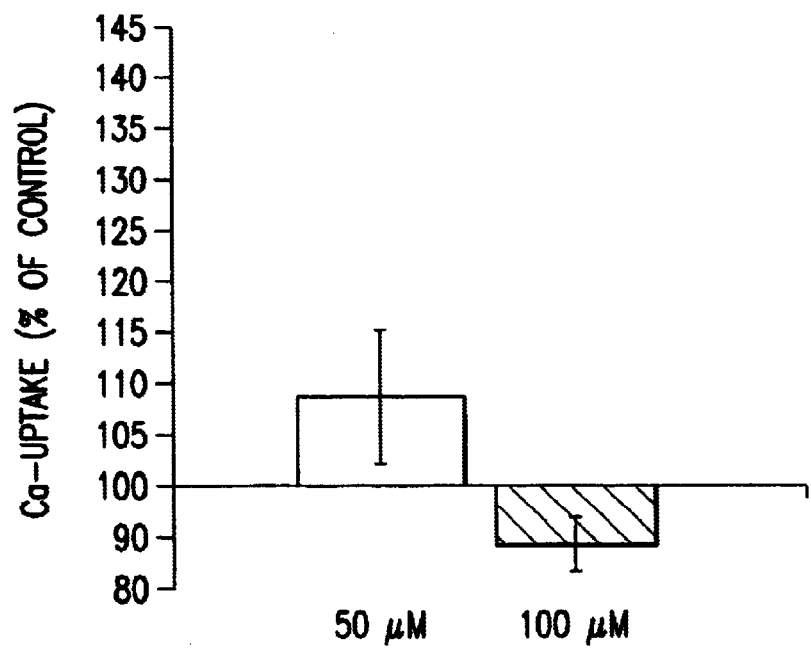

FIGS. 12A and 12B show the effect of the compound of Example 1c (50 and 100 μM) on the $Ca^{2+}$ uptake rate into the cardiac (A) and fast skeletal muscle (B) SR vesicles. It can be seen that the compound of the invention accelerated the calcium uptake into the cardiac SR vesicles but did not change the calcium uptake into the SR vesicle prepared from the fast skeletal muscle.

Table VIII shows the effects of various compounds of the invention on the $Ca^{2+}$ uptake rate into the cardiac (A) and fast skeletal muscle (B) SR vesicles. The experiments were carried out at 0.1 μM and 0.04 μM free calcium concentrations, respectively.

TABLE VIII

Stimulation (%) of the $Ca^{2+}$ uptake into the vesicle preparations obtained from the ventricular myocardium (A) and fast skeletal muscle (B) of the guinea-pig heart.

| Compound of Example No. | The stimulation (%) of $Ca^{2+}$ uptake | |
| --- | --- | --- |
| (100 μM) | A | B |
| 3c** | 51 | 0 |
| 2c | 26 | −1 |
| 7c | 5 | −17 |
| 8g* | 18 | 0 |
| 11b | 28 | nd |
| 12 | 32 | nd |
| 13d*** | 23 | nd |
| 14c* | 18 | nd |
| 18e | 13 | nd |
| 21 | 11 | nd |
| 23**** | 20 | nd |

*10 μm, 20 μM, *50 μM, ****5 μM
nd = not determined

Experiment 2

The Effects on the Left Ventricular Pressure Derivatives

Method

Guinea-pigs of either sex weighing 300–400 g were used in the study. After the guinea-pig was sacrificed by a blow on the skull and decapitated the heart was rapidly excised. The heart was then rinsed in cold oxygenated perfusion buffer. A cannula was inserted into the aorta and secured with a ligature. Retrograde perfusion began as soon as the heart was placed in a thermostatically controlled moist chamber of the Langendorff apparatus. Modified Tyrode solution (37° C.), equilibrated in a thermostatically controlled bulb oxygenator with carbogen (95% $O_2$ and 5% $CO_2$) was used as a perfusion buffer. The composition of the Tyrode solution was (in mM): NaCl 135; $MgCl_2 \times 6H_2O$ 1; KCl 5; $CaCl_2 \times 2H_2O$ 2; $NaHCO_3$ 15; $Na_2HPO_4 \times 2H_2O$ 1; glucose 10; pH 7.3–7.4. The experiments were carried out under constant pressure condition (50 mmHg). After a short prestabilization (10 min) a latex balloon (size 4) was carefully placed into the left ventricle through the left pulmonary vein and the left atrium. The latex balloon was attached to a stainless-steel cannula coupled with a pressure transducer. The latex balloon, the cannula and the chamber of the pressure transducer were filled with ethylene glycol/water (1:1) mixture avoiding any air-bubble. The isovolumetric left ventricular pressure was recorded through the pressure transducer. At the beginning of the experiment, the volume of the balloon was adjusted to obtain a diastolic pressure of approximately 5 mmHg. Before starting the experiment, the heart was allowed to stabilise further for 30–50 min with vehicle (0.1% DMSO) in the perfusion buffer.

After 15 min baseline recording various concentrations of the test compound were added to the perfusion buffer at 15 min intervals. The concentration range of 0.3–30 μM was tested. The vehicle concentration (0.1% DMSO) was kept constant throughout the experiment.

Results

The $EC_{50}$ values and maximum effects (% change from baseline) of various compounds of the invention on left ventricular systolic pressure are given in Table IX.

TABLE IX

The $EC_{50}$ values and maximum effects (% change from baseline) on left ventricular systolic pressure.

| Compound of Example No. | $EC_{50}$ (μM) | maximum effect (%) |
| --- | --- | --- |
| 1c | 9 | +52 at 30 μM |
| 3c | 4 | +63 at 10 μM |
| 5c | >10 | +14 at 30 μM |
| 6c | 0.5 | +25 at 10 μM |
| 7c | 2.5 | +29 at 10 μM |
| 8g | 2 | +64 at 10 μM |
| 9d | 5 | +50 at 30 μM |
| 12 | 5 | +22 at 10 μM |
| 13d | 10 | +48 at 30 μM |
| 14c | 1.5 | +25 at 10 μM |
| 15c | 3 | +37 at 10 μM |
| 16c | 10 | +57 at 30 μM |
| 18e | 10 | +35 at 30 μM |
| 19e | 6 | +39 at 30 μM |

EXAMPLE 4

The preparation of PLB deactivators is described below by the following non-limiting examples.

Example 1

Preparation of 3-Benzyl-5,7-bis[(1H-tetrazol-5-yl)-methoxy]-4-methyl-2H-1-benzopyran-2-one a) 3-Benzyl-5,7-dihydroxy-4-methyl-2H-1-benzopyran-2-one

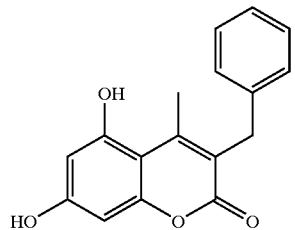

A solution of phloroglucinol dihydrate (20 g) and ethyl 2-benzylaceto-acetate (27.5 ml) in ethanol (320 ml) was treated with dry HCl at 0° C. for five hours and the solution was kept at that temperature overnight. The yellow solution was concentrated and triturated with water, the solids filtered, washed with water and dried. The resulting hydrate was thrice evaporated to dryness from toluene, triturated with pethroleum ether (bp. 40–60° C.) and filtered. Yield 33,4 g (96%). Melting point 258–260° C.

$^1$H-NMR (DMSO-d$_6$, 400 MHz): 2.525 (s, 3H, CH$_3$), 3.887 (s, 2 H, CH$_2$Ph), 6.171 (d, 1H, J=2,4 Hz), 6.274 (d, 1H, J=2,4 Hz), 7.167–7.279 (m, 5H, Ph), 10.2 (s, 1H, OH), 10.47 (s, 1H, OH).

b) 3-Benzyl-5,7-bis(cyanomethoxy)-4-methyl-2H-1-benzopyran-2-one

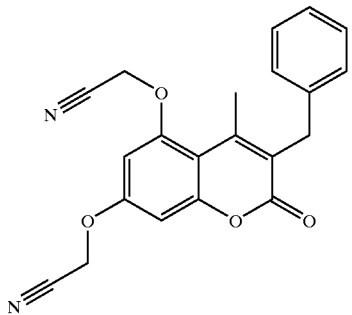

Chloracetonitrile (6.86 g), potassium carbonate (23.9 g) and 12.2 g of the product from example 1a were stirred in 120 ml of DMF at 100° C. under nitrogen for two hours. The reaction mixture was cooled and poured into ice water. The solids were filtered and washed with water. Yield 13.8 g (88%). Melting point 147–154° C.

$^1$H-NMR (DMSO-d$_6$, 400 MHz): 2.525 (s, 3H, CH$_3$), 3.969 (s, 2H, CH$_2$Ph), 5.307 (s, 2H, OCH$_2$CN), 5.314 (s, 2H, OCH$_2$CN), 6.814 (d, 1 H, J=2.5 Hz), 6.940 (d, 1H, J=2.5 Hz), 7.18–7.292 (m, 5H, Ph).

c) 3-Benzyl-5,7-bis[(1H-tetrazol-5-yl)methoxy]-4-methyl-2H-1-benzopyran-2-one

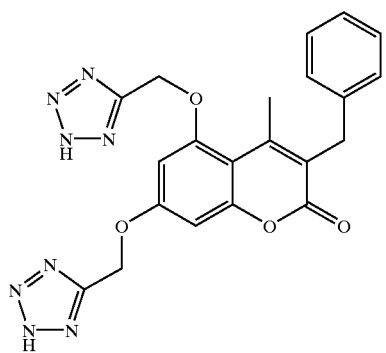

The product from example 1b (1 g), sodium azide (0.42 g) and ammonium chloride (0.34 g) were stirred in DMF (5 ml) under nitrogen at 100° C. for 5 hours. The reaction mixture was allowed to cool down and then poured into ice water. The pH of the solution was adjusted to 10–11 and then the solution either extracted once with ethyl acetate or filtered through CELITE. The solution was acidified to pH 2 with hydrochloric acid, kept at 5° C. and filtered. Yield 0.96 g (81%). Melting point 229–233° C.

$^1$H-NMR (DMSO-d$_6$, 400 MHz): 2.468 (s, 3H, CH$_3$), 3.937 (s, 2H, CH$_2$Ph), 5.596 (s, 2H, OCH$_2$Tet), 5.602 (s, 2H, OCH$_2$Tet), 6.832 (d, 1H, J=2.4 Hz), 6.851 (d, 1H, J=2.4 Hz), 7.171–7.283 (m, 5H, Ph).

Example 2

Preparation of 7,8,9,10-Tetrahydro-1,3-bis[(1H-tetrazol-5yl)methoxy]-7-phenyl-6H-dibenzo[b,d]pyran-6-one a) 7,8,9,10-Tetrahydro-1,3-dihydroxy-7-phenyl-6H-dibenzo[b,d]pyran-6-one

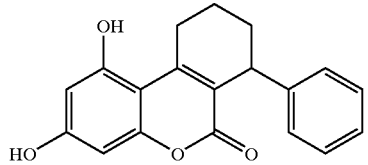

A solution of phloroglucinol (0.7 g) and 2-ethoxycarbonyl-3-phenylcyclohexanone (1,5 g) in ethanol was treated with dry HCl as described in example 1a. The product was first recrystallized from ethanol-water (1:1) and then triturated with ether. Yield 0.61 g.

$^1$H-NMR (DMSO-d$_6$, 400 MHz): 1.38–1.52 (m, 1H), 1.57–1.66 (m, 1H), 1.69–1.78 (m, 1H), 1.8–1.96 (m, 1H), 2.9–3.02 (m, 1H), 3.3–3.4 (m,1H), 4.050 (b, 1H), 6.157 (d, 1H, J=2.4 Hz), 6.297 (d, 1H, J=2.4 Hz), 7.076–7.265 (m, 5H), 10.153 (s, 1H), 10.456 (s, 1H).

b) 7,8,9,10-Tetrahydro-1,3-bis(cyanomethoxy)-7-phenyl-6H-dibenzo[b,d]pyran-6-one

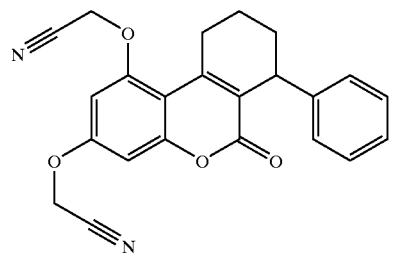

The product from example 2a (0.5 g) was treated with chloroacetonitrile (0.25 g) and potassium carbonate (1.12 g) in DMF (5 ml) as described in example 1b. Yield 0.6 g.

$^1$H-NMR (DMSO-d$_6$, 400 MHz): 1.38–1.58 (m, 1H), 1.6–1.7 (m, 1H), 1.7–1.76 (m, 1H), 1.89–1.99 (m, 1H), 2.9–3.03 (m, 1H), 3.2–3.28 (m 1H), 4.111(b, 1H), 5.314 (s, 2H), 5.349 (s, 2H), 6.840 (d, 1H, J=2.5 Hz), 6.925 (d, 1H, J=2.5 Hz), 7.108–7.274 (m, 5H).

c) 7,8,9,10-Tetrahydro-1,3-bis[(1H-tetrazol-5-yl)methoxy]-7-phenyl-6H-dibenzo[b,d]pyran-6-one

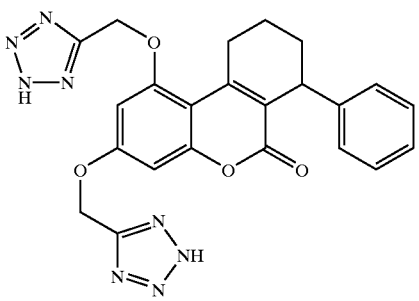

The product from example 2b (0.6 g) was treated with sodium azide (0.2 g) and ammonium chloride (0.17 g) in DMF (5 ml) as in example 1c. The product was recrystallized from a mixture of DMF, ethanol and water (approximately 1:2:3). Yield 0.41 g. Melting point: 153–154° C.

$^1$H-NMR (DMSO-d$_6$, 400 MHz): 1.38–1.5 (m, 1H), 1.5–1.6 (m, 1H), 1.69–1.76 (m, 1H), 1.87–1.96 (m, 1H), 2.9–3.05 (m, 1H), 3.2–3.3 (m, 1H), 4.094 (b, 1H), 5.602 (s, 2H), 5.643 (s, 2H), 6.832 (d, 1H, J=2.3 Hz), 6.851 (d, 1H, J=2.3.Hz), 7.089–7.212 (m, 5H).

Example 3

Preparation of 3-Benzyl-5,7-bis[(2,5-dihydro-5-oxo4H-1,2,4-oxadiazol-3-yl)-methoxy]-4-methyl-2H-1-benzopyran-2-one a) 3-Benzyl-5,7-bis[(hydroxyamidino)methoxy]-4-methyl-2H-1-benzopyran-2-one

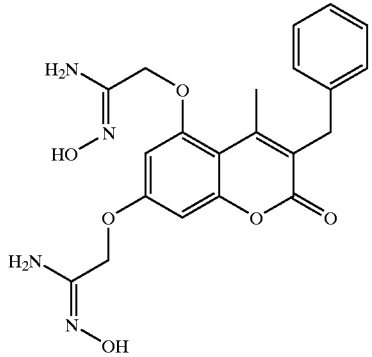

Triethylamine (1.94 ml) was added to a suspension of hydroxylamine hydrochloride (0.97 g) in DMSO (2 ml) and the resulting mixture stirred at room temperature for thirty minutes. The crystals were filtered and washed with ThF. The filtrate was concentrated and the product from example 1b (0.5 g) added. This solution was kept at 75° C. overnight. The reaction mixture was treated with ice water, the pH adjusted to 11 and the solids filtered, washed with water, and dried. Yield 0.5 g. Melting point: 155–160° C.

$^1$H-NMR (DMSO-d$_6$, 400 MHz): 2.56 (s, 3H, CH$_3$), 3.938 (s, 2H), 4.466 (s, 2H), 4.486 (s, 2H), 5.565 (s, H, NH$_2$), 5.709 (s, 2H, NH$_2$), 6.658 (d, 1H, J=2.4 Hz), 6.692 (d, 1H, J=2.4 Hz), 7.168–7.284 (m, 5H, Ph), 9.346 (s, 1H, OH), 9.362 (s, 1H, OH).

b) 3-Benzyl-5,7-bis[(ethoxycarbonyloxyamidino)methoxy]-4-methyl-2H-1benzopyran-2-one

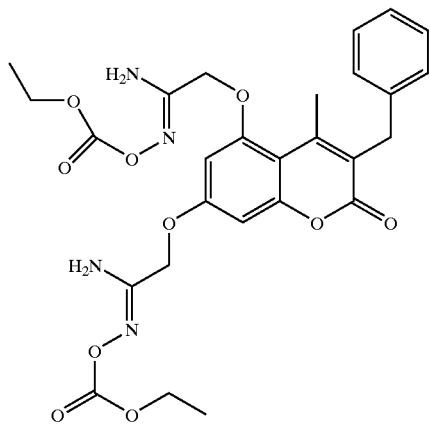

Ethyl chloroformiate (0.45 ml) was added to a solution of the product from example 3a (1 g) and pyridin (0.38 ml) in DMF (5 ml) at 0° C. The reaction mixture was kept at that temperature for an additional 30 minutes and then ice water added. The solids were filtered and washed with water. Yield 1.63 g. Melting point 87–92° C.

$^1$H-NMR (DMSO-d6, 400 MHz): 1.215–1.256 (m, 6H), 2.553 (s, 3H), 3.947 (s, 2H), 4.140–4.198 (m, 4H), 4.566 (s, 2H), 4.599 (s, 2H), 6.688 (d, 1H, J=2.4 Hz), 6.718 (d, 1H, J=2.4 Hz), 6.792 (b, 2H, NH$_2$), 6.818 (b, 2H, NH$_2$), 7.171–7.285 (m, 5H).

c) 3-Benzyl-5,7-bis[(2,5-dihydro-5-oxo-4H-1,2,4-oxadiazol-3-yl)-methoxy]-4-methyl-2H-1-benzopyran-2-one

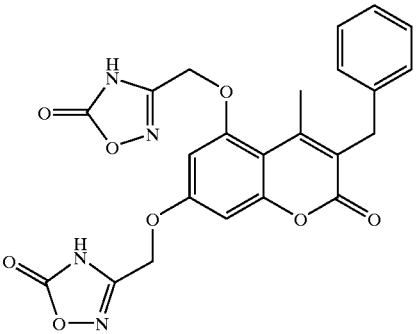

The product from the previous example (1.5 g) and DBU (0.8 ml) in DMF (5 ml) was stirred at room temperature overnight. The reaction mixture was treated with ice water and acidified. The solids were filtered and washed with water. The resulting solid mass was taken in 0.1 N sodium hydroxide solution, treated with activated carbon and finally acidified. Yield 0.64 g. Melting point: 130–136° C.

$^1$H-NMR (DMSO-d$_6$, 400 MHz): 2.524 (s, 3H), 3.954 (s, 2H), 5.187 (s, 2H), 5.215 (s, 2H), 6.748 (d, 1H, J=2.4 Hz), 6.834 (d, 1H, J=2.4 Hz), 7.158–7.289 (m, 5H), 12.8 (b, 2H).

Example 4

Preparation of 7,8,9,10-Tetrahydro-bis[(1H-tetrazol-5-yl)methoxy]-1,3-dihydroxy-6H-dibenzo[b,d]pyran-6-one a) 7,8,9,10-Tetrahydro-1,3-dihydroxy-6H-dibenzo[b,d]pyran-6-one

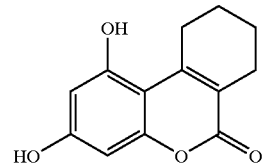

Phloroglucinol (1 g) and ethyl 2-oxocyclohexane carboxylate (1.32 g) were stirred in 75% sulfuric acid (10 ml) overnight, the mixture poured into ice water and filtered Yield: 1.55 g.

$^1$H-NMR (DMSO-d$_6$, 400 MHz): 1.65 (b, 4H), 2.345 (b, 2H), 3.037 (b, 2H), 6.138 (d, 1H, J=2.4 Hz), 6.245 (d, 1H, J=2.4 Hz), 10.069 (b, 1H, OH), 10.322 (s, 1H, OH).

b) 7,8,9,10-Tetrahydro-bis(cyanomethoxy)-1,3-dihydroxy-6H-dibenzo[b,d]pyran-6-one

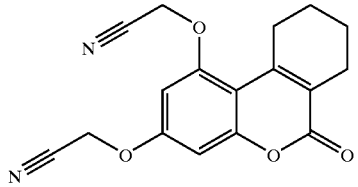

The product from the previous example (0.5 g), chloroacetonitrile (0.34 g) and potassium carbonate (1.5 g) in DMF (5 ml) were reacted as in example 1b. Yield: 0.44

$^1$H-NMR (DMSO-d$_6$, 400 MHz): 1.68 (b, 4H), 2.41 (b, 2H), 3.00 (b, 2H), 5.297 (s, 2H), 5.309 (s, 2H), 6.797 (d, 1H, J=2.4 Hz), 6.899 (d, 1H, J=2.4 Hz).

c) 7,8,9,10-Tetrahydro-bis[(1H-tetrazol-5-yl)methoxy]-1,3-dihydroxy-6H-dibenzo[b,d]pyran-6-one

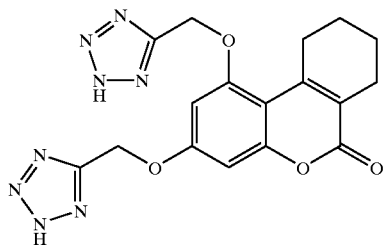

The product from the previous example (0.4 g) was treated with sodium azide (0.18 g) and ammonium chloride (0.14 g) in DMF (2.5 ml) as in example 1c. The product was recrystallized from ethanol-DMF (1:1). Yield 0.17 g. Melting point 283–286° C.

$^1$H-NMR (DMSO-$d_6$, 400 MHz): 1.626 (b, 4H), 2.393 (b, 2H), 2.971 (b, 2H), 5.583 (s, 2H), 5.599 (s, 2H), 6.811 (s, 2H).

Example 5

Preparation of 5,7-Bis[(1H-tetrazol-5-yl)methoxy]-4-phenyl-2H-1-benzopyran-2-one a) 5,7-Dihydroxy-4-phenyl-2H-1-benzopyran-2-one

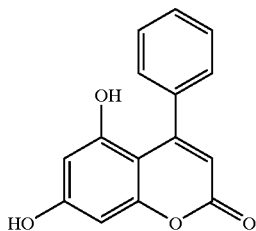

A solution of phloroglucinol (2.00 g) and ethyl benzoylacetate (3.05 g) in ethanol (30 ml) was treated with dry HCl as described in example 1a. The product was recrystallized from ethanol-water (1:1). Yield 3.0 g (75%).

$^1$H-NMR (DMSO-$d_{6, 300}$ MHz): 5.739 (s, 1H, CH=C), 6.155 (d, 1H, J=2.3 Hz), 6.263 (d, 1H, J=2.3 Hz), 7.305–7.381 (m, 5H, Ph), 10.084 (s, 1H, OH), 10.368 (s, 1H, OH).

b) 5,7-Bis(cyanomethoxy)-4-phenyl-2H-1-benzopyran-2-one

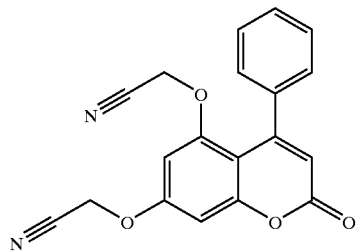

The product from previous example (1.00 g) was treated with chloroaceto-nitrile (0.62 g) and potassium carbonate (2.72 g) in DMF (5 ml) as described in example 1b. The reaction mixture was poured into ice water and the mixture extracted with ethyl acetate. Ethyl acetate was washed with 1 M NaOH, dried with sodium sulfate and evaporated. The product was recrystallized from isopropanol. Yield 0.41 g (31%).

$^1$H-NMR (DMSO-$d_6$, 300 MHz): 4.845 (s, 2H, OCH$_2$CN), 5.344 (s, 2H, OCH$_2$CN), 6.086 (s, 1H, CH=C), 6.770 (d, 1H, J=2.4 Hz), 7.040 (d, 1H, J=2.4 Hz), 7.320–7.443 (m, 5H, Ph).

c) 5,7-Bis[(1H-tetrazol-5-yl)methoxy]-4-phenyl-2H-1-benzopyran-2-one

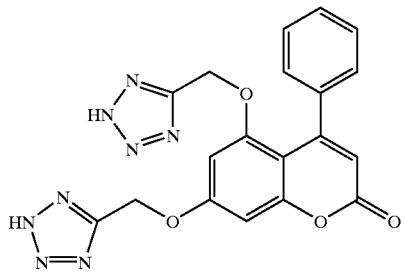

The product from previous example (0.40 g) was treated with sodium azide (0.16 g) and ammonium chloride (0.14 g) in DMF (2 ml) at 100° C. for 2 hours. The product was isolated as described in example 1c. Yield: 0.40 g (79%). Melting point 222–224° C.

$^1$H-NMR (DMSO-$d_6$, 400 MHz): 5.148 (s, 2H, OCH$_2$Tet), 5.649 (s, 2H, OCH$_2$Tet), 5.968 (s, 1H, CH=C), 6.811 (d, 1H, J=2.3 Hz), 6.962 (d, 1H, J=2.3 Hz), 6.994–7.185 (m, 5H, Ph).

Example 6

Preparation of 7,8,9,10-Tetrahydro-1,3-bis[(1H-tetrazol-5-yl)methoxy]-8-phenyl-6H-dibenzo[b,d]pyran-6-one a) 7,8,9,10-Tetrahydro-1,3-dihydroxy-8-phenyl-6H-dibenzo[b,d]pyran-6-one

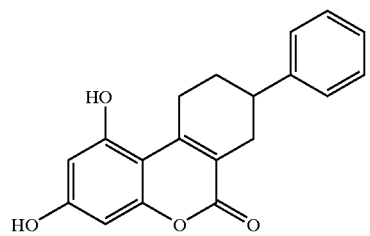

A solution of phloroglucinol (1.56 g) and ethyl 2-oxo-5-phenylcyclo-hexane-carboxylate (2.52 g) in ethanol (25 ml) was treated with dry HCl as described in example 1a. The precipitate was filtered and washed with water and ETOH. Yield 1.0 g (32%).

$^1$H-NMR (DMSO-$d_6$, 400 MHz): 1.72–1.82 (m, 1H), 2.01 (b, 1H), 2.317–2.387 (m, 1H), 2,707–2,763 (m, 1H), 2,830 (b, 1H), 3,041 (b, 1H), 3.35 and 3.40 (b, 1H), 6.174 (d, 1H, J=2.3 Hz), 6.277 (d, 1H, J=2.3 Hz), 7.200–7.350 (m, 5H, Ph), 10.131 (s, 1H, OH), 10.401 (s, 1H, OH).

b) 7,8,9,10-Tetrahydro-1,3-bis(cyanomethoxy)-8-phenyl-6H-dibenzo[b,d]pyran-6-one

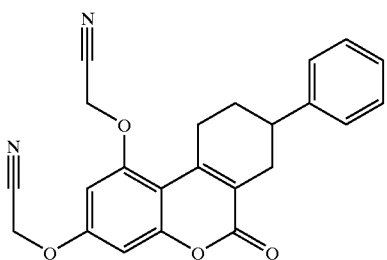

The product from previous example (1.0 g) was treated with chloro-acetonitrile (0.57 g) and potassium carbonate (1.0 g) in DMF (5 ml) as described in example 1b. DMF was evaporated and residue dissolved in EtOAc. Ethyl acetate was washed with 1 M NaOH, dried with sodium sulfate and evaporated. The product was recrystallized from acetone-isopropanol (1:3). Yield 0.50 g (40%).

$^1$H-NMR (DMSO-$d_6$, 300 MHz): 1.75–1.88 (m, 1H), 2.05 (b, 1H), 2.38–2.48 (m, 1H), 2.77–2.85 (m, 1H), 2.90 (b, 1H), 3.07 (b, 1H), 3.22 and 3.28 (b, 1H), 5.316 (s, 2H, OCH$_2$CN), 5.331 (s, 2H, OCH$_2$CN), 6.829 (d, 1H, J=2.5 Hz), 6.939 (d, 1H, J=2.5 Hz), 7.210–7.380 (m, 5H, Ph).

c) 7,8,9,10-Tetrahydro-1,3-bis[(1H-tetrazol-5-yl)methoxy]-8-phenyl-6H-dibenzo[b,d]pyran-6-one

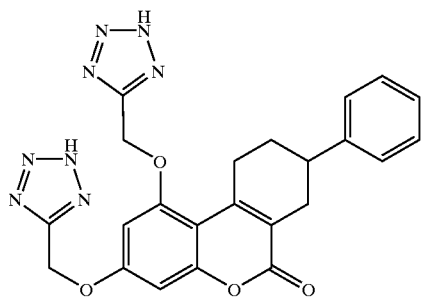

The product from previous example (0.30 g) was treated with sodium azide (0.10 g) and ammonium chloride (0.09 g) in DMF (2 ml) at 100° C. for 3.5 hours. The product was isolated in the same manner as in example 1c. Yield 0.30 g (82%). Melting point 235–245° C.

$^1$H-NMR (DMSO-$d_6$, 400 MHz): 1.70–1.80 (m, 1H), 1.96 (b, 1H), 2.38–2.446 (m, 1H), 2.836 (m, 2H), 3.052 (b, 1H), 3.252 and 3.301 (b, 1H), 5.604 (s, 2H, OCH$_2$CN), 5.632 (s, 2H, OCH$_2$CN), 6.827 (d, 1H, J=2.5 Hz), 6.858 (d, 1H, J=2.5 Hz), 7.209–7.351 (m, 5H, Ph).

Example 7

Preparation of 5,7-Bis[(1H-tetrazol-5-yl)methoxy]-4-methyl-3-(2-phenylethyl)-2H-1-benzopyran-2-one a) 5,7-Dihydroxy-4-methyl-3-(2-phenylethyl)-2H-1-benzopyran-2-one

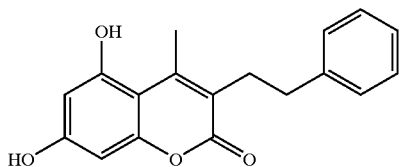

A solution of phloroglucinol (0.87 g) and ethyl 2-(2-phenylethyl)-acetoacetate (1.62 g) in ethanol (30 ml) was treated with dry HCl as described in example 1a. Yield: 1.77 g (87%). Melting point 248–252° C.

$^1$H-NMR (DMSO-$d_6$, 300 MHz): 2.413 (s, 3H, CH$_3$), 2.652–2.782 (m, 4H, CH$_2$CH$_2$), 6.151 (d, 1H, J=2.4 Hz), 6.256 (d, 1H, J=2.4 Hz), 7.183–7.304 (m, 5H, Ph), 10.137 (s, 1H, OH), 10.369 (s, 1H, OH).

b) 5,7-Bis(cyanomethoxy)-4-methyl-3-(2-phenylethyl)-2H-1-benzopyran-2-one

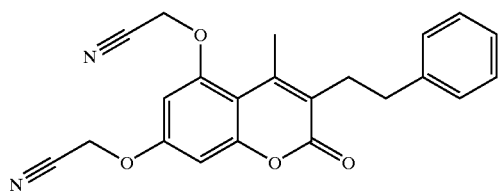

The product from previous example (0.90 g) was treated with chloroacetonitrile (0.48 g) and potassium carbonate (2.1 g) in DMF (5 ml) at 100° C. for 0.5 hours. The product was isolated as described in example 1b. Yield 1.00 g (88%). Melting point 179–183° C.

H-NMR (DMSO-$d_6$, 300 MHz): 2,384 (s, 3H, CH$_3$), 2.699–2,754 (m, 2H, CH$_2$CH$_2$), 2.805–2.841 (m, 2H, CH$_2$CH$_2$), 5,302 (s, 4H, OCH$_2$CN), 6,790 (d, 1H, J=2.5 Hz), 6.909 (d, 1H, J=2.5 Hz), 7.190–7.307 (m, 5H, Ph).

c) 5,7-Bis[(1H-tetrazol -5-yl)methoxy]-4-methyl-3-(2-phenylethyl)-2H-1-benzopyran-2-one

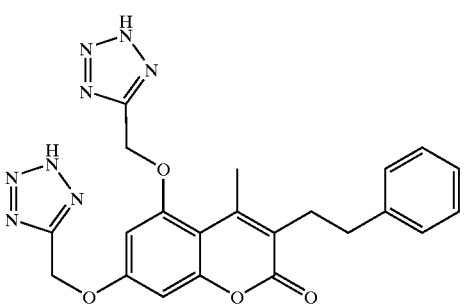

The product from previous example (0.40 g) was treated with sodium azide (0.15 g) and ammonium chloride (0.12 g) in DMF (2 ml) at 100° C. for 2.5 hours. The product was isolated as described in example 1c. Yield 0.385 g (78%). Melting point 248–250° C.

$^1$H-NMR (DMSO-$d_6$, 400 MHz): 2.368 (s, 3H, CH$_3$), 2.668–2.707 (m, 2H, CH$_2$CH$_2$), 2.783–2.822 (m, 2H, CH$_2$CH$_2$), 5.593 (s, 2H, OCH$_2$Tet), 5.604 (s, 2H, OCH$_2$Tet), 6.819 (d, 1H, J=2.3 Hz), 6.834 (d, 1H, J=2.3 Hz), 7.161–7.291 (m, 5H Ph).

Example 8

Preparation of 5,7-Bis[(1H-tetrazol-5-yl)methoxy]-1,3-dibenzyl-4-methyl-2(1H)-quinolinone a) 2-Benzyl-3-oxobutanoic acid 3,5-dimethoxyanilid

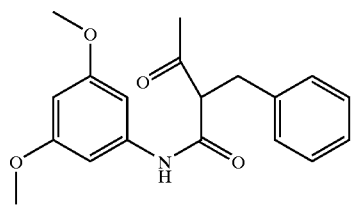

3,5-Dimethoxyaniline (5 g) was added in portions to a preheated (160° C.) ethyl 2-benzyl acetoacetate (15 ml) under nitrogen and kept at that temperature for 60 minutes. The cooled solution was diluted with heptane-ethyl ether and filtered. Yield 5.2g(49%).

$^1$-H-NMR (DMSO-d$_6$, 300 MHz): 2.183 (s, 3H), 3.069 (d, 2H, J=7.2 Hz), 3.923 (t, 1H, J=7.2 Hz), 6.616 (dd. 1H, J=2.3 Hz), 6.765 (d, 2H, J=2.3 Hz), 7.13–7.3 (m, 5H), 10.123 (s, 1H).

b) 3-Benzyl-5,7-dimethoxy-4-methyl-2(1H)-quinolinone

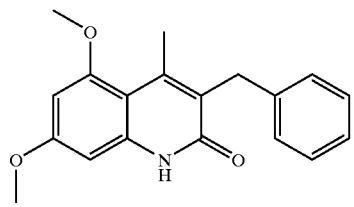

The product from the previous example (1.2 g) was added to a preheated (85° C.) methanesulfonic acid (3.5 ml) and kept at that temperature for 15 minutes. The solution was allowed to cool and then treated with ice water. The product was filtered, washed with sodium bicarbonate and water. Yield 1.08 g (95%).

$^1$-H-NMR (300 MHz):2.486 (s, 3H), 3.785 (s, 3H), 3.808 (s, 3H), 3.985 (s, 2H), 6.315 (d, 1H, J=2.4 Hz), 6.472 (d, 1H, J=2.4Hz), 7.1–7.3 (m, 5 H), 11.52 (s, 1H).

c) 3-Benzyl-5,7-dihydroxy-4-methyl-2(1H)-quinolinone

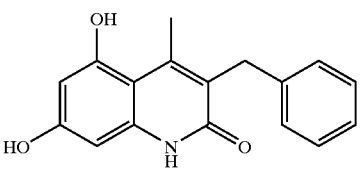

The product from the previous example (1 g) was refluxed under nitrogen in pyridine hydrochloride (5 g) for twenty minutes. The reaction mixture was treated with water and the product filtered. Yield 0.9 g (100%). Melting point: 307–312° C.

$^1$-H-NMR (300 MHz):2.503 (s, 3H), 3.942 (s, 2H), 6.102 (d, 1H, J=2.3 Hz), 6.187 (d, 1H, J=2.3 Hz), 7.1–7.25 (m, 5H), 9.725 (s, 1H), 9.984 (s, 1H), 11.285 (s, 1H).

d) 1,3-Dibenzyl-5,7-dimethoxy-4-methyl-2(1H)-quinolinone

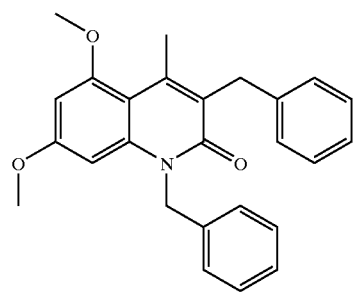

The product from the example 8b (1 g), potassium t-butoxide (0.62 g) and benzyl bromide (0.68 ml) were stirred in DMSO (10 ml) at 60° C. for 4 hours. The reaction mixture was treated with water, extracted with toluene and evaporated. The product was triturated with ethyl ether and filtered. Yield 0.5 g (39%).

$^1$-H-NMR (400 MHz):2.537 (s, 3H), 3.708 (s, 3H), 3.826 (s, 3H), 4.124 (s, 2H), 5.56 (b, 2H), 6.413–6.434 (m, 2H), 7.154–7.332 (m, 10H).

e) 1,3-Dibenzyl-5,7-dihydroxy-4-methyl-2(1H)-quinolinone.

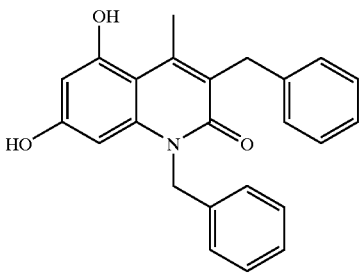

The product from the previous example (2 g) was treated with pyridine hydrochloride (10 g) as described in example 8c. The product was extracted with ethyl acetate and evaporated. Yield 1,4 g (75%).

$^1$-H-NMR (400 MHz):2.570 (s, 3H), 4.076 (s, 2H), 5.450 (b, 2H), 6.135 (d, 1H, J=2.2 Hz), 6.199 (d, 1H, J=2.2 Hz), 7.128–7.333 (m, 10 H), 9.83 (b, 1H), 10.166 (s, 1H).

f) 5,7-Bis(cyanomethoxy)-1,3-dibenzyl-4-methyl-2(1H)-quinolinone.

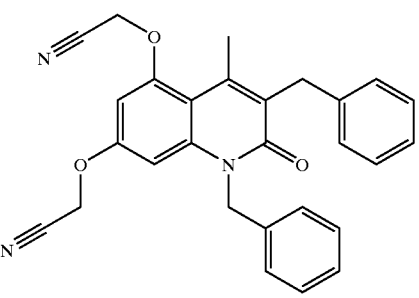

The product from the previous example (1.4 g) was treated with chloroacetonitrile (0.76 g) and K$_2$CO$_3$ (2.5 g) in DMF (20 ml) as described in example 1b. Yield 1.5 g (89%).

$^1$-H-NMR (400 MHz):2.555 (s, 3H), 4.146 (s, 2H), 5.214 (s, 2H), 5.275 (s, 2H), 5.578 (s, 2H), 6.735 (s, 2H), 7.13–7.33 (m, 10H).

g) 5,7-Bis[(1H-tetrazol-5-yl)methoxy]-1,3-dibenzyl-4-methyl-2(1H)-quinolinone.

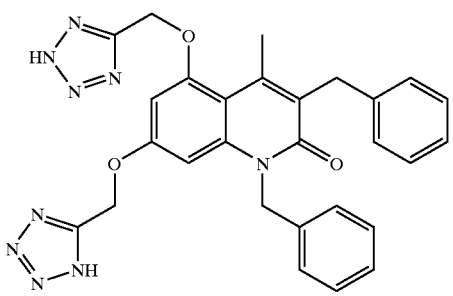

The product from the previous example (1.3 g) was treated with sodium azide (0.41 g) and ammonium chloride (0.34 g) as described in example 1c. Yield: 0.69 g (45%).

$^1$-H-NMR (400 MHz):2.471 (s, 3H), 4.113 (s, 2H), 5.477 (s, 2H), 5.55 (b, 2H), 5.574 (s, 2H), 6.670 (d, 1H, J=2.1 Hz), 6.775 (d, 1H, J=2.1 Hz), 7.13–7.32 (m, 10 H).

Example 9

Preparation of 5,7-Bis[(1H-tetrazol-5-yl)methoxy]-3-benzyl-1,4-dimethyl-2(1H)-quinolinone a) 3-Benzyl-5,7dimethoxy-1,4-dimethyl-2(1H)-quinolinone.

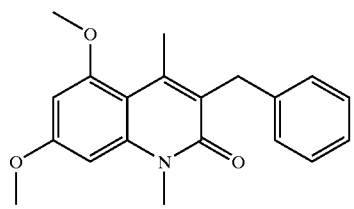

The product from example 8b (0.5 g), t-BuOK (0.2 g) and methyl iodide (0.4 ml) were stirred in DMSO (5 ml) at 35° C. for two days. The reaction mixture was treated with water and extracted with toluene. The product was purified by column chromatography using toluene-ethyl acetate-acetic acid 8:2:1 as the eluent. Yield 0.24 g(46%).

$^1$-H-NMR (300 MHz):2.51 (s, 3H), 3.632 (s, 2H), 3.846 (s, 3), 3.896 (s, 3H 4.047 (s, 2H), 6.468 (d, 1H, J=2.3 Hz), 6.558 (d, 1H, J=2.3 Hz), 7.1–7.26 (m, 5H).

b) 3-Benzyl-5,7-dihydroxy-1,4dimethyl-2(1H)-quinolinone.

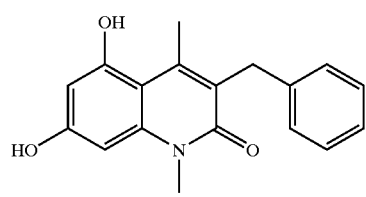

The product from the previous example (0.2 g) was treated with pyridine hydrochloride (2 g) as described in example 8c and the product extracted with ethyl acetate. Yield 0.16 g (89%).

$^1$-H-NMR (400 MHz):2.567 (s, 3H), 3.515 (s, 3H), 4.005 (s, 2H), 6.244 (d, 1H, J=2.3 Hz), 6.268 (d, 1H, J=2.3 Hz), 7.08–7.25 (m. 5H), 9.879 (s, 1H), 10.113 (s,1H).

c) 5,7-Bis(cyanomethoxy)-3-benzyl-1,4-dimethyl-2(1H)-quinolinone.

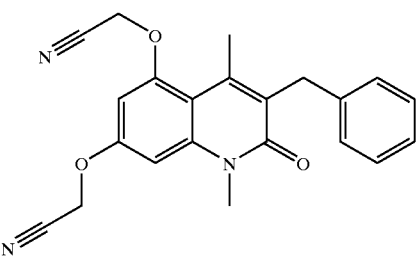

The product from the previous example (0.15 g), chloroacetonitrile 0.08 g) and K$_2$CO$_3$ (0.28 g) were reacted in DMF (2 ml) as described in example 1b. Yield 0.16 g (84%).

$^1$-H-NMR (400 MHz): 2.524 (s, 3H), 3.658 (s, 3H), 4.079 (s, 2H), 5.292 (s, 2H), 5.379 (s, 2H), 6.766 (d, 1H, J=2.3 Hz), 6.855 (d, 1H, J=2.3 Hz), 7.13–7.24 (m 5H).

d) 5,7-Bis[(1H-tetrazol-5-yl)methoxy]-3-benzyl-1,4-dimethyl-2(1H)-quinolinone.

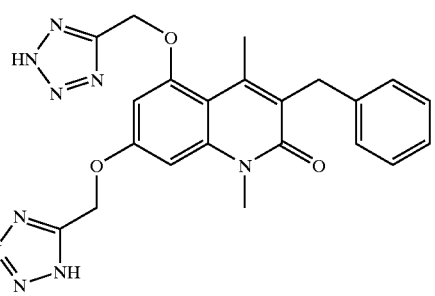

The product from the previous example (0.15 g) was treated with NaN$_3$ (57 mg) and NH$_4$Cl (47 mg) in DMF (2 ml) as described in example 1c. Yield 0.1 15 g. Melting point: 250–253° C.

$^1$-H-NMR (400 MHz): 2.451 (s, 3H), 3.649 (s, 3H), 4.042 (s, 2H), 6.792 (d, 1H, J=2.2 Hz), 6.833 (d, 1H, J=Hz), 7.1–7.25 (m, 5H).

Example 10

Preparation of 3-Benzyl-5,7-bis[(2-methyl-1H-tetrazol-5-yl)methoxy]-4-methyl-2H-1-benzopyran-2-one and the three isomers

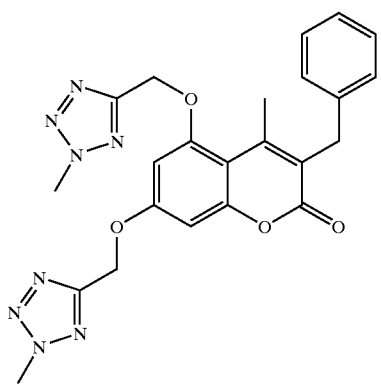

0.07 ml of methyl iodide was added to a solution of 0.2 g of the product from example 1c and 0.31 g of K$_2$CO$_3$ in 2 ml of DMF and the mixture stirred at room temperature for 4 hours. The reaction mixture was poured into ice water and filtered. Yield 0.2 g as a mixture of four regioisomers, melting point 71–76° C.

¹H-NMR (DMSO-d₆, 400 MHz): 2.47 (s, CH₃),2.48 (s, CH₃), 3.93 (s, CH₂Ph), 4.11 (s, NCH₃), 4.12 (s, NCH₃), 4.15 (s, NCH₃), 4.38 (s, NCH₃), 4.40 (s, NCH₃), 5.51 (s, OCH₂), 5.52 (s, OCH₂), 5.62 (s, OCH₂), 5.67 (s, OCH₂), 6.84–6.91 (m, 2H), 7.16–7.28 (m,5H, Ph).

Example 11

Preparation of 3-Benzyl-5,7-bis[1-(1 H-tetrazol-5-yl)ethoxy]-4-methyl-2 H -1-benzopyran-2-one, mixture of stereoisomers a) 3-Benzyl-5,7-bis-[(1-cyano)ethoxy)-4-methyl-2 H -1-benzopyran-2-one

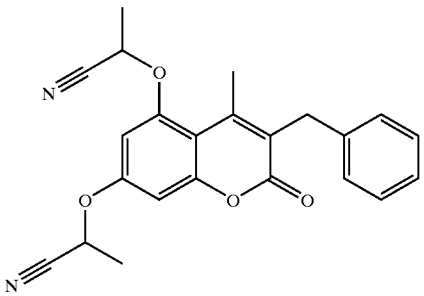

The product from example 1a (1 g), 2-chlorpropionitrile (0.7 g) and potassium carbonate (2 g) were heated in DMF (15 ml) under nitrogen at 110° C. for sixty minutes. The mixture was treated with water, filtered and washed with 1 N NaOH and water. Yield 1.2 g.

¹H-NMR (DMSO-d₆, 300 MHz): 1.74–1.78 (t+t, 6 H, CH—CH₃), 2.53 (s, 3 H), 3.97 (s, 2H), 5.58–5.66 (m, 2H, CH—CH₃), 6.87 (m, 1H), 6.99 (d, 1H), 7.18–7.31 (m, 5H).

b) 3-Benzyl-5,7-bis[1-(1 H-tetrazol-5-yl)ethoxy]4-methyl-2 H-1-benzopyran-2-one, mixture of stereoisomers.

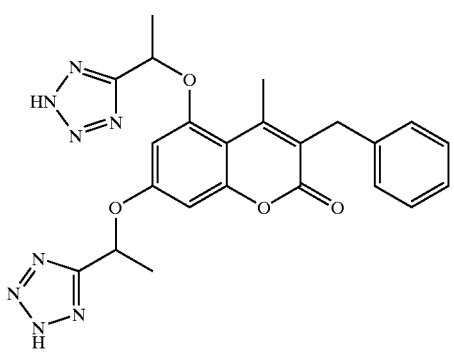

The product from the previous example (0.5 g), sodium azide (0.18 g) and ammonium chloride (0.15 g) were heated in DMF (7 ml) at 100° C. for 90 minutes. The product was treated with water, extracted with ethyl acetate and evaporated. Yield 0.57 g. Melting point 91–104° C.

¹H-NMR (DMSO-d₆, 300 MHz): 1.69–1.77 (m, 6 H, CH—CH₃), 2.54 (s, 3H), 3.94 (s, 2H), 6.10–6.17 ((m, 2H, CH—CH₃), 6.65 (dd, 1H), 6.74 (dd, 1H), 7.13–7.30 (m, 5H).

Example 12

Preparation of 5,7-Bis(carboxymethoxy)-1,3-dibenzyl-4-methyl-2(1H)-quinolinone

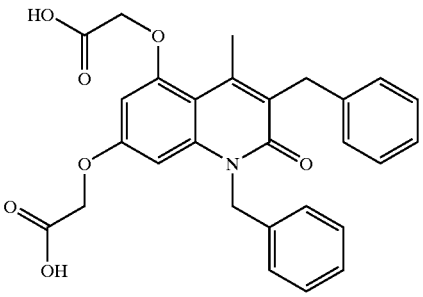

The product from example 8f (0.2 g) was refluxed in a solution of concentrated hydrochloric acid (3 ml) and acetic acid (2 ml) for one hour. The product was filtered at 25° C. Yield 0.14 g.

¹H-NMR (300 Mhz, DMSO-d₆): 2.63 (s, CH₃), 4.14 (s, 2H, CH₂Ph), 4.66 (s, 2 H, OCH₂COOH), 4.79 (s, 2H, OCH₂COOH), 5.53 (s, 2H, NCH₂Ph), 6.41 (d, 1H, J=2.2 Hz), 6.45 (d, 1H, J=2.2 Hz), 7.13–7.34 (m, 10 H, Ph).

Example 13

Preparation of 3-Benzyl-5,7-bis[(1H-tetrazol-5-yl)methoxy]-1-(4-fluorobenzyl)-4-methyl-2(1H)-quinolinone a) 1-Benzyl-5,7dimethoxy-3-(4-fluorobenzyl)-4-methyl-2(1H)-quinolinone

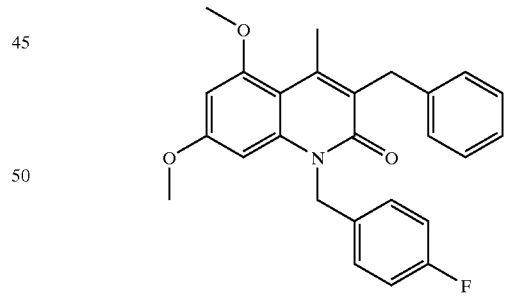

The product from example 8b (2 g), potassium -tert-butoxide (0.87 g) and 4-fluorobenzylchloride (1.12 g) were heated in DMSO (20 ml) at 60° C. for three hours as in example 8d. Yield 1.28 g.

¹H-NMR (400 Mhz, DMSO-d₆): 2.53 (s, 3H), 3.73 (s, 3H), 3.83 (s, 3H), 5.55 (s, 2H), 6.43 (s, 2H), 7.12–7.2 (m, 5 H), 7.26–7.28 (m, 4H).

b) 3-Benzyl-5,7-dihydroxy-1-(4-fluorobenzyl)-4-methyl-2 (1H)-quinolinone

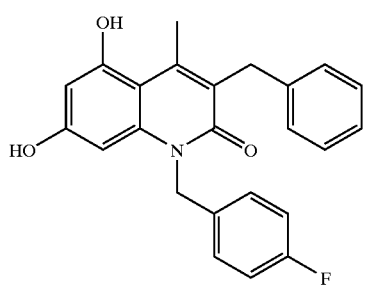

The product from previous example (1.25 g) were heated in pyridine hydrochloride (12.5 g) at about 225° C. for 9 minutes. Yield 1 g.

$^1$H-NMR (300 Mhz, DMSO-d$_6$): 2.56 (s, 3H), 4.07 (s, 2H), 5.4 (b, 2H), 6.13 (d, 1H, J=2.1 Hz), 6.20 (d, 1H, J=2.1 Hz), 7.12–7.28 (m, 9H), 9.88 (s, 1H), 10.22 (s, 1H).

c) 3-Benzyl-5,7-Bis(cyanomethoxy)-1-(4-fluorobenzyl)-1-(4-methyl-2(1H)-quinolinone

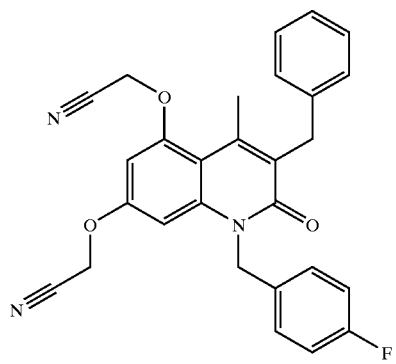

The product from the previous example (1 g), ClCH$_2$CN (0.43 g) and K$_2$CO3 (1.42 g) were heated in DMF (8 ml) at 120° C. for one hour. Yield 0.94 g.

$^1$H-NMR (300 Mhz, DMSO-d$_6$): 2.55 (s, 3H), 4.14 (s, 2H), 5.25 (s, 2H), 5.28 (s, 2H), 5.57 (s, 2H), 6.74 (s, 2H, ArH), 7.1–7.3 (m, 9H).

d) 3-Benzyl-5,7-bis[(1H-tetrazol-5-yl)methoxy]-1-(4fluorobenzyl)-4-methyl-2(1H)-quinolinone

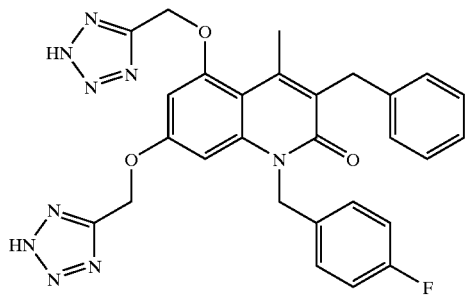

The product from the previous example (0.5 g), sodium azide (0.14 g) and ammonium chloride (0.12 g) were heated in DMF (5 ml) at 120° C. for 90 min. The product was triturated with acetonitrile. Yield 0.28 g. Melting point: 126–132° C.

$^1$H-NMR (300 Mhz, DMSO-d$_6$): 2.48 (s, 3H), 4.11 (s, 2H), 5.51 (s, 2H), 5.55 (s, 2H), 5.58 (s, 2H), 6.67 (d, 1H, J=2.1 Hz), 6.78 (d, 1H, J=2.1 Hz).

Example 14

Preparation of 5,7-Bis[(1H-tetrazol-5-yl)methoxy]-3-(4-chlorobenzyl)-4-methyl-2H-1-benzopyran-2-one a) 3-(4-Chlorobenzyl)-5,7-dihydroxy-4-methyl-2H-1-benzopyran-2-one

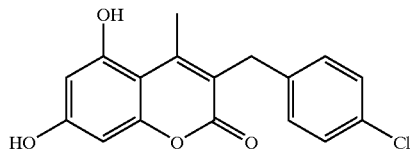

A solution of phloroglucinol (1.57 g) and ethyl 2-(4-chlorobenzyl)-acetoacetate (3.18 g) in ethanol (25 ml) was treated with dry HCl at 0° C. for 1.5 hours and the solution was kept at that temperature overnight. Solvent was evaporated and the precipitate triturated with water. Yield 3.87 g (98%). Melting point 270–278° C.

$^1$H-NMR (DMSO-d$_6$, 300 MHz): 2.52 (s, 3H, CH$_3$), 3.87 (s, 2H, CH$_2$), 6.17 (d, 1H, J=2.4 Hz), 6.28 (d, 1H, J=2.4 Hz), 7.18–7.34 (m, 4H, Ph), 10.21 (s, 1H, OH), 10.48 (s, 1H, OH).

b) 5,7-Bis(cyanomethoxy)-3-(4-chlorobenzyl)-4-methyl-2H-1-benzopyran-2-one

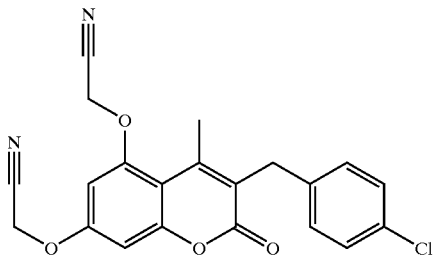

The product from the previous example (1.00 g), chloroacetonitrile (0.50 g) and potassium carbonate (2.18 g) were heated in DMF (5 ml) at 100° C. for 30 minutes. The product was isolated as described in example 1b. Yield 0.90 g (72%).

$^1$H-NMR (DMSO-d$_6$, 300 MHz): 2.52 (s, 3H, CH$_3$), 3.95 (s, 2H, CH$_2$), 5.308 (s, 2H, OCH$_2$CN), 5.312 (s, 2H, OCH$_2$CN), 6.81 (d, 1H, J=2.5 Hz), 6.94 (d, 1H, J=2.5 Hz), 7.22–7.33 (m, 4H, Ph).

c) 5,7-Bis[(1H-tetrazol-5-yl)methoxy]-3-(4-chlorobenzyl)-4-methyl-2H-1-benzopyran-2-one

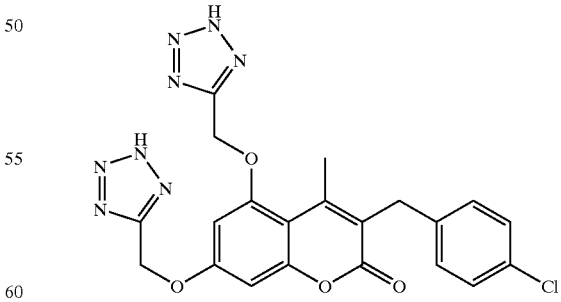

The product from the previous example (0.40 g), sodium azide (0.14 g) and ammonium chloride (0.11 g) were heated in DMF (2 ml) at 100° C. for 2 hours. The product was isolated as in example 1c. Yield 0.40 g (82%).

$^1$H-NMR (DMSO-d$_6$, 300 MHz): 2.46 (s, 3H, CH$_3$), 3.92 (s, 2H, CH$_2$), 5.602 (s, 2H, OCH$_2$Tet), 5.609 (s, 2H,

OCH₂Tet), 6.83 (d, 1H, J=2.5 Hz), 6.85 (d, 1H, J=2.5 Hz), 7.20–7.33 (m, 4H, Ph).

Example 15

Preparation of 5,7-Bis[(1H-tetrazol-5-yl)methoxy]-3-(4-nitrobenzyl)-4-methyl-2H-1-benzopyran-2-one a) 5,7-Dihydroxy-4-methyl-3-(4-nitrobenzyl)-2H-1-benzopyran-2-one

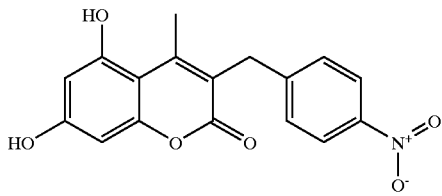

A solution of phloroglucinol (0.48 g) and ethyl 2-(4-nitrobenzyl)aceto-acetate (1.00 g) in ethanol (150 ml) was treated with dry HCl at 0° C. for 7.5 hours and the solution was kept at that temperature overnight. Solvent was evaporated and the precipitate triturated with water. Yield 0.63 g (51%). Melting point 280–285° C.

¹H-NMR (DMSO-d₆, 300 MHz): 2.53 (s, 3H, CH₃), 4.03 (s, 2H, CH₂), 6.19 (d, 1H, J=2.4 Hz), 6.29 (d, 1H, J=2.4 Hz), 7.40–7.51 and 8.11–8.17 (m, 4 H, Ph), 10.25 (s, 1H, OH), 10.52 (s, 1H, OH).

b) 5,7-Bis(cyanomethoxy)-3-(4-nitrobenzyl)-4-methyl-2H-1-benzopyran-2-one

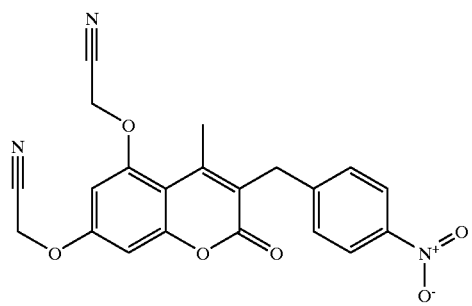

The product from the previous example (0.57 g), chloroacetonitrile (0.27 g) and potassium carbonate (1.20 g) were heated in DMF (2 ml) at 100° C. for 50 minutes. The product was isolated as described in example 1b. Yield 0.47 g (67%). Melting point 178–185° C.

¹H-NMR (DMSO-d₆, 400 MHz): 2.53 (s, 3H, CH₃), 4.11 (s, 2H, CH₂), 5.319 (s, 2H, OCH₂CN), 5.323 (s, 2H, OCH₂CN), 6.83 (d, 1H, J=2.4 Hz), 6.96 (d, 1H, J=2.4 Hz), 7.48–7.53 and 8.12–8.16 (m, 4H, Ph).

c) 5,7-Bis[(1H-tetrazol-5-yl)methoxy]-3-(4-nitrobenzyl)-4-methyl-2H-1-benzopyran-2-one

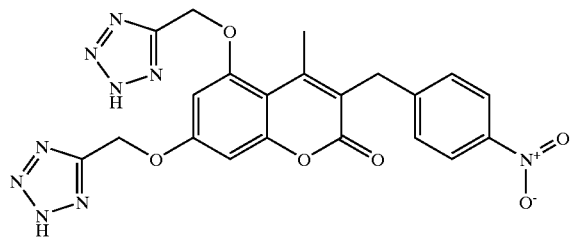

The product from the previous example (0.38 g), sodium azide (0.12 g) and ammonium chloride (0.11 g) were heated in DMF (3 ml) at 100° C. for 2 hours. The product was isolated as described in example 1c. Yield 0.25 g (54%). Melting point 240–244° C.

¹H-NMR (DMSO-d₆, 400 MHz): 2.47 (s, 3H, CH₃), 4.08 (s, 2H, CH₂), 5.611 (s, 2H, OCH₂Tet), 5.623 (s, 2H, OCH₂Tet), 6.85 (d, 1H, J=2.4 Hz), 6.87 (d, 1H, J=2.4 Hz), 7.46–7.50 and 8.12–8.16 (m, 4H, Ph).

Example 16

Preparation of 5,7-Bis[(1H-tetrazol-5-yl)methoxy]-3-cyclopentyl-4-methyl-2H-1-benzopyran-2-one a) 3-Cyclopentyl-5,7-dihydroxy-4-methyl-2H-1-benzopyran-2-one

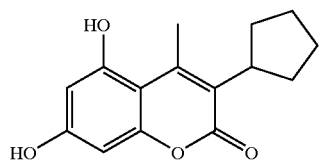

A solution of phloroglucinol (2.00 g) and ethyl 2-cyclopentylaceto-acetate (3.14 g) in ethanol (40 ml) was treated with dry HCl at 0° C. for 2.5 hours and the solution kept at that temperature overnight. Solvent was evaporated and the precipitate purified with flash chromatography eluting with toluene-EtOAc-AcOH (8:1:1). Yield 1.22 g (29

¹H-NMR (DMSO-46, 300 MHz): 1.50–1.88 (m, 8H, —(CH₂)₄—), 2.57 (s, 3H, CH₃), 3.25 (m, 1H, CH), 6.11 (d, 1H, J=2.4 Hz), 6.25 (d, 1H, J=2.4 Hz), 10.25 (b, 2H, OH).

b) 5,7-Bis(cyanomethoxy)-3-cyclopentyl-4-methyl-2H-1-benzopyran-2-one

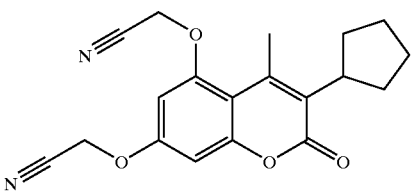

The product from the previous example (0.50 g), chloroacetonitrile (0.31 g) and potassium carbonate (0.61 g) were heated in DMF (2 ml) at 80° C. for 40 minutes. The product was isolated as described in example 1b. Yield 0.56 g (86%).

¹H-NMR (DMSO-d₆, 300 MHz): 1.55–1.90 (m, 8H, —(CH₂)₄—), 2.56 (s, 3H, CH₃), 3.37 (m, 1H, CH), 5.29 (s, 2H, OCH₂CN), 5.31 (s, 2H, OCH₂CN), 6.75 (d, 1H, J=2.5 Hz), 6.88 (d, 1H, J=2.5 Hz).

c) 5,7-Bis[(1H-tetrazol-5-yl)methoxy]-3-cyclopentyl-4-methyl-2H-1-benzopyran-2-one

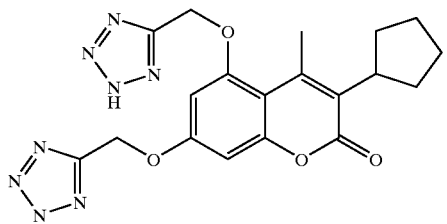

The product from the previous example (0.30 g), sodium azide (0.13 g) and ammonium chloride (0.11 g) were heated in DMF (1 ml) at 100° C. for 1.5 hours. The product was isolated as described in example 1c. Yield 0.30 g (80%). Melting point 248–252° C.

$^1$H-NMR (DMSO-d$_6$, 400 MHz): 1.53–1.89 (m, 8H, —(CH$_2$)$_4$—), 2.51 (s, 3H, CH$_3$), 3.34 (m, 1H, CH), 5.59 (s, 2H, OCH$_2$Tet), 5.61 (s, 2H, OCH$_2$Tet), 6.80 (s, 2H).

Example 17

Preparation of 5,7-Bis[(1H-tetrazol-5-yl)methoxy]-4-methyl-3-(1-naphtylmethyl)-2H-1-benzopyran-2-one a) 5,7-dihydroxy-4-methyl-3-(1-naphtylmethyl)-2H-1-benzopyran-2-one

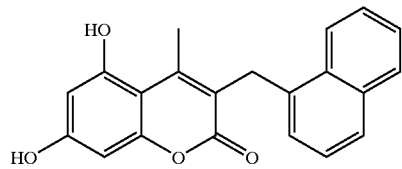

A solution of phloroglucinol (0.47 g) and ethyl 2-(1-naphtylmethyl)-acetoacetate (1.00 g) in ethanol (20 ml) was treated with dry HCl at 0° C. for 3 hours and the solution kept at that temperature overnight. Solvent was evaporated and the precipitate triturated with water and recrystallized from isopropanol-water (1:1). Yield 0,96 g (78%). Melting point 275–280° C.

$^1$H-NMR (DMSO-d$_6$, 400 MHz): 2.45 (s, 3H, CH$_3$), 4.32 (s, 2H, CH$_2$), 6.23 (d, 1H, J=2.5 Hz), 6.32 (d, 1H, J=2.5 Hz), 6.97–8.25 (m, 7H, Naph), 10.26 (s, 1H, OH), 10.53 (s, 1H, OH).

b) 5,7-Bis(cyanomethoxy)-4-methyl-3-(1-naphtylmethyl)-2H-1-benzopyran-2-one

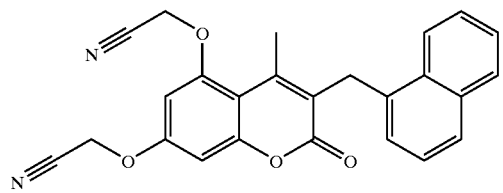

The product from the previous example (0.80 g), chloroacetonitrile (0.36 g) and potassium carbonate (0.66 g) were heated in DMF (4 ml) at 100° C. for 1 hour. The product was isolated as in example 1b. Yield 0.30 g (30%).

$^1$H-NMR (DMSO-d$_6$, 300 MHz): 2.45 (s, 3H, CH$_3$), 4.40 (s, 2H, CH$_2$), 5.34 (s, 2H, OCH$_2$CN), 5.36 (s, 2H, OCH$_2$CN), 6.86 (d, 1H, J=2.5 Hz), 7.010 (d, 1H, J=2.5 Hz), 7.016–8.27 (m, 7H, Naph).

c) 5,7-Bis[(1H-tetrazol-5-yl)methoxy]-4-methyl-3-(1-naphtylmethyl)-2H 1-benzopyran-2-one

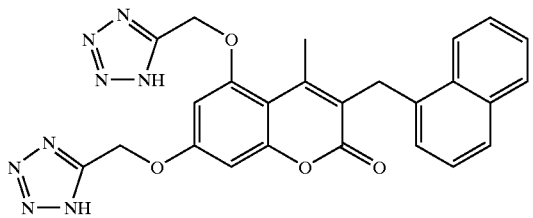

The product from the previous example (0.25 g), sodium azide (0.080 g) and ammonium chloride (0.072 g) were heated in DMF (2 ml) at 100° C. for 2.5 hours. The product was isolated as described in example 1c. Yield 0.11 g (36%). Melting point 164–174° C.

$^1$H-NMR (DMSO-d$_6$, 300 MHz): 2.40 (s, 3H, CH$_3$), 4.37 (s, 2H, CH$_2$), 5.63 (s, 2H, OCH$_2$Tet), 5.65 (s, 2H, OCH$_2$Tet), 6.87 (d, 1H, J=2.5 Hz), 6.92 (d, 1H, J=2.5 Hz), 6.98–8.26 (m, 7H, Naph).

Example 18

Preparation of 1-Benzyl-5,7-bis-[(1H-tetrazol-5-yl)-methoxy]-4-methyl-2(1H)-quinolinone a) 5,7-Dimethoxy-4-methyl-2(1H)-quinolinone

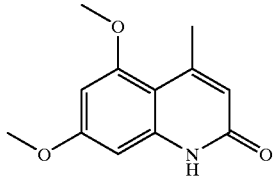

tert-Butyl acetoacetate (1.58 g) was heated to 120° C. and 3,5-dimethoxyaniline (1.53 g) dissolved in xylene (4 ml) was added The mixture was heated at 120–130° C. for 20 minutes and then cooled to room temperature. Methanesulfonic acid (2 ml) was added and the mixture was stirred at ambient temperature for 10 minutes. Water (40 ml) was added and the precipitate filtered and dried. Yield 1.31 g (60%).

$^1$H-NMR (DMSO-d$_6$, 300 MHz): 2.50 (s, 3H, CH$_3$), 3.79 (s, 3H, OCH$_3$), 3.83 (s, 3H, OCH$_3$), 6.03 (s, 1H, CH=C), 6.31 (d, 1H, J=2.3 Hz), 6.45 (d, 1H, J=2.3 Hz), 11.4 (b, 1H, NH).

b) 1-Benzyl-5,7-dimethoxy-4-methyl-2(1H)-quinolinone

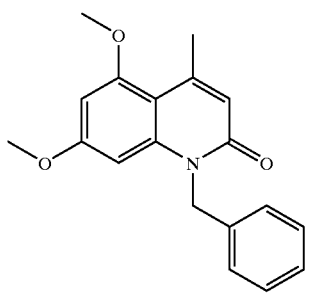

The product from the previous example (1.20 g) was suspended to DMSO (15 ml) and t-BuOK (0.68 g) and benzylbromide (1.03 g) were added. Reaction mixture was stirred at ambient temperature overnight. Water was added and the product extracted to EtOAc. EtOAc was dried and evaporated to dryness. The product was recrystallized from toluene. Yield 0.80 g (47%).

$^1$H-NMR (DMSO-d$_6$, 300 MHz): 2.55 (d, 3H, J=1.1 Hz, CH$_3$), 3.71 (s, 3H, OCH$_3$), 3.84 (s, 3H, OCH$_3$), 5.48 (b, 2H, NCH$_2$), 6.29 (d, 1H, J=1.1 Hz, CH=C), 6.4 (s, 2H), 7.18–7.33 (m, 5H, Ph).

c) 1-Benzyl-5,7-dihydroxyy-4-methyl-2(1H)-quinolinone

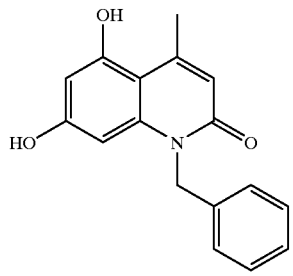

The product from the previous example (0.69 g) was dissolved to CH$_2$Cl$_2$ (14 ml) and the reaction mixture cooled to −20° C. BBr$_3$ (2.4 g) in CH$_2$Cl$_2$ (1M solution) was added and the mixture was allowed to warm to ambient temperature during the night. The precipitate was filtered, washed with CH$_2$Cl$_2$ and dissolved to EtOAc. EtOAc was washed with dilute HCl, dryed and evapotated to dryness. Yield 0.34 g (54%)

1H-NMR (DMSO-d$_6$, 300 MHz): 2.56 (d, 3H, J=1.0 Hz, CH$_3$), 5.33 (b, 2H, NCH$_2$), 6.11 (d, 1H, J=2.1 Hz), 6.13 (d, 1H, J=1.0 Hz, CH=C), 6.17 (d, 1H, J=2.1 Hz), 7.12–7.34 (m, 5H, Ph), 9.90 (b, 1H, OH), 10.22 (s, 1H, OH).

d) 1-Benzyl-5,7-bis(cyanomethoxy)-4-methyl-2(1H)-quinolinone

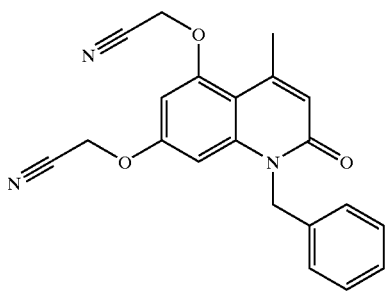

The product from the previous example (0.34 g), chloroacetonitrile (0.13 g) and potassium carbonate (0.34 g) were heated in DMF (2 ml) at 100° C. for 1.5 hours. Water was added and the precipitate filtered and dried. The product was recrystallized from isopropanol. Yield 0.20 g (46%).

$^1$H-NMR (DMSO-d$_6$, 400 MHz): 2.57 (s, 3H, CH$_3$), 5.22 (s, 2H, OCH$_2$CN), 5.30 (s, 2H, OCH$_2$CN), 5.50 (b, 2H, NCH$_2$), 6.42 (s, 1H, CH=C), 6.70 (d, 1H, J=2.1 Hz), 6.73 (d, 1H, J=2.1 Hz), 7.21–7.32 (m, 5H, Ph).

e) 1-Benzyl-5,7-bis-[(1H-tetrazol-5-yl)methoxy]-4-methyl-2(1H)-quinolinone

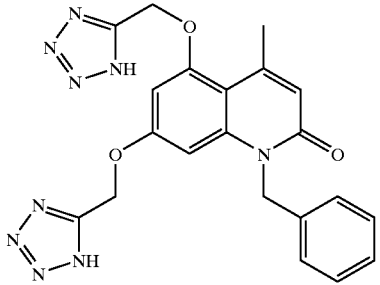

The product from the previous example (0.20 g), sodium azide (0.072 g) and ammonium chloride (0.060 g) were heated in DMF (2 ml) at 100° C. for 3 hours. The product was isolated as described in example 1c. Yield 0.21 g (85%). Melting point 246–249° C.

$^1$H-NMR (DMSO-d$_6$, 400 MHz): 2.50 (s, 3H, CH$_3$), 5.48 (b, 4H, OCH$_2$Tet, NCH$_2$),5.60 (s, 2H, OCH$_2$Tet), 6.34 (s, 1H, CH=C), 6.64 (d, 1H, J=1.9 Hz), 6.77 (d, 1H, J=1.9 Hz), 7.18–7.32 (m, 5H, Ph).

Example 19

Preparation of 1-Benzyl-5,7-bis[(1H-tetrazol-5-yl)methoxy]-3-(2-fluorobenzyl)-4-methyl-2(1H)-quinolinone a) 5,7-Dimethoxy-3-(2-fluorobenzyl)-4-methyl-2(1H)-quinolinone

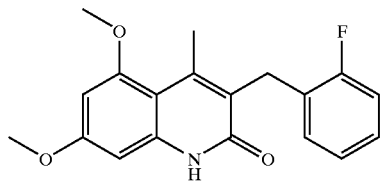

Ethyl 2-(2-fluorobenzyl)acetoacetate (2.5 g) in xylene (1 ml) was heated to 150° C. and 3,5-dimethoxyaniline (1.46 g) in xylene (4 ml) was added in small portions during 30 minutes. The reaction mixture was heated at 160° C. for 3 hours and then cooled to room temperature. Methanesulfonic acid (1.7 ml) was added and the mixture was stirred at ambient temperature for 30 minutes. Water was added and the precipitate filtered and dried. The product was triturated with warm ethanol. Yield 0.64 g (21%).

$^1$H-NMR (DMSO-d$_6$, 300 MHz): 2.45 (s, 3H), 3.79 (s, 3H), 3.82 (s, 3H), 3.97 (s, 2H), 6.33 (d, 1H, J=2.4 Hz), 6.48 (d, 1H, J=2.4 Hz), 6.90–7.25 (m, 4H), 11.61 (s, 1H).

b) 1-Benzyl-5,7-dimethoxy-3-(2-fluorobenzyl)-4-methyl-2(1H)-quinolinone

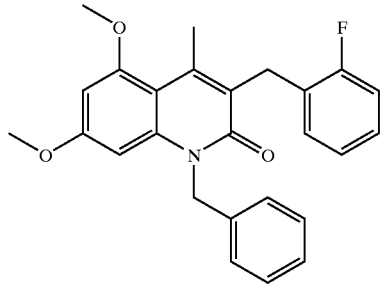

The product from the previous example (0.62 g) was treated with t-BuOK (0.23 g) and benzylbromide (0.36 g) in DMSO (12 ml) at 60° C. for 2.5 hours. The product was isolated as described in example 18b. Yield 0.39 g (49%).

1H-NMR (DMSO-d$_6$, 400 MHz): 2.51 (s, 3H), 3.72 (s, 3H), 3.84 (s, 3H), 4.11 (s, 2H), 5.55 (b, 2H), 6.433 (d, 1H, J=2.1 Hz), 6.443 (d, 1H, J=2.1 Hz), 6.97–7.33 (m, 9H).

c) 1-Benzyl-5,7-dihydroxy-3-(2-fluorobenzyl)-4-methyl-2(1H)-quinolinone

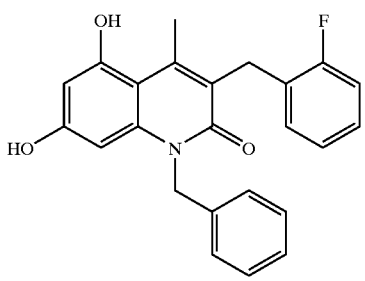

The product from the previous example (0.34 g) was treated with BBr$_3$ (8.48 g) in CH$_2$Cl$_2$ (7 ml) as described in example 18c. Yield 0.30 g (82%).

$^1$H-NMR (DMSO-d$_6$, 400 MHz): 2.55 (s, 3H), 4.06 (s, 2H), 5.40 (b, 2H), 6.13 (d, 1H, J=2.1 Hz), 6.22 (d, 1H, J=2.1 Hz), 6.97–7.33 (m, 9H), 10.3 (b, 2H).

d) 1-Benzyl-5,7-bis(cyanomethoxy)-3-(2-fluorobenzyl)-4-methyl-2(11H)-quinolinone

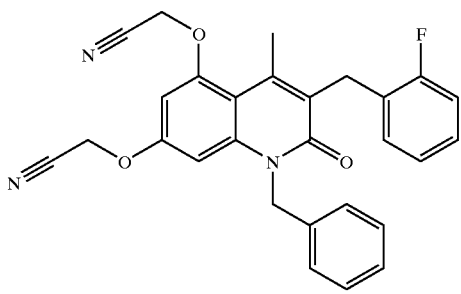

The product from the previous example (0.21 g), chloroacetonitrile (0.086 g) and potassium carbonate (0.37 g) were heated in DMF (2 ml) at 100° C. for 2 hours. The product was isolated as described in example 1b. Yield 0.18 g (71%).

$^1$H-NMR (DMSO-d$_6$, 400 MHz): 2.53 (s, 3H), 4.13 (s, 2H), 5.23 (s, 2H), 5.29 (s, 2H), 5.57 (b, 2H), 6.746 (d, 1H, J=2.3 Hz), 6.756 (d, 1H, J=2.3 Hz), 7.00–7.32 (m, 9H).

e) 1-Benzyl-5,7-bis[1H-tetrazol-5-yl)methoxy]-3-(2-fluorobenzyl)-4-methyl-2(1H)-quinolinone

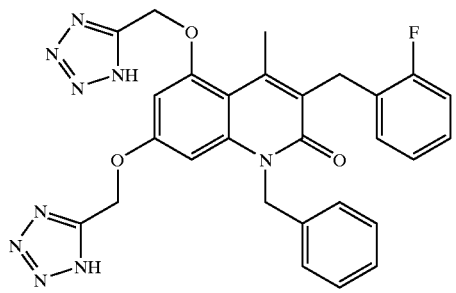

The product from the previous example (0.17 g), sodium azide (0.051 g) and ammonium chloride (0.042 g) were heated in DMF at 100° C. for 3 hours. The product was isolated as described in example 1c. Yield 0.17 g (85%). Melting point 135–140° C.

$^1$H-NMR (DMSO-d$_6$, 400 MHz): 2.46 (s, 3H), 4.10 (s, 2H), 5.48 (s, 2H), 5.51 (b, 2H), 5.59 (s, 2H), 6.68 (d, 1H, J=2.2 Hz), 6.79 (d, 1H, J=2.2 Hz), 6.99–7.32 (m, 9H).

Example 20

Preparation of 1-Benzyl-5,7-bis[1H-tetrazol-5-yl)-methoxy]-4-methyl-3-(2-phenylethyl)-2-(1H)-quinolinone a) 5,7-Dimethoxy-4-methyl-3-(2-phenylethyl)-2(1H)-quinolinone

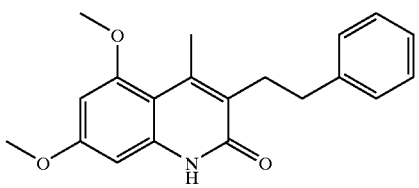

Ethyl 2-(2-phenylethyl)acetoacetate (2.70 g) in xylene (5 ml) was treated with 3,5-dimethoxyaniline (1.60 g) at 150° C. as described in example 19a. Methanesulfonic acid (4.0 ml) was added at room temperature and the mixture heated at 80° C. for 1 hour. The product was isolated as described in example 19a. Yield 1.38 g (41%).

$^1$H-NMR (DMSO-d$_6$, 400 MHz): 2.45 (s, 3H), 2.64–2.68 (m, 2H), 2.82–2.86 (m, 2H), 3.78 (s, 3H), 3.81 (s, 3H), 6.30 (d, 1H, J=2.3 Hz), 6.45 (d, 1H, J=2.3 Hz), 7.18–7.30 (m, 5H), 11.45 (s, 1H).

b) 1-Benzyl-5,7-dimethoxy-4-methyl-3-(2-phenylethyl)-2(1H)-quinolinone

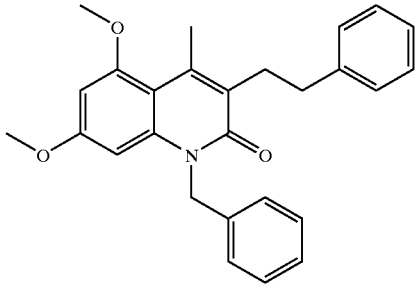

The product from the previous example (0.61 g), t-BuOK (0.24 g) and benzylbromide (0.36 g) were heated in DMSO (12 ml) at 60° C. for 2 hours. The product was isolated as described in example 18b. Yield 0.31 g (40%).

$^1$H-NMR (DMSO-d$_6$, 400 MHz): 2.51 (s, 3H), 2.73–2.77 (m, 2H), 2.96–3.00 (m, 2H), 3.70 (s, 3H), 3.83 (s, 3H), 5.55 (b, 2H), 6.40 (s, 2H), 7.17–7.33 (m, 10 H).

c) 1-Benzyl-5,7-dihydroxy-4-methyl-3-(2-phenylethyl)-2(1H)-quinolinone

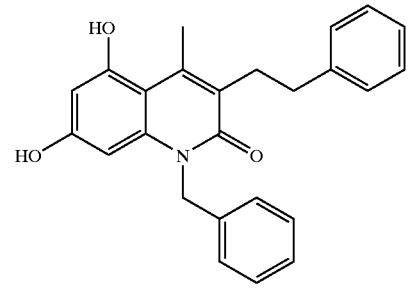

The product from the previous example (0.31 g) was treated with BBr$_3$ (0.75 g) in CH$_2$Cl$_2$ (5 ml) as in example 18c. Yield 0.26 g (89%).

¹H-NMR (DMSO-d₆, 300 MHz): 2.56 (s, 3H), 2.69–2.75 (m, 2H), 2.90–2.95 (m, 2H), 5.39 (b, 2H), 6.08 (d, 1H, J=2.0 Hz), 6.19 (d, 1H, J=2.0 Hz), 7.11–7.33 (m, 10H), 10.2 (b, 2H).

d) 1-Benzyl-5,7-bis(cyanomethoxy)-4-methyl-3-(2-phenylethyl)-2(1H-quinolinone

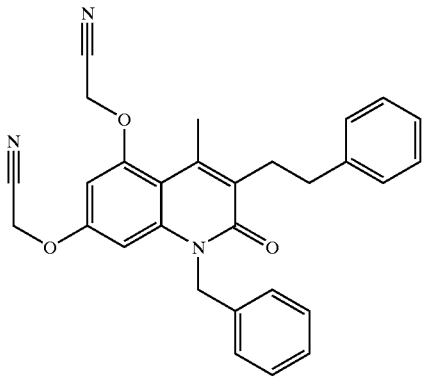

The product from the previous example (0.22 g), chloroacetonitrile (0.091 g) and potassium carbonate (0.39 g) were heated at 100° C. for 2 hours. The product was isolated as in example 1b. Yield 0.20 g (76%).

¹H-NMR (DMSO-d₆, 400 MHz): 2.50 (s, 3H), 2.73–2.77 (m, 2H), 2.98–3.02 (m, 2H), 5.21 (s, 2H), 5.29 (s, 2H), 5.56 (b, 2H), 6.70 (d, 1H, J=2.1 Hz), 6.72 (d, 1H, J=2.1 Hz), 7.18–7.33 (m, 10H).

e) 1-Benzyl-5,7-bis[1H-tetrazaol-5-yl)methoxy]-4-methyl-3-(2-phenylethyl)-2(1H)-quinolinone

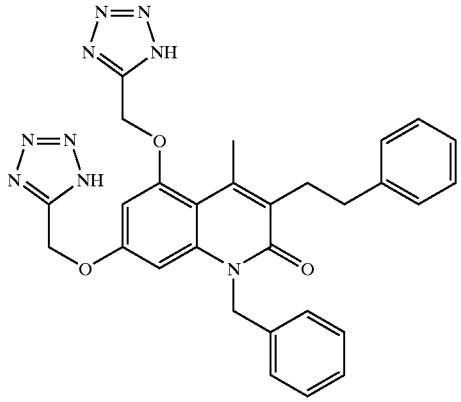

The product from the previous example (0.19 g), sodium azide (0.057 g) and ammonium chloride (0.047 g) were heated in DMF at 100° C. for 3 hours. The product was isolated as described in example 1c. Yield 0.18 g (78%). Melting point 215–218° C.

¹H-NMR (DMSO-d₆, 400 MHz): 2.46 (s, 3H), 2.70–2.74 (m, 2H), 2.95–2.99 (m, 2H), 5.47 (s, 2H), 5.54 (b, 2H), 5.57 (s, 2H), 6.64 (d, 1H, J=2.0 Hz), 6.77 (d, 1H, J=2.0 Hz), 7.16–7.33 (m, 10H).

Example 21

Preparation of 5,7-Bis(aminocarbonylmethoxy)-1,3-dibenzyl-4-methyl-2(1H)-quinolinone

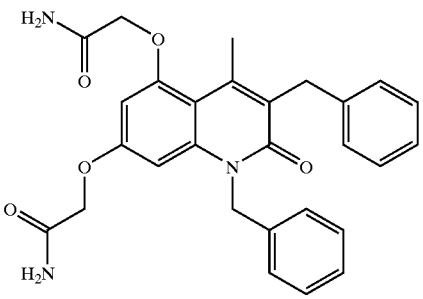

The mixture of 5,7-dihydroxy-1,3-dibenzyl-4-methyl-2 (1H)-quinolinone (0.5 g), potassium carbonate (0.9 g) and 2-chloroacetamide (0.25 g) in DMF (6.5 ml) were reacted at 100° C. for two hours. The reaction mixture was treated with ice water and filtered. The product was triturated with hot ethanol. Yield: 0.32 g. Melting point 252–253° C.

¹H-NMR (400 MHz, DMSO-d₆): 2.63 (s, 3H, CH₃), 4.13 (s, 2H, PhCH₂), 4.37 (s, 2H, OCH₂), 4.55 (s, 2H, OCH₂), 5.54 (s, 2H, NCH₂Ph), 6.40 (d, 1H, J=2 Hz, ArH), 6.53 (d, 1H, J=2 Hz, ArH), 7.13–7.33 (m, 10 H, Ph), 7.44 (d, 2H, J=65 Hz, CONH₂), 7.47 (d, 2H, J=68 Hz, CONH₂).

Example 22

Preparation of 5,7-Bis(ethoxycarbonylmethoxy)-1,3-dibenzyl-4-methyl-2(1H)-quinolinone

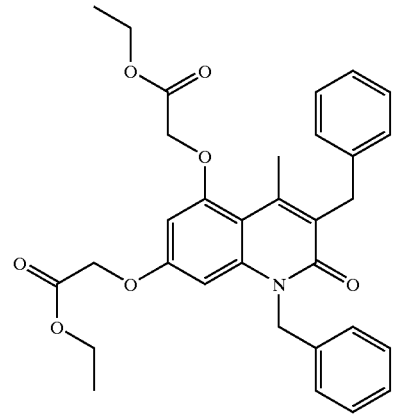

The mixture of 5,7-dihydroxy-1,3-dibenzyl-4-methyl-2 (1H)-quinolinone (1 g), ethyl 2-bromoacetate (0.63 ml) and potassium carbonate (1.49 g) in DMF (5 ml) was heated under nitrogen at 110° C. for three hours, poured into ice water and filtered. The resulting solid material was triturated with ether and filtered again. Yield: 1.03 g, melting point 113–116° C.

¹H-NMR (400 MHz, DMSO-d₆): 1.15 (t, 3H, CH₃CH₂, J=7.1 Hz), 1.20 (t, 3H, CH₃CH₂, J=7.1 Hz), 2.63 (s, 3H, CH₃), 4.03 (q, 2H, CH₂CH₃, J=7.1 Hz), 4.13 (s, 2H, CH₂Ph), 4.17 (q, 2H, CH₂CH₃, J=7.1 Hz), 4.78 (s, 2H, OCH₂), 4.90 (s, 2H, OCH₂), 6.41 (d, 1H, J=2.2 Hz), 6.44 (d, 1H, J=2.2 Hz), 7.13–7.33 (m, 10 H, Ph).

Example 23

Preparation of 5,7-Bis (hydroxyaminocarbonylmethoxy)-1,3-dibenzyl-4-methyl-2(1H)-quinolinone

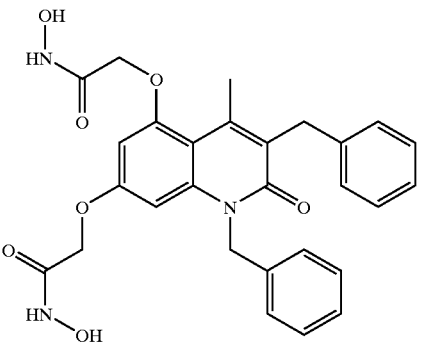

The product from the previous example (0.3 g), hydroxylamine hydrochloride (0.32 g) and 5 N NaOH (1.05 ml) were reacted in ethanol (8 ml) at 50° C. for six hours. The reaction mixture was treated with water and made basic (pH 10) and filtered. The filtrate was acidified to pH 2 and filtered. Yield: 0.2 g, melting point 121–127° C.

$^1$H-NMR (400 MHz, DMSO-$d_6$): the tautomeric forms of hydroxamic acid are seen in OCH$_2$-signals: 2.63 (s,3H, CH$_3$), 4.13 (S, 2H, CH$_2$Ph), 4.41 (s, 2H, OCH$_2$), 4.54 (s, 2H,OCH$_2$), 4.64 (s, 2H, HON=C(OH)CH$_2$O), 4.65 (s, 2H, HON=C(OH)CH$_2$O), 4.77 (s, 2H, HON=C(OH)CH$_2$O), 4.78 ((s, 2H, HON=C(OH)CH$_2$O), 5.54 (s, 2H, NCH$_2$Ph), 6.38–6.54 (m, 2H, ArH), 7.14–7.34 (m, 10 H, Ph), 9.05 (b, 2H, NOH), 10.84 (s, 1H, HONHCO), 10.88 (s, 1H, HONHCO).

EXAMPLE 5

Design of PLB Inhibitors

The three dimensional structure determined for phospholamban can be used as a target for selecting compounds that bind to the protein. In order to have good affinity for phospholamban, the ligand should have steric and electrostatic complementarity with the target. Especially, good electrostatic and/or hydrogen bonding interactions should be formed with the sites S1 and S2, and good hydrophobic interactions should be formed with the sites S3 and S4. Any of the various computer programs and databases available for such purpose can be used to design compounds that fullfill these requirements. The structure-based approaches include de Novo design, computer-based selection of ligands that are complementary with the target and computer-aided optimization of lead molecules. The detection of the PLB binding compounds can proceed by using the following steps:

1. The target region of the protein is selected. The binding model of the effective phospholamban deactivator peptide, cP226 (SEQ ID NO: 10), can be used to define an area on the phospholamban surface which can function as a target for phospholamban deactivators. Especially, this determines the side chains of phospholamban which can interact with the compounds to be designed.

2. Small molecules which are complementary to the binding site can be docked to the target by using available software, such as e.g. Ludi, DOCK or LeapFrog. Computer databases of three-dimensional structures of small molecules or molecular fragments can be used in the docking. Such an approach gives molecules or fragments that have good interactions with the various parts of the target area.

3. Different small molecules or fragments that bind to the target area can be linked together or one can incorporate new side chains and/or functional groups to them, so that one gets a single, larger molecule. The resulting new compound is likely to have better affinity to the target than the smaller molecules.

4. One can also select a proper scaffold and dock that by using an interactive molecular graphics system near the binding site of the protein. One can then add new fragments and functional groups to the scaffold, so that the new groups form good interactions with the target surface.

5. The cyclic peptide cP226 (SEQ ID NO: 10) is an example of a compound which binds to the ligand binding site of phospholamban. The structure of cP226 (SEQ ID NO: 10) can be used as a model for designing new compounds with affinity to phospholamban. Any of the well defined methods for designing peptidomimetics or, more generally, peptide mimics can be used to design such compounds.

A limited number of compounds can be selected through the process outlined above. Anyone skilled with the art would be able to identify such compounds by using the three dimensional structure of phospholamban stored in a computer system. The compounds can be then synthetized and tested for their ability to deactivate phosholamban in an assay similar to that outlined in example 3.

TABLE I

Orthogonal three dimensional coordinates in Ångströms for the cyclic peptide cP226 (SEQ ID NO: 10)

| Residue | Atom | X | Y | Z |
|---|---|---|---|---|
| 1 | CYS | N | −4.500 | −5.816 | 1.065 |
| 1 | CYS | CA | −3.913 | −5.081 | 2.195 |
| 1 | CYS | HN1 | −4.805 | −6.727 | 1.378 |
| 1 | CYS | HN2 | −5.291 | −5.300 | 0.706 |
| 1 | CYS | HN3 | −3.811 | −5.926 | 0.337 |
| 1 | CYS | HA | −4.673 | −5.015 | 2.974 |
| 1 | CYS | C | −3.521 | −3.665 | 1.797 |
| 1 | CYS | O | −4.275 | −2.984 | 1.106 |
| 1 | CYS | CB | −2.716 | −5.833 | 2.773 |
| 1 | CYS | SG | −1.186 | −5.807 | 1.793 |
| 1 | CYS | HB1 | −2.485 | −5.381 | 3.737 |
| 1 | CYS | HB2 | −3.005 | −6.870 | 2.943 |
| 1 | CYS | LG1 | −0.868 | −6.293 | 2.143 |
| 1 | CYS | LG2 | −1.298 | −5.206 | 1.500 |
| 2 | TYR | N | −2.334 | −3.230 | 2.226 |
| 2 | TYR | CA | −1.822 | −1.920 | 1.877 |
| 2 | TYR | HN | −1.741 | −3.845 | 2.764 |
| 2 | TYR | HA | −2.467 | −1.466 | 1.124 |
| 2 | TYR | C | −0.427 | −2.065 | 1.301 |
| 2 | TYR | O | −0.005 | −3.170 | 0.967 |
| 2 | TYR | CB | −1.782 | −1.016 | 3.105 |
| 2 | TYR | HB1 | −0.796 | −0.552 | 3.147 |
| 2 | TYR | HB2 | −2.524 | −0.231 | 2.974 |
| 2 | TYR | CG | −2.052 | −1.724 | 4.413 |
| 2 | TYR | CD1 | −3.368 | −1.863 | 4.872 |
| 2 | TYR | HD1 | −4.192 | −1.509 | 4.270 |
| 2 | TYR | CD2 | −0.987 | −2.180 | 5.200 |
| 2 | TYR | HD2 | 0.031 | −2.071 | 4.855 |
| 2 | TYR | CE1 | −3.619 | −2.453 | 6.116 |
| 2 | TYR | HE1 | −4.634 | −2.555 | 6.471 |
| 2 | TYR | CE2 | −1.238 | −2.769 | 6.445 |
| 2 | TYR | HE2 | −0.415 | −3.115 | 7.053 |
| 2 | TYR | CZ | −2.553 | −2.901 | 6.905 |
| 2 | TYR | OH | −2.798 | −3.464 | 8.124 |
| 2 | TYR | HH | −1.998 | −3.726 | 8.585 |
| 3 | TRP | N | 0.295 | −0.949 | 1.195 |
| 3 | TRP | CA | 1.639 | −0.990 | 0.666 |
| 3 | TRP | HN | −0.084 | −0.061 | 1.491 |

TABLE I-continued

Orthogonal three dimensional coordinates in Ångströms for the cyclic peptide cP226 (SEQ ID NO: 10)

| Residue | | Atom | X | Y | Z |
|---|---|---|---|---|---|
| 3 | TRP | HA | 2.012 | −2.004 | 0.800 |
| 3 | TRP | C | 2.542 | −0.026 | 1.422 |
| 3 | TRP | O | 2.112 | 0.623 | 2.372 |
| 3 | TRP | CB | 1.614 | −0.654 | −0.821 |
| 3 | TRP | HB1 | 0.826 | −1.238 | −1.296 |
| 3 | TRP | HB2 | 1.378 | 0.404 | −0.929 |
| 3 | TRP | CG | 2.892 | −0.918 | −1.546 |
| 3 | TRP | CD1 | 3.831 | 0.008 | −1.830 |
| 3 | TRP | CD2 | 3.402 | −2.178 | −2.077 |
| 3 | TRP | NE1 | 4.877 | −0.580 | −2.512 |
| 3 | TRP | CE2 | 4.664 | −1.934 | −2.681 |
| 3 | TRP | HD1 | 3.772 | 1.053 | −1.559 |
| 3 | TRP | HE1 | 5.708 | −0.104 | −2.833 |
| 3 | TRP | CE3 | 2.933 | −3.504 | −2.103 |
| 3 | TRP | HE3 | 1.978 | −3.737 | −1.655 |
| 3 | TRP | CZ2 | 5.421 | −2.947 | −3.276 |
| 3 | TRP | HZ2 | 6.378 | −2.724 | −3.723 |
| 3 | TRP | CZ3 | 3.684 | −4.528 | −2.696 |
| 3 | TRP | HZ3 | 3.302 | −5.338 | −2.700 |
| 3 | TRP | CH2 | 4.927 | −4.255 | −3.280 |
| 3 | TRP | HH2 | 5.501 | −5.051 | −3.731 |
| 4 | GLU | N | 3.799 | 0.056 | 0.982 |
| 4 | GLU | CA | 4.812 | 0.899 | 1.576 |
| 4 | GLU | HN | 4.087 | −0.499 | 0.192 |
| 4 | GLU | HA | 5.405 | 0.313 | 2.216 |
| 4 | GLU | C | 4.236 | 2.017 | 2.406 |
| 4 | GLU | O | 4.787 | 2.431 | 3.423 |
| 4 | GLU | CB | 5.698 | 1.448 | 0.481 |
| 4 | GLU | CG | 6.679 | 0.389 | −0.014 |
| 4 | GLU | CD | 7.595 | 0.956 | −1.091 |
| 4 | GLU | OE1 | 7.249 | 0.790 | −2.281 |
| 4 | GLU | OE2 | 8.627 | 1.545 | −0.704 |
| 4 | GLU | HB1 | 5.027 | 1.763 | −0.302 |
| 4 | GLU | HB2 | 6.242 | 2.305 | 0.856 |
| 4 | GLU | HG1 | 7.290 | 0.056 | 0.824 |
| 4 | GLU | HG2 | 6.128 | −0.462 | −0.411 |
| 5 | LEU | N | 3.135 | 2.522 | 1.889 |
| 5 | LEU | CA | 2.622 | 3.813 | 2.150 |
| 5 | LEU | HN | 2.818 | 2.140 | 1.031 |
| 5 | LEU | HA | 3.362 | 4.435 | 2.574 |
| 5 | LEU | C | 1.437 | 3.723 | 3.079 |
| 5 | LEU | O | 1.552 | 3.459 | 4.275 |
| 5 | LEU | CB | 2.300 | 4.379 | 0.776 |
| 5 | LEU | HB1 | 1.233 | 4.331 | 0.644 |
| 5 | LEU | HB2 | 2.784 | 3.725 | 0.059 |
| 5 | LEU | CG | 2.893 | 5.759 | 0.516 |
| 5 | LEU | HG | 3.808 | 5.818 | 1.092 |
| 5 | LEU | CD1 | 3.275 | 5.906 | −0.959 |
| 5 | LEU | HD11 | 4.091 | 5.223 | −1.199 |
| 5 | LEU | HD12 | 2.426 | 5.670 | −1.594 |
| 5 | LEU | HD13 | 3.598 | 6.928 | −1.157 |
| 5 | LEU | CD2 | 1.924 | 6.871 | 0.916 |
| 5 | LEU | HD21 | 1.572 | 6.707 | 1.933 |
| 5 | LEU | HD22 | 2.430 | 7.834 | 0.854 |
| 5 | LEU | HD23 | 1.076 | 6.877 | 0.232 |
| 6 | GLU | N | 0.310 | 4.034 | 2.475 |
| 6 | GLU | CA | −0.797 | 4.584 | 3.234 |
| 6 | GLU | HN | 0.545 | 4.337 | 1.543 |
| 6 | GLU | HA | −0.766 | 4.194 | 4.238 |
| 6 | GLU | C | −2.174 | 4.334 | 2.625 |
| 6 | GLU | O | −3.182 | 4.404 | 3.326 |
| 6 | GLU | CB | −0.517 | 6.066 | 3.324 |
| 6 | GLU | CG | −1.394 | 6.792 | 4.342 |
| 6 | GLU | CD | 1.241 | 6.210 | 5.741 |
| 6 | GLU | OE1 | −2.246 | 5.654 | 6.235 |
| 6 | GLU | OE2 | −0.124 | 6.332 | 6.290 |
| 6 | GLU | HB1 | 0.541 | 6.185 | 3.551 |
| 6 | GLU | HB2 | −0.707 | 6.444 | 2.332 |
| 6 | GLU | HG1 | −1.101 | 7.841 | 4.360 |
| 6 | GLU | HG2 | −2.436 | 6.722 | 4.036 |
| 7 | TRP | N | −2.229 | 4.100 | 1.315 |
| 7 | TRP | CA | −3.460 | 4.217 | 0.555 |
| 7 | TRP | HN | −1.368 | 3.977 | 0.804 |
| 7 | TRP | HA | −4.317 | 4.129 | 1.222 |
| 7 | TRP | C | −3.504 | 3.121 | −0.491 |
| 7 | TRP | O | −4.454 | 2.344 | −0.558 |
| 7 | TRP | CB | −3.485 | 5.577 | −0.150 |
| 7 | TRP | HB1 | −4.435 | 5.670 | −0.675 |
| 7 | TRP | HB2 | −3.431 | 6.359 | 0.607 |
| 7 | TRP | CG | −2.379 | 5.797 | −1.141 |
| 7 | TRP | CD1 | −1.059 | 5.740 | −0.857 |
| 7 | TRP | CD2 | −2.452 | 6.056 | −2.579 |
| 7 | TRP | NE1 | −0.316 | 5.931 | −1.995 |
| 7 | TRP | CE2 | −1.127 | 6.116 | −3.086 |
| 7 | TRP | HD1 | −0.629 | 5.529 | 0.104 |
| 7 | TRP | HE1 | 0.628 | 5.926 | −2.054 |
| 7 | TRP | CE3 | −3.486 | 6.229 | −3.517 |
| 7 | TRP | HE3 | −4.514 | 6.191 | −3.189 |
| 7 | TRP | CZ2 | −0.832 | 6.315 | −4.430 |
| 7 | TRP | HZ2 | 0.208 | 6.311 | −4.723 |
| 7 | TRP | CZ3 | −3.203 | 6.453 | −4.874 |
| 7 | TRP | HZ3 | −4.014 | 6.590 | −5.573 |
| 7 | TRP | CH2 | −1.880 | 6.491 | −5.336 |
| 7 | TRP | HH2 | −1.673 | 6.653 | −6.384 |
| 8 | LEU | N | −2.458 | 3.080 | −1.316 |
| 6 | LEU | CA | −2.399 | 2.215 | −2.463 |
| B | LEU | HN | −1.741 | 3.788 | −1.251 |
| 8 | LEU | HA | −3.342 | 2.268 | −2.987 |
| 8 | LEU | C | −2.138 | 0.775 | −2.047 |
| 8 | LEU | O | −2.050 | 0.466 | −0.861 |
| 8 | LEU | CB | −1.377 | 2.801 | −3.420 |
| 8 | LEU | HB1 | −1.919 | 3.553 | −3.985 |
| 8 | LEU | HB2 | −0.627 | 3.313 | −2.838 |
| 8 | LEU | CG | −0.697 | 1.810 | −4.364 |
| 8 | LEU | HG | −1.411 | 1.066 | −4.715 |
| 8 | LEU | CD1 | 0.486 | 1.139 | −3.660 |
| 8 | LEU | HD11 | 0.148 | 0.611 | −2.770 |
| 8 | LEU | HD12 | 0.958 | 0.428 | −4.336 |
| 8 | LEU | HD13 | 1.216 | 1.894 | −3.367 |
| 8 | LEU | CD2 | −0.166 | 2.597 | −5.559 |
| 8 | LEU | HD21 | 0.377 | 1.929 | −6.226 |
| 8 | LEU | HD22 | −0.999 | 3.047 | −6.099 |
| 8 | LEU | HD23 | 0.503 | 3.385 | −5.211 |
| 9 | PRO | N | −2.105 | −0.108 | −3.045 |
| 9 | PRO | CA | −2.388 | −1.520 | −2.908 |
| 9 | PRO | CD | −2.238 | 0.281 | −4.432 |
| 9 | PRO | HA | −3.411 | −1.651 | −2.592 |
| 9 | PRO | HD1 | −1.244 | 0.463 | −4.841 |
| 9 | PRO | HD2 | −2.849 | 1.180 | −4.534 |
| 9 | PRO | C | −1.489 | −2.327 | −2.003 |
| 9 | PRO | O | −0.712 | −1.817 | −1.200 |
| 9 | PRO | CB | −2.321 | −2.090 | −4.308 |
| 9 | PRO | HB1 | −2.906 | −3.003 | −4.418 |
| 9 | PRO | HB2 | −1.278 | −2.261 | −4.524 |
| 9 | PRO | CG | −2.874 | −0.932 | −5.115 |
| 9 | PRO | HG1 | −3.943 | −0.968 | −4.924 |
| 9 | PRO | HG2 | −2.647 | −0.998 | −6.179 |
| 10 | CYS | N | −1.663 | −3.631 | −2.196 |
| 10 | CYS | CA | −1.012 | −4.692 | −1.465 |
| 10 | CYS | HN | −2.332 | −3.890 | −2.912 |
| 10 | CYS | HA | −0.565 | −4.387 | −0.542 |
| 10 | CYS | C | 0.010 | −5.351 | −2.349 |
| 10 | CYS | O | 1.190 | −5.013 | −2.406 |
| 10 | CYS | CB | −2.057 | −5.730 | −1.120 |
| 10 | CYS | SG | −1.557 | −6.937 | 0.133 |
| 10 | CYS | HB1 | −2.248 | −6.248 | −2.047 |
| 10 | CYS | HB2 | −2.961 | −5.214 | −0.820 |
| 10 | CYS | LG1 | −2.185 | −7.126 | 0.309 |
| 10 | CYS | LG2 | −0.911 | −6.990 | −0.068 |
| 11 | ALA | N | −0.563 | −6.322 | −3.032 |
| 11 | ALA | CA | 0.071 | −7.137 | −4.047 |
| 11 | ALA | HN | −1.541 | −6.400 | −2.791 |
| 11 | ALA | HA | −0.700 | −7.659 | −4.614 |
| 11 | ALA | C | 0.986 | −8.164 | −3.395 |
| 11 | ALA | O | 1.316 | −7.956 | −2.208 |
| 11 | ALA | OXT | 1.336 | −9.138 | −4.095 |
| 11 | ALA | CB | 0.852 | −6.232 | −4.994 |
| 11 | ALA | HB1 | 1.630 | −5.713 | −4.434 |

TABLE I-continued

Orthogonal three dimensional coordinates in Ångströms for the cyclic peptide cP226 (SEQ ID NO: 10)

| Residue | Atom | X | Y | Z |
|---|---|---|---|---|
| 11 | ALA | HB2 | 1.304 | −6.831 | −5.783 |
| 11 | ALA | HB3 | 0.172 | −5.502 | −5.433 |
| END | | | | | |

TABLE III

Orthogonal three dimensional coordinates on Ångströms for the phospholamban (1–36) peptide (SEQ ID NO:9)

| Residue | Atom | X | Y | Z |
|---|---|---|---|---|
| 1 | MET | N | −18.883 | −3.493 | 9.020 |
| 1 | MET | CA | −17.518 | −3.957 | 8.653 |
| 1 | MET | HN1 | −19.536 | −4.279 | 9.119 |
| 1 | MET | HN2 | −18.890 | −2.989 | 9.914 |
| 1 | MET | HN3 | −19.280 | −2.863 | 8.314 |
| 1 | MET | HA | −16.901 | −3.038 | 8.626 |
| 1 | MET | C | −17.415 | −4.543 | 7.212 |
| 1 | MET | O | −16.572 | −4.081 | 6.439 |
| 1 | MET | CB | −16.875 | −4.826 | 9.772 |
| 1 | MET | HB1 | −15.795 | −4.924 | 9.547 |
| 1 | MET | HB2 | −16.893 | −4.265 | 10.726 |
| 1 | MET | CG | −17.422 | −6.248 | 10.031 |
| 1 | MET | SD | −19.151 | −6.241 | 10.562 |
| 1 | MET | CE | −18.991 | −5.887 | 12.325 |
| 1 | MET | HG1 | −17.330 | −6.874 | 9.124 |
| 1 | MET | HG2 | −16.810 | −6.758 | 10.798 |
| 1 | MET | HE1 | −19.984 | −5.878 | 12.809 |
| 1 | MET | HE2 | −18.374 | −6.655 | 12.827 |
| 1 | MET | HE3 | −18.521 | −4.900 | 12.492 |
| 2 | GLU | N | −18.254 | −5.533 | 6.842 |
| 2 | GLU | CA | −18.265 | −6.128 | 5.478 |
| 2 | GLU | HN | −18.900 | −5.856 | 7.571 |
| 2 | GLU | HA | −17.210 | −6.282 | 5.173 |
| 2 | GLU | C | −18.948 | −5.225 | 4.401 |
| 2 | GLU | O | −19.754 | −4.342 | 4.720 |
| 2 | GLU | CB | −18.906 | −7.547 | 5.541 |
| 2 | GLU | CG | −20.416 | −7.627 | 5.896 |
| 2 | GLU | CD | −21.035 | −8.987 | 5.590 |
| 2 | GLU | OE1 | −21.495 | −9.191 | 4.444 |
| 2 | GLU | OE2 | −21.070 | −9.854 | 6.489 |
| 2 | GLU | HB1 | −18.746 | −8.031 | 4.557 |
| 2 | GLU | HB2 | −18.337 | −8.184 | 6.246 |
| 2 | GLU | HG1 | −20.571 | −7.388 | 6.963 |
| 2 | GLU | HG2 | −20.990 | −6.864 | 5.338 |
| 3 | LYS | N | −18.664 | −5.521 | 3.116 |
| 3 | LYS | CA | −19.464 | −5.049 | 1.948 |
| 3 | LYS | HN | −17.993 | −6.291 | 3.013 |
| 3 | LYS | HA | −19.008 | −5.581 | 1.092 |
| 3 | LYS | C | −19.248 | −3.539 | 1.622 |
| 3 | LYS | O | −18.370 | −3.219 | 0.818 |
| 3 | LYS | CB | −20.930 | −5.587 | 1.997 |
| 3 | LYS | CG | −21.709 | −5.508 | 0.666 |
| 3 | LYS | CD | −23.177 | −5.990 | 0.736 |
| 3 | LYS | CE | −23.411 | −7.513 | 0.856 |
| 3 | LYS | NZ | −23.320 | −8.021 | 2.243 |
| 3 | LYS | HB1 | −20.905 | −6.644 | 2.322 |
| 3 | LYS | HB2 | −21.495 | −5.058 | 2.788 |
| 3 | LYS | HG1 | −21.711 | −4.458 | 0.320 |
| 3 | LYS | HG2 | −21.169 | −6.068 | −0.122 |
| 3 | LYS | HD1 | −23.726 | −5.441 | 1.525 |
| 3 | LYS | HD2 | −23.662 | −5.662 | −0.204 |
| 3 | LYS | HE1 | −24.420 | −7.750 | 0.465 |
| 3 | LYS | HE2 | −22.711 | −8.069 | 0.201 |
| 3 | LYS | HZ1 | −22.376 | −7.928 | 2.639 |
| 3 | LYS | HZ2 | −23.954 | −7.523 | 2.880 |
| 3 | LYS | HZ3 | −23.558 | −9.017 | 2.311 |
| 4 | VAL | N | −20.017 | −2.625 | 2.249 |
| 4 | VAL | CA | −19.844 | −1.150 | 2.084 |
| 4 | VAL | HN | −20.672 | −3.020 | 2.932 |

TABLE III-continued

Orthogonal three dimensional coordinates on Ångströms for the phospholamban (1–36) peptide (SEQ ID NO:9)

| Residue | Atom | X | Y | Z |
|---|---|---|---|---|
| 4 | VAL | HA | −19.723 | −0.979 | 0.995 |
| 4 | VAL | C | −18.532 | −0.595 | 2.734 |
| 4 | VAL | O | −17.763 | 0.075 | 2.042 |
| 4 | VAL | CB | −21.166 | −0.392 | 2.460 |
| 4 | VAL | HB | −21.981 | −0.865 | 1.880 |
| 4 | VAL | CG1 | −21.148 | 1.087 | 2.010 |
| 4 | VAL | HG11 | −22.125 | 1.579 | 2.173 |
| 4 | VAL | HG12 | −20.389 | 1.679 | 2.555 |
| 4 | VAL | HG13 | −20.921 | 1.182 | 0.931 |
| 4 | VAL | CG2 | −21.594 | −0.469 | 3.946 |
| 4 | VAL | HG21 | −22.587 | −0.009 | 4.106 |
| 4 | VAL | HG22 | −21.672 | −1.514 | 4.297 |
| 4 | VAL | HG23 | −20.886 | 0.051 | 4.615 |
| 5 | GLN | N | −18.257 | −0.895 | 4.022 |
| 5 | GLN | CA | −16.969 | −0.532 | 4.685 |
| 5 | GLN | HN | −18.970 | −1.467 | 4.487 |
| 5 | GLN | HA | −16.753 | 0.525 | 4.431 |
| 5 | GLN | C | −15.708 | −1.326 | 4.214 |
| 5 | GLN | O | −14.609 | −0.764 | 4.263 |
| 5 | GLN | CB | −17.126 | −0.595 | 6.230 |
| 5 | GLN | HB1 | −16.134 | −0.491 | 6.711 |
| 5 | GLN | HB2 | −17.470 | −1.605 | 6.519 |
| 5 | GLN | CG | −19.072 | 0.452 | 6.870 |
| 5 | GLN | HG1 | −19.093 | 0.350 | 6.454 |
| 5 | GLN | HG2 | −18.189 | 0.209 | 7.943 |
| 5 | GLN | CD | −17.577 | 1.906 | 6.777 |
| 5 | GLN | OE1 | −16.699 | 2.331 | 7.525 |
| 5 | GLN | NE2 | −18.118 | 2.697 | 5.865 |
| 5 | GLN | HE21 | −17.754 | 3.655 | 5.830 |
| 5 | GLN | HE22 | −18.828 | 2.281 | 5.254 |
| 6 | TYR | N | −15.837 | −2.578 | 3.722 |
| 6 | TYR | CA | −14.754 | −3.255 | 2.953 |
| 6 | TYR | HN | −16.798 | −2.934 | 3.726 |
| 6 | TYR | HA | −13.836 | −3.179 | 3.569 |
| 6 | TYR | C | −14.429 | −2.578 | 1.577 |
| 6 | TYR | O | −13.246 | −2.405 | 1.284 |
| 6 | TYR | CB | −15.073 | −4.771 | 2.823 |
| 6 | TYR | HB1 | −15.450 | −5.161 | 3.789 |
| 6 | TYR | HB2 | −15.922 | −4.917 | 2.126 |
| 6 | TYR | CG | −13.870 | −5.631 | 2.391 |
| 6 | TYR | CD1 | −12.947 | −6.081 | 3.342 |
| 6 | TYR | HD1 | −13.093 | −5.867 | 4.391 |
| 6 | TYR | CD2 | −13.656 | −5.919 | 1.038 |
| 6 | TYR | HD2 | −14.351 | −5.571 | 0.287 |
| 6 | TYR | CE1 | −11.820 | −6.795 | 2.944 |
| 6 | TYR | HE1 | −11.109 | −7.135 | 3.683 |
| 6 | TYR | CE2 | −12.526 | −6.633 | 0.642 |
| 6 | TYR | HE2 | −12.364 | −6.840 | −0.406 |
| 6 | TYR | CZ | −11.608 | −7.066 | 1.594 |
| 6 | TYR | OH | −10.486 | −7.749 | 1.203 |
| 6 | TYR | HH | −10.543 | −7.928 | 0.261 |
| 7 | LEU | N | −15.435 | −2.177 | 0.768 |
| 7 | LEU | CA | −15.228 | −1.333 | −0.448 |
| 7 | LEU | HN | −16.377 | −2.392 | 1.118 |
| 7 | LEU | HA | −14.505 | −1.879 | −1.083 |
| 7 | LEU | C | −14.618 | 0.088 | −0.187 |
| 7 | LEU | O | −13.755 | 0.514 | −0.959 |
| 7 | LEU | CB | −16.568 | −1.276 | −1.239 |
| 7 | LEU | HB1 | −16.964 | −2.304 | −1.362 |
| 7 | LEU | HB2 | −17.320 | −0.763 | −0.607 |
| 7 | LEU | CG | −16.545 | −0.600 | −2.641 |
| 7 | LEU | HG | −16.134 | 0.421 | −2.532 |
| 7 | LEU | CD1 | −17.977 | −0.449 | −3.189 |
| 7 | LEU | HD11 | −18.471 | −1.427 | −3.341 |
| 7 | LEU | HD12 | −18.616 | 0.136 | −2.501 |
| 7 | LEU | HD13 | −17.989 | 0.081 | −4.159 |
| 7 | LEU | CD2 | −15.670 | −1.352 | −3.665 |
| 7 | LEU | HD21 | −16.014 | −2.391 | −3.823 |
| 7 | LEU | HD22 | −15.676 | −0.852 | −4.652 |
| 7 | LEU | HD23 | −14.613 | −1.398 | −3.347 |
| 8 | THR | N | −15.020 | 0.793 | 0.895 |
| 8 | THR | CA | −14.337 | 2.035 | 1.379 |
| 8 | THR | HN | −15.786 | 0.362 | 1.425 |

TABLE III-continued

Orthogonal three dimensional coordinates on Ångstroms for the phospholamban (1–36) peptide (SEQ ID NO:9)

| Residue | | Atom | X | Y | Z |
|---|---|---|---|---|---|
| 8 | THR | HA | −14.401 | 2.775 | 0.558 |
| 8 | THR | C | −12.813 | 1.822 | 1.687 |
| 8 | THR | O | −11.983 | 2.555 | 1.144 |
| 8 | THR | CB | −15.125 | 2.633 | 2.591 |
| 8 | TRR | OG1 | −16.503 | 2.806 | 2.270 |
| 8 | THR | HB | −15.061 | 1.931 | 3.445 |
| 8 | THR | HG1 | −16.535 | 3.486 | 1.594 |
| 8 | THR | CG2 | −14.620 | 4.006 | 3.070 |
| 8 | THR | HG21 | −14.652 | 4.764 | 2.265 |
| 8 | THR | HG22 | −15.233 | 4.389 | 3.908 |
| 8 | THR | HG23 | −13.579 | 3.955 | 3.436 |
| 9 | ARG | N | −12.454 | 0.800 | 2.491 |
| 9 | ARG | CA | −11.040 | 0.367 | 2.694 |
| 9 | ARG | HN | −13.242 | 0.262 | 2.868 |
| 9 | ARG | HA | −10.475 | 1.248 | 3.056 |
| 9 | ARG | C | −10.279 | −0.141 | 1.422 |
| 9 | ARG | O | −9.068 | 0.074 | 1.342 |
| 9 | ARG | CB | −10.986 | −0.704 | 3.816 |
| 9 | ARG | CG | −11.336 | −0.195 | 5.239 |
| 9 | ARG | CD | −11.278 | −1.278 | 6.331 |
| 9 | ARG | NE | −12.399 | −2.249 | 6.225 |
| 9 | ARG | CZ | −12.453 | −3.428 | 6.870 |
| 9 | ARG | NH1 | −13.518 | −4.178 | 6.704 |
| 9 | ARG | NH2 | −11.493 | −3.881 | 7.666 |
| 9 | ARG | HB1 | −9.966 | −1.132 | 3.664 |
| 9 | ARG | HB2 | −11.641 | −1.555 | 3.549 |
| 9 | ARG | HG1 | −10.627 | 0.611 | 5.509 |
| 9 | ARG | HG2 | −12.331 | 0.292 | 5.247 |
| 9 | ARG | HD1 | −10.296 | −1.790 | 6.290 |
| 9 | ARG | HD2 | −11.320 | −0.790 | 7.325 |
| 9 | ARG | HE | −13.225 | −2.039 | 5.652 |
| 9 | ARG | HH12 | −14.259 | −3.806 | 6.101 |
| 9 | ARG | HH11 | −13.535 | −5.071 | 7.209 |
| 9 | ARG | HH21 | −10.677 | −3.270 | 7.781 |
| 9 | ARG | HH22 | −11.642 | −4.793 | 8.108 |
| 10 | SER | N | −10.946 | −0.787 | 0.443 |
| 10 | SER | CA | −10.354 | −1.132 | −0.884 |
| 10 | SER | HN | −11.942 | −0.946 | 0.641 |
| 10 | SER | HA | −9.439 | −1.724 | −0.697 |
| 10 | SER | C | −9.924 | 0.093 | −1.755 |
| 10 | SER | O | −8.816 | 0.081 | −2.300 |
| 10 | SER | CB | −11.306 | −2.070 | −1.661 |
| 10 | SER | OG | −11.499 | −3.303 | −0.971 |
| 10 | SER | HB1 | −12.283 | −1.585 | −1.840 |
| 10 | SER | HB2 | −10.895 | −2.294 | −2.663 |
| 10 | SER | HG | −12.151 | −3.796 | −1.475 |
| 11 | ALA | N | −10.757 | 1.151 | −1.848 |
| 11 | ALA | CA | −10.344 | 2.469 | −2.403 |
| 11 | ALA | HN | −11.651 | 1.031 | −1.357 |
| 11 | ALA | HA | −9.966 | 2.296 | −3.429 |
| 11 | ALA | C | −9.219 | 3.223 | −1.619 |
| 11 | ALA | O | −8.321 | 3.776 | −2.259 |
| 11 | ALA | CB | −11.608 | 3.341 | −2.539 |
| 11 | ALA | HB1 | −12.075 | 3.558 | −1.559 |
| 11 | ALA | HB2 | −11.379 | 4.314 | −3.012 |
| 11 | ALA | HB3 | −12.378 | 2.857 | −3.170 |
| 12 | ILE | N | −9.242 | 3.226 | −0.266 |
| 12 | ILE | CA | −8.172 | 3.838 | 0.586 |
| 12 | ILE | HN | −10.056 | 2.754 | 0.145 |
| 12 | ILE | HA | −8.006 | 4.865 | 0.200 |
| 12 | ILE | C | −6.795 | 3.099 | 0.438 |
| 12 | ILE | O | −5.794 | 3.779 | 0.207 |
| 12 | ILE | CB | −8.658 | 4.011 | 2.076 |
| 12 | ILE | HB | −8.948 | 3.006 | 2.440 |
| 12 | ILE | CG1 | −9.901 | 4.950 | 2.214 |
| 12 | ILE | HG11 | −10.620 | 4.757 | 1.398 |
| 12 | ILE | HG12 | −9.602 | 6.005 | 2.066 |
| 12 | ILE | CG2 | −7.544 | 4.533 | 3.028 |
| 12 | ILE | HG21 | −7.887 | 4.618 | 4.075 |
| 12 | ILE | HG22 | −6.669 | 3.857 | 3.055 |
| 12 | ILE | HG23 | −7.174 | 5.529 | 2.721 |
| 12 | ILE | CD1 | −10.686 | 4.819 | 3.530 |
| 12 | ILE | HD11 | −11.582 | 5.467 | 3.523 |
| 12 | ILE | HD12 | −11.037 | 3.782 | 3.694 |
| 12 | ILE | HD13 | −10.086 | 5.112 | 4.410 |
| 13 | ARG | N | −6.728 | 1.753 | 0.563 |
| 13 | ARG | CA | −5.468 | 0.976 | 0.354 |
| 13 | ARG | HN | −7.628 | 1.294 | 0.749 |
| 13 | ARG | HA | −4.726 | 1.433 | 1.041 |
| 13 | ARG | C | −4.830 | 1.090 | −1.073 |
| 13 | ARG | O | −3.613 | 1.260 | −1.173 |
| 13 | ARG | CB | −5.630 | −0.486 | 0.871 |
| 13 | ARG | CG | −6.342 | −1.498 | −0.063 |
| 13 | ARG | CD | −6.640 | −2.883 | 0.549 |
| 13 | ARG | NE | −7.896 | −2.883 | 1.345 |
| 13 | ARG | CZ | −8.627 | −3.976 | 1.626 |
| 13 | ARG | NH1 | −8.236 | −5.216 | 1.363 |
| 13 | ARG | NH2 | −9.800 | −3.810 | 2.198 |
| 13 | ARG | HB1 | −6.139 | −0.472 | 1.855 |
| 13 | ARG | HB2 | −4.622 | −0.886 | 1.095 |
| 13 | ARG | HG1 | −7.266 | −1.050 | −0.471 |
| 13 | ARG | HG2 | −5.699 | −1.654 | −0.950 |
| 13 | ARG | HD1 | −6.722 | −3.609 | −0.283 |
| 13 | ARG | HD2 | −5.789 | −3.231 | 1.168 |
| 13 | ARG | HE | −8.340 | −1.998 | 1.613 |
| 13 | ARG | HH12 | −7.314 | −5.315 | 0.927 |
| 13 | ARG | HH11 | −8.879 | −5.974 | 1.620 |
| 13 | ARG | HH21 | −10.096 | −2.844 | 2.364 |
| 13 | ARG | HH22 | −10.347 | −4.658 | 2.382 |
| 14 | ARG | N | −5.647 | 1.040 | −2.150 |
| 14 | ARG | CA | −5.205 | 1.316 | −3.547 |
| 14 | ARG | HN | −6.640 | 0.917 | −1.918 |
| 14 | ARG | HA | −4.382 | 0.609 | −3.774 |
| 14 | ARG | C | −4.654 | 2.762 | −3.783 |
| 14 | ARG | O | −3.574 | 2.899 | −4.362 |
| 14 | ARG | CB | −6.387 | 0.954 | −4.492 |
| 14 | ARG | CG | −6.046 | 0.936 | −6.002 |
| 14 | ARG | CD | −7.241 | 0.641 | −6.935 |
| 14 | ARG | NE | −7.781 | −0.743 | −6.818 |
| 14 | ARG | CZ | −7.326 | −1.813 | −7.495 |
| 14 | ARG | NH1 | −6.304 | −1.776 | −8.341 |
| 14 | ARG | NH2 | −7.927 | −2.967 | −7.304 |
| 14 | ARG | HB1 | −6.779 | −0.047 | −4.223 |
| 14 | ARG | HB2 | −7.232 | 1.648 | −4.313 |
| 14 | ARG | HG1 | −5.635 | 1.922 | −6.287 |
| 14 | ARG | HG2 | −5.227 | 0.217 | −6.196 |
| 14 | ARG | HD1 | −8.058 | 1.355 | −6.720 |
| 14 | ARG | HD2 | −6.959 | 0.862 | −7.983 |
| 14 | ARG | HE | −8.576 | −0.946 | −6.202 |
| 14 | ARG | HH12 | −5.856 | −0.864 | −8.466 |
| 14 | ARG | HH11 | −6.046 | −2.656 | −8.800 |
| 14 | ARG | HH21 | −8.716 | −2.973 | −6.649 |
| 14 | ARG | HH22 | −7.566 | −3.769 | −7.830 |
| 15 | ALA | N | −5.366 | 3.815 | −3.329 |
| 15 | ALA | CA | −4.859 | 5.215 | −3.352 |
| 15 | ALA | HN | −6.249 | 3.572 | −2.865 |
| 15 | ALA | HA | −4.610 | 5.460 | −4.404 |
| 15 | ALA | C | −3.580 | 5.502 | −2.503 |
| 15 | ALA | O | −2.687 | 6.192 | −2.996 |
| 15 | ALA | CB | −6.019 | 6.148 | −2.948 |
| 15 | ALA | HB1 | −5.723 | 7.211 | −3.012 |
| 15 | ALA | HB2 | −6.898 | 6.024 | −3.608 |
| 15 | ALA | HB3 | −6.360 | 5.965 | −1.911 |
| 16 | SER | N | −3.471 | 4.962 | −1.270 |
| 16 | SER | CA | −2.253 | 5.080 | −0.420 |
| 16 | SER | HN | −4.293 | 4.425 | −0.965 |
| 16 | SER | HA | −2.050 | 6.162 | −0.292 |
| 16 | SER | C | −0.958 | 4.438 | −1.011 |
| 16 | SER | O | 0.081 | 5.105 | −1.033 |
| 16 | SER | CB | −2.595 | 4.527 | 0.984 |
| 16 | SER | OG | −1.533 | 4.766 | 1.904 |
| 16 | SER | HB1 | −2.808 | 3.441 | 0.942 |
| 16 | SER | HB2 | −3.513 | 5.000 | 1.382 |
| 16 | SER | HG | −0.749 | 4.360 | 1.526 |
| 17 | THR | N | −1.011 | 3.178 | −1.503 |
| 17 | THR | CA | 0.124 | 2.551 | −2.246 |

TABLE III-continued

Orthogonal three dimensional coordinates on Ångstroms for the phospholamban (1–36) peptide (SEQ ID NO:9)

| Residue | | Atom | X | Y | Z |
|---|---|---|---|---|---|
| 17 | THR | HN | -1.934 | 2.731 | -1.438 |
| 17 | THR | HA | 1.023 | 2.737 | -1.625 |
| 17 | THR | C | 0.453 | 3.189 | -3.638 |
| 17 | THR | O | 1.637 | 3.295 | -3.969 |
| 17 | THR | CB | -0.014 | 0.998 | -2.268 |
| 17 | THR | OG1 | 1.246 | 0.419 | -2.593 |
| 17 | THR | HB | -0.270 | 0.656 | -1.245 |
| 17 | THR | HG1 | 1.437 | 0.690 | -3.494 |
| 17 | THR | CG2 | -1.058 | 0.403 | -3.230 |
| 17 | THR | HG21 | -1.179 | -0.683 | -3.070 |
| 17 | THR | HG22 | -2.050 | 0.867 | -3.099 |
| 17 | THR | HG23 | -0.770 | 0.546 | -4.287 |
| 18 | ILE | N | -0.556 | 3.629 | -4.427 |
| 18 | ILE | CA | -0.333 | 4.400 | -5.692 |
| 18 | ILE | HN | -1.497 | 3.496 | -4.036 |
| 18 | ILE | HA | 0.698 | 4.211 | -6.053 |
| 18 | ILE | C | -0.421 | 5.946 | -5.379 |
| 18 | ILE | O | -1.236 | 6.672 | -5.957 |
| 18 | ILE | CB | -1.288 | 3.908 | -6.852 |
| 18 | ILE | HB | -2.305 | 4.271 | -6.603 |
| 18 | ILE | CG1 | -1.395 | 2.357 | -7.037 |
| 18 | ILE | HG11 | -1.526 | 1.871 | -6.054 |
| 18 | ILE | HG12 | -0.444 | 1.948 | -7.427 |
| 18 | ILE | CG2 | -0.883 | 4.538 | -8.215 |
| 18 | ILE | HG21 | -0.844 | 5.641 | -8.182 |
| 18 | ILE | HG22 | 0.115 | 4.193 | -8.547 |
| 18 | ILE | HG23 | -1.597 | 4.290 | -9.020 |
| 18 | ILE | CD1 | -2.570 | 1.867 | -7.901 |
| 18 | ILE | HD11 | -2.470 | 2.172 | -8.958 |
| 18 | ILE | HD12 | -2.641 | 0.764 | -7.888 |
| 18 | ILE | HD13 | -3.536 | 2.260 | -7.531 |
| 19 | GLU | N | 0.446 | 6.441 | -4.470 |
| 19 | GLU | CA | 0.634 | 7.888 | -4.165 |
| 19 | GLU | HN | 1.033 | 5.726 | -4.025 |
| 19 | GLU | HA | 0.850 | 8.416 | -5.116 |
| 19 | GLU | C | 1.890 | 7.939 | -3.246 |
| 19 | GLU | O | 1.773 | 7.912 | -2.015 |
| 19 | GLU | CB | -0.615 | 8.561 | -3.518 |
| 19 | GLU | CG | -0.502 | 10.091 | -3.331 |
| 19 | GLU | CD | -1.757 | 10.709 | -2.714 |
| 19 | GLU | OE1 | -1.821 | 10.833 | -1.471 |
| 19 | GLU | OE2 | -2.681 | 11.079 | -3.471 |
| 19 | GLU | HB1 | -1.509 | 8.364 | -4.140 |
| 19 | GLU | HB2 | -0.836 | 8.082 | -2.544 |
| 19 | GLU | HG1 | 0.364 | 10.339 | -2.690 |
| 19 | GLU | HG2 | -0.306 | 10.582 | -4.302 |
| 20 | MET | N | 3.097 | 7.953 | -3.849 |
| 20 | MET | CA | 4.367 | 7.766 | -3.099 |
| 20 | MET | HN | 3.066 | 7.947 | -4.874 |
| 20 | MET | HA | 4.229 | 8.109 | -2.058 |
| 20 | MET | C | 5.500 | 8.612 | -3.764 |
| 20 | MET | O | 5.912 | 8.250 | -4.873 |
| 20 | MET | CB | 4.774 | 6.264 | -3.011 |
| 20 | MET | HB1 | 4.730 | 5.784 | -4.006 |
| 20 | MET | HB2 | 5.837 | 6.193 | -2.714 |
| 20 | MET | CG | 3.968 | 5.437 | -1.993 |
| 20 | MET | SD | 4.791 | 3.860 | -1.711 |
| 20 | MET | CE | 4.009 | 3.366 | -0.164 |
| 20 | MET | HG1 | 3.884 | 5.980 | -1.034 |
| 20 | MET | HG2 | 2.935 | 5.259 | -2.347 |
| 20 | MET | HE1 | 4.407 | 2.394 | 0.179 |
| 20 | MET | HE2 | 4.198 | 4.113 | 0.628 |
| 20 | MET | HE3 | 2.916 | 3.266 | -0.289 |
| 21 | PRO | N | 6.082 | 9.682 | -3.136 |
| 21 | PRO | CA | 7.307 | 10.353 | -3.561 |
| 21 | PRO | CD | 5.577 | 10.289 | -1.885 |
| 21 | PRO | HA | 7.190 | 10.566 | -4.742 |
| 21 | PRO | HD1 | 5.491 | 9.562 | -1.057 |
| 21 | PRO | HD2 | 4.577 | 10.737 | -2.051 |
| 21 | PRO | C | 8.610 | 9.505 | -3.466 |
| 21 | PRO | O | 8.564 | 8.355 | -3.015 |
| 21 | PRO | CB | 7.264 | 11.689 | -2.884 |
| 21 | PRO | HB1 | 8.254 | 12.168 | -2.762 |
| 21 | PRO | HB2 | 6.636 | 12.421 | -3.431 |
| 21 | PRO | CG | 6.612 | 11.360 | -1.542 |
| 21 | PRO | HG1 | 6.162 | 12.247 | -1.057 |
| 21 | PRO | HG2 | 7.367 | 10.953 | -0.842 |
| 22 | GLN | N | 9.775 | 10.079 | -3.825 |
| 22 | GLN | CA | 11.099 | 9.383 | -3.763 |
| 22 | GLN | HN | 9.684 | 11.028 | -4.202 |
| 22 | GLN | HA | 11.033 | 8.583 | -4.525 |
| 22 | GLN | C | 11.482 | 8.638 | -2.439 |
| 22 | GLN | O | 11.949 | 7.500 | -2.513 |
| 22 | GLN | CB | 12.223 | 10.322 | -4.282 |
| 22 | GLN | HB1 | 13.148 | 9.727 | -4.407 |
| 22 | GLN | HB2 | 11.966 | 10.640 | -5.311 |
| 22 | GLN | CG | 12.550 | 11.578 | -3.435 |
| 22 | GLN | HG1 | 11.630 | 12.168 | -3.268 |
| 22 | GLN | HG2 | 12.884 | 11.281 | -2.422 |
| 22 | GLN | CD | 13.588 | 12.498 | -4.093 |
| 22 | GLN | OE1 | 13.260 | 13.333 | -4.933 |
| 22 | GLN | NE2 | 14.855 | 12.373 | -3.736 |
| 22 | GLN | HE21 | 15.067 | 11.660 | -3.030 |
| 22 | GLN | HE22 | 15.516 | 13.007 | -4.196 |
| 23 | GLN | N | 11.241 | 9.236 | -1.255 |
| 23 | GLN | CA | 11.413 | 8.552 | 0.061 |
| 23 | GLN | HN | 10.841 | 10.178 | -1.328 |
| 23 | GLN | HA | 12.430 | 8.113 | 0.051 |
| 23 | GLN | C | 10.448 | 7.350 | 0.351 |
| 23 | GLN | O | 10.910 | 6.324 | 0.858 |
| 23 | GLN | CB | 11.447 | 9.600 | 1.208 |
| 23 | GLN | HB1 | 12.280 | 10.306 | 1.013 |
| 23 | GLN | HB2 | 11.743 | 9.086 | 2.143 |
| 23 | GLN | CG | 10.154 | 10.415 | 1.475 |
| 23 | GLN | HG1 | 9.839 | 10.931 | 0.549 |
| 23 | GLN | HG2 | 9.316 | 9.735 | 1.719 |
| 23 | GLN | CD | 10.320 | 11.475 | 2.574 |
| 23 | GLN | OE1 | 10.799 | 12.580 | 2.329 |
| 23 | GLN | NE2 | 9.928 | 11.173 | 3.800 |
| 23 | GLN | HE21 | 9.539 | 10.235 | 3.942 |
| 23 | GLN | HE22 | 10.049 | 11.909 | 4.503 |
| 24 | ALA | N | 9.143 | 7.463 | 0.030 |
| 24 | ALA | CA | 8.159 | 6.359 | 0.204 |
| 24 | ALA | HN | 8.886 | 8.352 | -0.413 |
| 24 | ALA | HA | 8.289 | 5.956 | 1.227 |
| 24 | ALA | C | 8.290 | 5.147 | -0.774 |
| 24 | ALA | O | 8.102 | 4.010 | -0.329 |
| 24 | ALA | CB | 6.748 | 6.969 | 0.163 |
| 24 | ALA | HB1 | 6.615 | 7.761 | 0.924 |
| 24 | ALA | HB2 | 6.522 | 7.421 | -0.821 |
| 24 | ALA | HB3 | 5.969 | 6.209 | 0.360 |
| 25 | ARG | N | 8.632 | 5.358 | -2.064 |
| 25 | ARG | CA | 9.043 | 4.252 | -2.981 |
| 25 | ARG | RN | 8.743 | 6.347 | -2.322 |
| 25 | ARG | HA | 8.300 | 3.441 | -2.842 |
| 25 | ARG | C | 10.430 | 3.587 | -2.668 |
| 25 | ARG | O | 10.540 | 2.365 | -2.801 |
| 25 | ARG | CB | 8.889 | 4.651 | -4.473 |
| 25 | ARG | CG | 9.786 | 5.799 | -5.012 |
| 25 | ARG | CD | 10.177 | 5.685 | -6.502 |
| 25 | ARG | NE | 11.091 | 4.541 | -6.782 |
| 25 | ARG | CZ | 12.421 | 4.541 | -6.578 |
| 25 | ARG | NH1 | 13.108 | 5.603 | -6.180 |
| 25 | ARG | NH2 | 13.079 | 3.421 | -6.783 |
| 25 | ARG | HB1 | 7.831 | 4.908 | -4.677 |
| 25 | ARG | HB2 | 9.054 | 3.736 | -5.072 |
| 25 | ARG | HG1 | 9.259 | 6.756 | -4.857 |
| 25 | ARG | HG2 | 10.708 | 5.894 | -4.408 |
| 25 | ARG | HD1 | 9.264 | 5.572 | -7.115 |
| 25 | ARG | HD2 | 10.627 | 6.636 | -6.847 |
| 25 | ARG | HE | 10.720 | 3.637 | -7.092 |
| 25 | ARG | HH12 | 12.567 | 6.460 | -6.027 |
| 25 | ARG | HH11 | 14.116 | 5.475 | -6.041 |
| 25 | ARG | HH21 | 12.529 | 2.612 | -7.087 |
| 25 | ARG | HH22 | 14.087 | 3.441 | -6.595 |
| 26 | GLN | N | 11.453 | 4.360 | -2.215 |

TABLE III-continued

Orthogonal three dimensional coordinates on Ångstroms for the phospholamban (1–36) peptide (SEQ ID NO:9)

| Residue | | Atom | X | Y | Z |
|---|---|---|---|---|---|
| 26 | GLN | CA | 12.697 | 3.779 | −1.612 |
| 26 | GLN | HN | 11.240 | 5.353 | −2.152 |
| 26 | GLN | HA | 13.138 | 3.102 | −2.365 |
| 26 | GLN | C | 12.484 | 2.907 | −0.334 |
| 26 | GLN | O | 13.148 | 1.878 | −0.206 |
| 26 | GLN | CB | 13.749 | 4.894 | −1.344 |
| 26 | GLN | HB1 | 13.273 | 5.724 | −0.787 |
| 26 | GLN | HB2 | 14.530 | 4.520 | −0.653 |
| 26 | GLN | CG | 14.472 | 5.467 | −2.589 |
| 26 | GLN | HG1 | 15.030 | 6.376 | −2.295 |
| 26 | GLN | HG2 | 13.724 | 5.828 | −3.317 |
| 26 | GLN | CD | 15.422 | 4.491 | −3.305 |
| 26 | GLN | OE1 | 15.071 | 3.875 | −4.309 |
| 26 | GLN | NE2 | 16.638 | 4.327 | −2.815 |
| 26 | GLN | HE21 | 16.862 | 4.843 | −1.957 |
| 26 | GLN | HE22 | 17.228 | 3.639 | −3.294 |
| 27 | LYS | N | 11.548 | 3.264 | 0.572 |
| 27 | LYS | CA | 11.074 | 2.367 | 1.667 |
| 27 | LYS | HN | 11.088 | 4.160 | 0.371 |
| 27 | LYS | HA | 11.940 | 2.194 | 2.336 |
| 27 | LYS | C | 10.559 | 0.961 | 1.203 |
| 27 | LYS | O | 10.956 | −0.041 | 1.801 |
| 27 | LYS | CB | 10.012 | 3.154 | 2.484 |
| 27 | LYS | CG | 9.566 | 2.501 | 3.813 |
| 27 | LYS | CD | 8.426 | 3.241 | 4.552 |
| 27 | LYS | CE | 6.988 | 2.966 | 4.055 |
| 27 | LYS | NZ | 6.636 | 3.687 | 2.812 |
| 27 | LYS | HB1 | 9.132 | 3.324 | 1.842 |
| 27 | LYS | HB2 | 10.393 | 4.168 | 2.720 |
| 27 | LYS | HG1 | 9.272 | 1.447 | 3.652 |
| 27 | LYS | HG2 | 10.446 | 2.449 | 4.483 |
| 27 | LYS | HD1 | 8.466 | 2.914 | 5.609 |
| 27 | LYS | HD2 | 8.630 | 4.328 | 4.599 |
| 27 | LYS | HE1 | 6.828 | 1.878 | 3.918 |
| 27 | LYS | HE2 | 6.273 | 3.264 | 4.847 |
| 27 | LYS | HZ1 | 6.751 | 4.702 | 2.914 |
| 27 | LYS | HZ2 | 7.225 | 3.398 | 2.022 |
| 27 | LYS | HZ3 | 5.663 | 3.522 | 2.532 |
| 28 | LEU | N | 9.719 | 0.878 | 0.145 |
| 28 | LEU | CA | 9.260 | −0.418 | −0.438 |
| 28 | LEU | HN | 9.490 | 1.779 | −0.290 |
| 28 | LEU | HA | 8.796 | −0.997 | 0.384 |
| 28 | LEU | C | 10.403 | −1.321 | −1.004 |
| 28 | LEU | O | 10.505 | −2.475 | −0.581 |
| 28 | LEU | CB | 8.156 | −0.187 | −1.513 |
| 28 | LEU | HB1 | 8.584 | 0.438 | −2.322 |
| 28 | LEU | HB2 | 7.934 | −1.155 | −2.004 |
| 28 | LEU | CG | 6.803 | 0.435 | −1.064 |
| 28 | LEU | HG | 7.002 | 1.418 | −0.596 |
| 28 | LEU | CD1 | 5.909 | 0.683 | −2.295 |
| 28 | LEU | HD11 | 5.692 | −0.251 | −2.848 |
| 28 | LEU | HD12 | 4.935 | 1.125 | −2.018 |
| 28 | LEU | HD13 | 6.384 | 1.382 | −3.009 |
| 28 | LEU | CD2 | 6.044 | −0.436 | −0.042 |
| 28 | LEU | HD21 | 5.068 | 0.007 | 0.230 |
| 28 | LEU | HD22 | 5.844 | −1.452 | −0.431 |
| 28 | LEU | HD23 | 6.607 | −0.550 | 0.901 |
| 29 | GLN | N | 11.255 | −0.816 | −1.925 |
| 29 | GLN | CA | 12.406 | −1.595 | −2.475 |
| 29 | GLN | HN | 11.082 | 0.162 | −2.182 |
| 29 | GLN | HA | 11.991 | −2.584 | −2.755 |
| 29 | GLN | C | 13.567 | −1.934 | −1.484 |
| 29 | GLN | O | 14.147 | −3.014 | −1.607 |
| 29 | GLN | CB | 12.883 | −1.003 | −3.833 |
| 29 | GLN | HB1 | 13.599 | −1.706 | −4.301 |
| 29 | GLN | HB2 | 12.019 | −1.021 | −4.524 |
| 29 | GLN | CG | 13.475 | 0.432 | −3.883 |
| 29 | GLN | HG1 | 12.803 | 1.117 | −3.337 |
| 29 | GLN | HG2 | 13.438 | 0.795 | −4.926 |
| 29 | GLN | CD | 14.910 | 0.617 | −3.360 |
| 29 | GLN | OE1 | 15.141 | 1.212 | −2.310 |
| 29 | GLN | NE2 | 15.908 | 0.140 | −4.084 |
| 29 | GLN | HE21 | 15.657 | −0.353 | −4.946 |
| 29 | GLN | HE22 | 16.847 | 0.271 | −3.695 |
| 30 | ASN | N | 13.883 | −1.064 | −0.500 |
| 30 | ASN | CA | 14.859 | −1.363 | 0.589 |
| 30 | ASN | HN | 13.357 | −0.182 | −0.525 |
| 30 | ASN | HA | 15.789 | −1.718 | 0.103 |
| 30 | ASN | C | 14.394 | −2.487 | 1.576 |
| 30 | ASN | O | 15.180 | −3.393 | 1.865 |
| 30 | ASN | CB | 15.209 | −0.024 | 1.297 |
| 30 | ASN | HB1 | 14.313 | 0.381 | 1.811 |
| 30 | ASN | HB2 | 15.459 | 0.741 | 0.538 |
| 30 | ASN | CG | 16.411 | −0.079 | 2.257 |
| 30 | ASN | OD1 | 17.565 | −0.101 | 1.835 |
| 30 | ASN | ND2 | 16.175 | −0.094 | 3.557 |
| 30 | ASN | HD21 | 15.192 | −0.090 | 3.848 |
| 30 | ASN | HD22 | 17.001 | −0.122 | 4.163 |
| 31 | LEU | N | 13.133 | −2.449 | 2.059 |
| 31 | LEU | CA | 12.510 | −3.577 | 2.815 |
| 31 | LEU | HN | 12.579 | −1.645 | 1.742 |
| 31 | LEU | HA | 13.171 | −3.801 | 3.673 |
| 31 | LEU | C | 12.370 | −4.919 | 2.020 |
| 31 | LEU | O | 12.617 | −5.979 | 2.598 |
| 31 | LEU | CB | 11.135 | −3.137 | 3.397 |
| 31 | LEU | HB1 | 10.484 | −2.835 | 2.550 |
| 31 | LEU | HB2 | 10.622 | −4.020 | 3.828 |
| 31 | LEU | CG | 11.136 | −2.012 | 4.471 |
| 31 | LEU | HG | 11.710 | −1.150 | 4.082 |
| 31 | LEU | CD1 | 9.702 | −1.513 | 4.733 |
| 31 | LEU | HD11 | 9.051 | −2.309 | 5.141 |
| 31 | LEU | HD12 | 9.685 | −0.673 | 5.453 |
| 31 | LEU | HD13 | 9.225 | −1.143 | 3.806 |
| 31 | LEU | CD2 | 11.790 | −2.446 | 5.800 |
| 31 | LEU | HD21 | 11.766 | −1.636 | 6.552 |
| 31 | LEU | HD22 | 11.283 | −3.323 | 6.245 |
| 31 | LEU | HD23 | 12.853 | −2.715 | 5.665 |
| 32 | PHE | N | 12.006 | −4.880 | 0.720 |
| 32 | PHE | CA | 11.945 | −6.085 | −0.153 |
| 32 | PHE | HN | 11.808 | −3.940 | 0.359 |
| 32 | PHE | HA | 11.330 | −6.832 | 0.380 |
| 32 | PHE | C | 13.325 | −6.763 | −0.442 |
| 32 | PHE | O | 13.428 | −7.981 | −0.273 |
| 32 | PHE | CB | 11.156 | −5.718 | −1.445 |
| 32 | PHE | HB1 | 10.236 | −5.162 | −1.176 |
| 32 | PHE | HB2 | 11.739 | −4.989 | −2.041 |
| 32 | PHE | CG | 10.748 | −6.916 | −2.322 |
| 32 | PHE | CD1 | 11.529 | −7.286 | −3.422 |
| 32 | PHE | HD1 | 12.424 | −6.733 | −3.671 |
| 32 | PHE | CD2 | 9.607 | −7.664 | −2.009 |
| 32 | PHE | HD2 | 8.994 | −7.398 | −1.160 |
| 32 | PHE | CE1 | 11.181 | −8.394 | −4.190 |
| 32 | PHE | HE1 | 11.800 | −8.686 | −5.026 |
| 32 | PHE | CE2 | 9.262 | −8.773 | −2.778 |
| 32 | PHE | HE2 | 8.387 | −9.355 | −2.525 |
| 32 | PHE | CZ | 10.049 | −9.138 | −3.867 |
| 32 | PHE | HZ | 9.787 | −10.004 | −4.457 |
| 33 | ILE | N | 14.353 | −6.004 | −0.883 |
| 33 | ILE | CA | 15.663 | −6.564 | −1.345 |
| 33 | ILE | HN | 14.134 | −5.006 | −0.980 |
| 33 | ILE | HA | 15.384 | −7.289 | −2.133 |
| 33 | ILE | C | 16.495 | −7.409 | −0.317 |
| 33 | ILE | O | 17.181 | −8.344 | −0.739 |
| 33 | ILE | CB | 16.489 | −5.449 | −2.086 |
| 33 | ILE | HB | 15.776 | −4.903 | −2.735 |
| 33 | ILE | CG1 | 17.557 | −6.044 | −3.052 |
| 33 | ILE | HG11 | 17.119 | −6.899 | −3.603 |
| 33 | ILE | HG12 | 18.393 | −6.481 | −2.473 |
| 33 | ILE | CG2 | 17.113 | −4.397 | −1.130 |
| 33 | ILE | HG21 | 17.525 | −3.530 | −1.679 |
| 33 | ILE | HG22 | 16.366 | −3.996 | −0.425 |
| 33 | ILE | HG23 | 17.934 | −4.823 | −0.524 |
| 33 | ILE | CD1 | 18.119 | −5.067 | −4.098 |
| 33 | ILE | HD11 | 17.319 | −4.642 | −4.731 |
| 33 | ILE | HD12 | 18.660 | −4.224 | −3.631 |
| 33 | ILE | HD13 | 18.834 | −5.575 | −4.772 |

TABLE III-continued

Orthogonal three dimensional coordinates on Ångströms for the phospholamban (1–36) peptide (SEQ ID NO:9)

| Residue | Atom | X | Y | Z |
|---|---|---|---|---|
| 34 | ASN | N | 16.432 | −7.113 | 1.000 |
| 34 | ASN | CA | 17.066 | −7.958 | 2.057 |
| 34 | ASN | HN | 15.817 | −6.323 | 1.227 |
| 34 | ASN | HA | 18.139 | −8.016 | 1.783 |
| 34 | ASN | C | 16.596 | −9.450 | 2.131 |
| 34 | ASN | O | 17.449 | −10.334 | 2.262 |
| 34 | ASN | CB | 17.063 | −7.233 | 3.433 |
| 34 | ASN | HB1 | 17.629 | −7.850 | 4.158 |
| 34 | ASN | HB2 | 17.675 | −6.313 | 3.346 |
| 34 | ASN | CG | 15.701 | −6.904 | 4.084 |
| 34 | ASN | OD1 | 14.944 | −7.786 | 4.489 |
| 34 | ASN | ND2 | 15.366 | −5.635 | 4.221 |
| 34 | ASN | HD21 | 16.007 | −4.942 | 3.822 |
| 34 | ASN | HD22 | 14.441 | −5.462 | 4.626 |
| 35 | PHE | N | 15.282 | −9.732 | 2.018 |
| 35 | PHE | CA | 14.756 | −11.120 | 1.861 |
| 35 | PHE | HN | 14.679 | −8.909 | 1.899 |
| 35 | PHE | HA | 15.444 | −11.796 | 2.407 |
| 35 | PHE | C | 14.743 | −11.669 | 0.395 |
| 35 | PHE | O | 15.062 | −12.848 | 0.209 |
| 35 | PHE | CB | 13.404 | −11.302 | 2.611 |
| 35 | PHE | HB1 | 13.580 | −11.112 | 3.689 |
| 35 | PHE | HB2 | 13.142 | −12.378 | 2.592 |
| 35 | PHE | CG | 12.173 | −10.489 | 2.152 |
| 35 | PHE | CD1 | 11.351 | −10.970 | 1.126 |
| 35 | PHE | HD1 | 11.594 | −11.891 | 0.615 |
| 35 | PHE | CD2 | 11.830 | −9.300 | 2.804 |
| 35 | PHE | HD2 | 12.449 | −8.910 | 3.599 |
| 35 | PHE | CE1 | 10.209 | −10.267 | 0.752 |
| 35 | PHE | HE1 | 9.583 | −10.638 | −0.047 |
| 35 | PHE | CE2 | 10.675 | −8.610 | 2.442 |
| 35 | PHE | HE2 | 10.412 | −7.694 | 2.952 |
| 35 | PHE | CZ | 9.867 | −9.092 | 1.417 |
| 35 | PHE | HZ | 8.977 | −8.551 | 1.131 |
| 36 | CYS | N | 14.361 | −10.862 | −0.617 |
| 36 | CYS | CA | 14.287 | −11.298 | −2.032 |
| 36 | CYS | C | 14.877 | −10.182 | −2.921 |
| 36 | CYS | O | 16.060 | −10.297 | −3.312 |
| 36 | CYS | CB | 12.828 | −11.666 | −2.386 |
| 36 | CYS | SG | 12.713 | −12.287 | −4.099 |
| 36 | CYS | OXT | 14.177 | −9.193 | −3.237 |
| 36 | CYS | HN | 14.138 | −9.897 | −0.344 |
| 36 | CYS | HA | 14.907 | −12.202 | −2.195 |
| 36 | CYS | HB1 | 12.450 | −12.455 | −1.710 |
| 36 | CYS | HB2 | 12.149 | −10.800 | −2.263 |
| 36 | CYS | HG | 12.819 | −11.106 | −4.704 |
| END | | | | | |

TABLE IV

Orthogonal three dimensional coordinates in Ångströms for the cP226 · phospholamban (1–36) complex

| Residue | Atom | X | Y | Z |
|---|---|---|---|---|
| 1 | MET | N | −18.366 | −10.441 | 5.382 |
| 1 | MET | CA | −16.968 | −10.052 | 5.756 |
| 1 | MET | HN1 | −18.363 | −11.296 | 4.808 |
| 1 | MET | HN2 | −18.964 | −10.642 | 6.192 |
| 1 | MET | HN3 | −18.836 | −9.728 | 4.811 |
| 1 | MET | HA | −17.022 | −9.109 | 6.345 |
| 1 | MET | C | −16.058 | −9.653 | 4.544 |
| 1 | MET | O | −15.491 | −8.562 | 4.547 |
| 1 | MET | CB | −16.367 | −11.107 | 6.732 |
| 1 | MET | HB1 | −15.418 | −10.692 | 7.133 |
| 1 | MET | HB2 | −16.999 | −11.196 | 7.638 |
| 1 | MET | CG | −16.048 | −12.534 | 6.208 |
| 1 | MET | SD | −17.501 | −13.438 | 5.624 |
| 1 | MET | CE | −18.199 | −13.998 | 7.185 |
| 1 | MET | HG1 | −15.303 | −12.501 | 5.387 |

TABLE IV-continued

Orthogonal three dimensional coordinates in Ångströms for the cP226 · phospholamban (1–36) complex

| Residue | Atom | X | Y | Z |
|---|---|---|---|---|
| 1 | MET | HG2 | −15.555 | −13.137 | 6.997 |
| 1 | MET | HE1 | −19.124 | −14.578 | 7.010 |
| 1 | MET | HE2 | −17.490 | −14.662 | 7.714 |
| 1 | MET | HE3 | −18.445 | −13.157 | 7.857 |
| 2 | GLU | N | −15.964 | −10.507 | 3.518 |
| 2 | GLU | CA | −15.197 | −10.254 | 2.269 |
| 2 | GLU | HN | −16.431 | −11.415 | 3.613 |
| 2 | GLU | HA | −14.384 | −9.526 | 2.462 |
| 2 | GLU | C | −16.086 | −9.579 | 1.149 |
| 2 | GLU | O | −16.809 | −8.614 | 1.422 |
| 2 | GLU | CB | −14.496 | −11.624 | 1.943 |
| 2 | GLU | CG | −15.304 | −12.969 | 1.947 |
| 2 | GLU | CD | −16.679 | −12.989 | 1.312 |
| 2 | GLU | OE1 | −16.770 | −13.228 | 0.092 |
| 2 | GLU | OE2 | −17.689 | −12.746 | 2.009 |
| 2 | GLU | HB1 | −13.980 | −11.532 | 0.967 |
| 2 | GLU | HB2 | −13.654 | −11.750 | 2.652 |
| 2 | GLU | HG1 | −14.713 | −13.761 | 1.451 |
| 2 | GLU | HG2 | −15.430 | −13.335 | 2.980 |
| 3 | LYS | N | −16.030 | −10.063 | −0.108 |
| 3 | LYS | CA | −16.999 | −9.726 | −1.196 |
| 3 | LYS | HN | −15.594 | −10.995 | −0.096 |
| 3 | LYS | HA | −16.597 | −10.266 | −2.076 |
| 3 | LYS | C | −16.983 | −8.231 | −1.670 |
| 3 | LYS | O | −16.139 | −7.854 | −2.488 |
| 3 | LYS | CB | −18.379 | −10.400 | −0.889 |
| 3 | LYS | CG | −19.212 | −10.831 | −2.119 |
| 3 | LYS | CD | −20.381 | −11.791 | −1.776 |
| 3 | LYS | CE | −20.044 | −13.300 | −1.688 |
| 3 | LYS | NZ | −19.369 | −13.685 | −0.411 |
| 3 | LYS | HB1 | −18.203 | −11.293 | −0.268 |
| 3 | LYS | HB2 | −18.978 | −9.753 | −0.222 |
| 3 | LYS | HG1 | −19.611 | −9.917 | −2.608 |
| 3 | LYS | HG2 | −18.563 | −11.290 | −2.893 |
| 3 | LYS | HD1 | −20.925 | −11.444 | −0.874 |
| 3 | LYS | HD2 | −21.132 | −11.674 | −2.584 |
| 3 | LYS | HE1 | −20.986 | −13.883 | −1.807 |
| 3 | LYS | HE2 | −19.429 | −13.605 | −2.567 |
| 3 | LYS | HZ1 | −18.360 | −13.394 | −0.340 |
| 3 | LYS | HZ2 | −19.747 | −13.259 | 0.445 |
| 3 | LYS | HZ3 | −19.300 | −14.692 | −0.225 |
| 4 | VAL | N | −17.850 | −7.370 | −1.113 |
| 4 | VAL | CA | −17.729 | −5.883 | −1.250 |
| 4 | VAL | HN | −18.368 | −7.786 | −0.332 |
| 4 | VAL | HA | −17.617 | −5.678 | −2.335 |
| 4 | VAL | C | −16.444 | −5.249 | −0.593 |
| 4 | VAL | O | −15.841 | −4.361 | −1.194 |
| 4 | VAL | CB | −19.085 | −5.211 | −0.839 |
| 4 | VAL | HB | −19.895 | −5.756 | −1.368 |
| 4 | VAL | CG1 | −19.192 | −3.746 | −1.314 |
| 4 | VAL | HG11 | −20.191 | −3.313 | −1.113 |
| 4 | VAL | HG12 | −18.450 | −3.089 | −0.822 |
| 4 | VAL | HG13 | −19.028 | −3.652 | −2.405 |
| 4 | VAL | CG2 | −19.423 | −5.252 | 0.671 |
| 4 | VAL | HG21 | −20.429 | −4.840 | 0.877 |
| 4 | VAL | HG22 | −19.412 | −6.281 | 1.073 |
| 4 | VAL | HG23 | −18.707 | −4.660 | 1.273 |
| 5 | GLN | N | −15.991 | −5.716 | 0.586 |
| 5 | GLN | CA | −14.681 | −5.298 | 1.177 |
| 5 | GLN | HN | −16.525 | −6.517 | 0.946 |
| 5 | GLN | HA | −14.601 | −4.196 | 1.093 |
| 5 | GLN | C | −13.383 | −5.831 | 0.471 |
| 5 | GLN | O | −12.357 | −5.141 | 0.491 |
| 5 | GLN | CB | −14.696 | −5.643 | 2.692 |
| 5 | GLN | HB1 | −13.684 | −5.487 | 3.116 |
| 5 | GLN | HB2 | −14.878 | −6.728 | 2.817 |
| 5 | GLN | CG | −15.703 | −4.852 | 3.575 |
| 5 | GLN | HG1 | −16.738 | −4.985 | 3.209 |
| 5 | GLN | HG2 | −15.711 | −5.300 | 4.586 |
| 5 | GLN | CD | −15.396 | −3.363 | 3.762 |
| 5 | GLN | OE1 | −14.647 | −2.963 | 4.642 |
| 5 | GLN | NE2 | −15.948 | −2.495 | 2.953 |
| 5 | GLN | HE21 | −15.630 | −1.536 | 3.116 |
| 5 | GLN | HE22 | −16.412 | −2.871 | 2.123 |

TABLE IV-continued

Orthogonal three dimensional coordinates in
Ångstroms for the cP226 · phospholamban (1–36) complex

| Residue | Atom | X | Y | Z |
|---|---|---|---|---|
| 6 | TYR | N | -13.412 | -7.004 | -0.197 |
| 6 | TYR | CA | -12.392 | -7.346 | -1.233 |
| 6 | TYR | HN | -14.349 | -7.420 | -0.207 |
| 6 | TYR | HA | -11.396 | -7.186 | -0.771 |
| 6 | TYR | C | -12.416 | -6.413 | -2.498 |
| 6 | TYR | O | -11.364 | -5.894 | -2.875 |
| 6 | TYR | CB | -12.491 | -8.863 | -1.566 |
| 6 | TYR | HB1 | -12.592 | -9.455 | -0.636 |
| 6 | TYR | HB2 | -13.426 | -9.070 | -2.123 |
| 6 | TYR | CG | -11.270 | -9.381 | -2.345 |
| 6 | TYR | CD1 | -10.084 | -9.668 | -1.661 |
| 6 | TYR | HD1 | -10.045 | -9.609 | -0.583 |
| 6 | TYR | CD2 | -11.292 | -9.461 | -3.742 |
| 6 | TYR | HD2 | -12.200 | -9.241 | -4.287 |
| 6 | TYR | CE1 | -8.932 | -10.001 | -2.366 |
| 6 | TYR | HE1 | -8.027 | -10.232 | -1.830 |
| 6 | TYR | CE2 | -10.131 | -9.785 | -4.444 |
| 6 | TYR | HE2 | -10.139 | -9.832 | -5.524 |
| 6 | TYR | CZ | -8.947 | -10.036 | -3.755 |
| 6 | TYR | OH | -7.791 | -10.280 | -4.452 |
| 6 | TYR | HH | -7.019 | -10.219 | -3.861 |
| 7 | LEU | N | -13.587 | -6.154 | -3.113 |
| 7 | LEU | CA | -13.759 | -5.074 | -4.135 |
| 7 | LEU | HN | -14.394 | -6.657 | -2.722 |
| 7 | LEU | HA | -13.139 | -5.360 | -5.005 |
| 7 | LEU | C | -13.271 | -3.631 | -3.733 |
| 7 | LEU | O | -12.609 | -2.977 | -4.542 |
| 7 | LEU | CB | -15.245 | -5.133 | -4.594 |
| 7 | LEU | HB1 | -15.523 | -6.180 | -4.824 |
| 7 | LEU | HB2 | -15.880 | -4.860 | -3.731 |
| 7 | LEU | CG | -15.651 | -4.252 | -5.804 |
| 7 | LEU | HG | -15.360 | -3.200 | -5.603 |
| 7 | LEU | CD1 | -17.176 | -4.286 | -5.987 |
| 7 | LEU | HD11 | -17.553 | -5.304 | -6.199 |
| 7 | LEU | HD12 | -17.706 | -3.921 | -5.088 |
| 7 | LEU | HD13 | -17.502 | -3.639 | -6.825 |
| 7 | LEU | CD2 | -14.975 | -4.703 | -7.111 |
| 7 | LEU | HD21 | -15.191 | -5.760 | -7.352 |
| 7 | LEU | HD22 | -15.308 | -4.098 | -7.975 |
| 7 | LEU | HD23 | -13.876 | -4.592 | -7.065 |
| 8 | THR | N | -13.511 | -3.164 | -2.491 |
| 8 | THR | CA | -12.882 | -1.929 | -1.922 |
| 8 | THR | HN | -14.206 | -3.711 | -1.961 |
| 8 | THR | HA | -13.236 | -1.074 | -2.530 |
| 8 | THR | C | -11.312 | -1.892 | -2.013 |
| 8 | THR | O | -10.767 | -0.964 | -2.613 |
| 8 | THR | CB | -13.426 | -1.715 | 0.469 |
| 8 | THR | OG1 | -14.849 | -1.671 | -0.441 |
| 8 | THR | HB | -13.095 | -2.565 | 0.160 |
| 8 | THR | HG1 | -15.101 | -0.841 | -0.857 |
| 8 | THR | CG2 | -12.988 | -0.414 | 0.216 |
| 8 | THR | HG21 | -13.230 | 0.484 | -0.384 |
| 8 | THR | HG22 | -13.473 | -0.292 | 1.203 |
| 8 | THR | HG23 | -11.898 | -0.399 | 0.403 |
| 9 | ARG | N | -10.582 | -2.897 | -1.486 |
| 9 | ARG | CA | -9.100 | -2.999 | -1.688 |
| 9 | ARG | HN | -11.154 | -3.657 | -1.099 |
| 9 | ARG | HA | -8.665 | -2.002 | -1.470 |
| 9 | ARG | C | -8.597 | -3.341 | -3.141 |
| 9 | ARG | O | -7.489 | -2.943 | -3.504 |
| 9 | ARG | CB | -8.480 | -3.985 | -0.662 |
| 9 | ARG | CG | -8.679 | -3.663 | 0.845 |
| 9 | ARG | CD | -7.677 | -4.331 | 1.815 |
| 9 | ARG | NE | -7.723 | -5.828 | 1.787 |
| 9 | ARG | CZ | -6.925 | -6.617 | 1.073 |
| 9 | ARG | NH1 | -7.116 | -7.891 | 1.115 |
| 9 | ARG | NH2 | -5.961 | -6.190 | 0.314 |
| 9 | ARG | HB1 | -7.392 | -4.020 | -0.865 |
| 9 | ARG | HB2 | -8.843 | -5.012 | -0.870 |
| 9 | ARG | HG1 | -8.611 | -2.565 | 0.992 |
| 9 | ARG | HG2 | -9.719 | -3.911 | 1.140 |
| 9 | ARG | HD1 | -6.654 | -3.934 | 1.650 |
| 9 | ARG | HD2 | -7.914 | -3.993 | 2.846 |
| 9 | ARG | HE | -8.426 | -6.349 | 2.319 |
| 9 | ARG | HH12 | -7.864 | -8.264 | 1.693 |
| 9 | ARG | HH11 | -6.571 | -8.401 | 0.386 |
| 9 | ARG | HH21 | -5.791 | -5.188 | 0.334 |
| 9 | ARG | HH22 | -5.373 | -6.910 | -0.147 |
| 10 | SER | N | -9.350 | -4.086 | -3.965 |
| 10 | SER | CA | -9.062 | -4.255 | -5.423 |
| 10 | SER | HN | -10.216 | -4.451 | -3.541 |
| 10 | SER | HA | -7.998 | -4.514 | -5.543 |
| 10 | SER | C | -9.237 | -2.985 | -6.326 |
| 10 | SER | O | -8.384 | -2.744 | -7.184 |
| 10 | SER | CB | -9.828 | -5.503 | -5.913 |
| 10 | SER | OG | -9.313 | -6.678 | -5.275 |
| 10 | SER | HB1 | -10.914 | -5.399 | -5.724 |
| 10 | SER | HB2 | -9.719 | -5.609 | -7.011 |
| 10 | SER | HG | -9.884 | -7.422 | -5.502 |
| 11 | ALA | N | -10.260 | -2.142 | -6.107 |
| 11 | ALA | CA | -10.294 | -0.755 | -6.648 |
| 11 | ALA | HN | -10.941 | -2.461 | -5.403 |
| 11 | ALA | HA | -10.105 | -0.797 | -7.740 |
| 11 | ALA | C | -9.225 | 0.239 | -6.059 |
| 11 | ALA | O | -8.524 | 0.906 | -6.827 |
| 11 | ALA | CB | -11.743 | -0.266 | -6.454 |
| 11 | ALA | HB1 | -12.024 | -0.198 | -5.385 |
| 11 | ALA | HB2 | -11.891 | 0.739 | -6.892 |
| 11 | ALA | HB3 | -12.479 | -0.934 | -6.942 |
| 12 | ILE | N | -9.063 | 0.325 | -4.722 |
| 12 | ILE | CA | -8.073 | 1.248 | -4.069 |
| 12 | ILE | HN | -9.733 | -0.232 | -4.175 |
| 12 | ILE | HA | -8.213 | 2.243 | -4.537 |
| 12 | ILE | C | -6.563 | 0.911 | -4.365 |
| 12 | ILE | O | -5.785 | 1.854 | -4.502 |
| 12 | ILE | CB | -8.421 | 1.468 | -2.546 |
| 12 | ILE | HB | -8.473 | 0.468 | -2.073 |
| 12 | ILE | CG1 | -9.804 | 2.172 | -2.347 |
| 12 | ILE | HG11 | -10.558 | 1.710 | -3.012 |
| 12 | ILE | HG12 | -9.748 | 3.226 | -2.688 |
| 12 | ILE | CG2 | -7.349 | 2.290 | -1.770 |
| 12 | ILE | HG21 | -7.590 | 2.410 | -0.699 |
| 12 | ILE | HG22 | -6.350 | 1.816 | -1.796 |
| 12 | ILE | HG23 | -7.222 | 3.309 | -2.187 |
| 12 | ILE | CD1 | -10.379 | 2.121 | -0.921 |
| 12 | ILE | HD11 | -11.413 | 2.512 | -0.890 |
| 12 | ILE | HD12 | -10.405 | 1.088 | -0.531 |
| 12 | ILE | KD13 | -9.790 | 2.730 | -0.211 |
| 13 | ARG | N | -6.116 | -0.357 | -4.492 |
| 13 | ARG | CA | -4.688 | -0.677 | -4.826 |
| 13 | ARG | HN | -6.837 | -1.075 | -4.352 |
| 13 | ARG | HA | 4.087 | -0.227 | -4.011 |
| 13 | ARG | C | -4.064 | -0.040 | -6.124 |
| 13 | ARG | O | -2.892 | 0.342 | -6.094 |
| 13 | ARG | CB | -4.446 | -2.208 | 4.706 |
| 13 | ARG | CG | -4.985 | -3.125 | -5.840 |
| 13 | ARG | CD | -4.694 | -4.625 | -5.629 |
| 13 | ARG | NE | -5.635 | -5.210 | -4.631 |
| 13 | ARG | CZ | -5.642 | -6.473 | -4.222 |
| 13 | ARG | NH1 | -4.693 | -7.326 | -4.456 |
| 13 | ARG | NH2 | -6.651 | -6.890 | -3.537 |
| 13 | ARG | HB1 | -4.825 | -2.556 | -3.726 |
| 13 | ARG | HB2 | -3.351 | -2.360 | -4.640 |
| 13 | ARG | HG1 | -6.065 | -2.948 | -6.011 |
| 13 | ARG | HG2 | -4.505 | -2.820 | -6.792 |
| 13 | ARG | HD1 | -4.788 | -5.161 | -6.598 |
| 13 | ARG | HD2 | -3.634 | -4.753 | -5.333 |
| 13 | ARG | HE | -6.427 | -4.657 | -4.281 |
| 13 | ARG | HH12 | -3.840 | -6.971 | -4.905 |
| 13 | ARG | HH11 | -4.827 | -8.262 | -4.029 |
| 13 | ARG | HH21 | -7.482 | -6.302 | -3.505 |
| 13 | ARG | HH22 | -6.560 | -7.869 | -3.213 |
| 14 | ARG | N | -4.825 | 0.102 | -7.229 |
| 14 | ARG | CA | -4.376 | 0.917 | -8.401 |
| 14 | ARG | HN | -5.808 | -0.154 | -7.074 |
| 14 | ARG | HA | -3.272 | 0.844 | -8.428 |
| 14 | ARG | C | -4.656 | 2.464 | -8.334 |
| 14 | ARG | O | -3.866 | 3.230 | -8.890 |

TABLE IV-continued

Orthogonal three dimensional coordinates in
Ångstroms for the cP226 · phospholamban (1–36) complex

| Residue | | Atom | X | Y | Z |
|---|---|---|---|---|---|
| 14 | ARG | CB | −4.845 | 0.244 | −9.719 |
| 14 | ARG | CG | −4.019 | 0.701 | −10.958 |
| 14 | ARG | CD | −4.063 | −0.202 | −12.216 |
| 14 | ARG | NE | −3.844 | −1.670 | −12.010 |
| 14 | ARG | CZ | −2.795 | −2.247 | −11.427 |
| 14 | ARG | NH1 | −1.732 | −1.615 | −11.038 |
| 14 | ARG | NH2 | −2.842 | −3.520 | −11.225 |
| 14 | ARG | HB1 | −4.739 | −0.853 | −9.604 |
| 14 | ARG | HB2 | −5.927 | 0.412 | −9.882 |
| 14 | ARG | HG1 | −4.336 | 1.727 | −11.239 |
| 14 | ARG | HG2 | −2.961 | 0.842 | −10.667 |
| 14 | ARG | HD1 | −5.052 | −0.063 | −12.698 |
| 14 | ARG | HD2 | −3.349 | 0.185 | −12.973 |
| 14 | ARG | HE | −4.569 | −2.354 | −12.237 |
| 14 | ARG | HH12 | −1.739 | −0.612 | −11.189 |
| 14 | ARG | HH11 | −1.056 | −2.146 | −10.443 |
| 14 | ARG | HH21 | −3.658 | −4.047 | −11.522 |
| 14 | ARG | HH22 | −2.019 | −3.907 | −10.697 |
| 15 | ALA | N | −5.709 | 2.944 | −7.642 |
| 15 | ALA | CA | −5.801 | 4.374 | −7.222 |
| 15 | ALA | HN | −6.269 | 2.220 | −7.179 |
| 15 | ALA | HA | −5.765 | 5.005 | −8.134 |
| 15 | ALA | C | −4.644 | 4.893 | −6.290 |
| 15 | ALA | O | −4.074 | 5.946 | −6.571 |
| 15 | ALA | CB | −7.199 | 4.561 | −6.603 |
| 15 | ALA | HB1 | −7.394 | 5.627 | −6.376 |
| 15 | ALA | HB2 | −8.010 | 4.227 | −7.279 |
| 15 | ALA | HB3 | −7.305 | 4.011 | −5.651 |
| 16 | SER | N | −4.250 | 4.134 | −5.248 |
| 16 | SER | CA | −3.106 | 4.482 | −4.352 |
| 16 | SER | HN | −4.848 | 3.315 | −5.069 |
| 16 | SER | HA | −3.235 | 5.535 | −4.049 |
| 16 | SER | C | −1.638 | 4.397 | −4.935 |
| 16 | SER | O | −0.702 | 4.880 | −4.297 |
| 16 | SER | CB | −3.324 | 3.676 | −3.050 |
| 16 | SER | OG | −2.393 | 4.057 | −2.031 |
| 16 | SER | HB1 | −3.255 | 2.589 | −3.240 |
| 16 | SER | HB2 | −4.345 | 3.849 | −2.656 |
| 16 | SER | HG | −2.450 | 5.037 | −1.916 |
| 17 | THR | N | −1.403 | 3.876 | −6.157 |
| 17 | THR | CA | −0.201 | 4.263 | −6.976 |
| 17 | THR | HN | −2.258 | 3.512 | −6.589 |
| 17 | THR | HA | 0.636 | 4.460 | −6.276 |
| 17 | THR | C | −0.319 | 5.601 | −7.802 |
| 17 | THR | O | 0.712 | 6.218 | −8.084 |
| 17 | THR | CB | 0.310 | 3.069 | −7.842 |
| 17 | THR | OG1 | 1.531 | 3.425 | −8.481 |
| 17 | THR | HB | 0.520 | 2.218 | −7.163 |
| 17 | THR | HG1 | 1.382 | 4.296 | −8.872 |
| 17 | THR | CG2 | −0.615 | 2.566 | −8.957 |
| 17 | THR | HG21 | −0.136 | 1.754 | −9.534 |
| 17 | THR | HG22 | −1.545 | 2.157 | −8.534 |
| 17 | THR | HG23 | −0.896 | 3.364 | −9.669 |
| 18 | ILE | N | −1.523 | 6.028 | −8.226 |
| 18 | ILE | CA | −1.764 | 7.358 | −8.891 |
| 18 | ILE | HN | −2.302 | 5.493 | −7.824 |
| 18 | ILE | HA | −0.928 | 7.554 | −9.592 |
| 18 | ILE | C | −1.733 | 8.562 | −7.864 |
| 18 | ILE | O | −1.063 | 9.563 | −8.116 |
| 18 | ILE | CB | −3.077 | 7.284 | −9.765 |
| 18 | ILE | HB | −3.906 | 7.053 | −9.065 |
| 18 | ILE | CG1 | −3.060 | 6.171 | −10.865 |
| 18 | ILE | HG11 | −2.576 | 5.258 | −10.472 |
| 18 | ILE | HG12 | −2.417 | 6.477 | −11.714 |
| 18 | ILE | CG2 | −3.416 | 8.637 | −10.450 |
| 18 | ILE | HG21 | −3.540 | 9.455 | −9.715 |
| 18 | ILE | HG22 | −2.626 | 8.959 | −11.154 |
| 18 | ILE | HG23 | −4.364 | 8.600 | −11.016 |
| 18 | ILE | CD1 | −4.448 | 5.738 | −11.380 |
| 18 | ILE | HD11 | −4.987 | 6.560 | −11.884 |
| 18 | ILE | HD12 | −4.365 | 4.911 | −12.110 |
| 18 | ILE | HD13 | −5.090 | 5.375 | −10.555 |
| 19 | GLU | N | −2.426 | 8.437 | −6.718 |
| 19 | GLU | CA | −2.209 | 9.220 | −5.456 |
| 19 | GLU | HN | −2.954 | 7.556 | −6.669 |
| 19 | GLU | HA | −2.898 | 10.084 | −5.466 |
| 19 | GLU | C | −0.786 | 9.777 | −5.056 |
| 19 | GLU | O | −0.692 | 10.794 | −4.362 |
| 19 | GLU | CB | −2.714 | 8.196 | −4.390 |
| 19 | GLU | CG | −2.806 | 8.605 | −2.896 |
| 19 | GLU | CD | −3.194 | 7.442 | −1.992 |
| 19 | GLU | OE1 | −2.326 | 6.599 | −1.686 |
| 19 | GLU | OE2 | −4.375 | 7.339 | −1.613 |
| 19 | GLU | HB1 | −3.720 | 7.818 | −4.667 |
| 19 | GLU | HB2 | −2.044 | 7.314 | −4.436 |
| 19 | GLU | HG1 | −1.845 | 8.993 | −2.521 |
| 19 | GLU | HG2 | −3.546 | 9.409 | −2.747 |
| 20 | MET | N | 0.304 | 9.081 | −5.411 |
| 20 | MET | CA | 1.613 | 9.205 | −4.724 |
| 20 | MET | HN | 0.064 | 8.269 | −5.989 |
| 20 | MET | HA | 1.499 | 9.758 | −3.773 |
| 20 | MET | C | 2.703 | 9.961 | −5.580 |
| 20 | MET | O | 3.391 | 9.307 | −6.372 |
| 20 | MET | CB | 2.021 | 7.758 | −4.320 |
| 20 | MET | HB1 | 1.924 | 7.072 | −5.187 |
| 20 | MET | HB2 | 3.096 | 7.734 | −4.080 |
| 20 | MET | CG | 1.245 | 7.190 | −3.111 |
| 20 | MET | SD | 1.761 | 5.508 | −2.777 |
| 20 | MET | CE | 0.862 | 5.232 | −1.245 |
| 20 | MET | HG1 | 1.366 | 7.818 | −2.209 |
| 20 | MET | HG2 | 0.155 | 7.174 | −3.311 |
| 20 | MET | HE1 | 0.982 | 4.201 | −0.876 |
| 20 | MET | HE2 | 1.153 | 5.949 | −0.457 |
| 20 | MET | HE3 | −0.219 | 5.377 | −1.430 |
| 21 | PRO | N | 2.965 | 11.301 | −5.432 |
| 21 | PRO | CA | 4.032 | 12.006 | −6.211 |
| 21 | PRO | CD | 2.094 | 12.217 | −4.662 |
| 21 | PRO | HA | 3.958 | 11.712 | −7.278 |
| 21 | PRO | HD1 | 1.931 | 11.903 | −3.614 |
| 21 | PRO | HD2 | 1.100 | 12.301 | −5.145 |
| 21 | PRO | C | 5.513 | 11.694 | −5.772 |
| 21 | PRO | O | 5.777 | 10.728 | −5.055 |
| 21 | PRO | CB | 3.558 | 13.475 | −6.078 |
| 21 | PRO | HB1 | 4.365 | 14.226 | −6.161 |
| 21 | PRO | HB2 | 2.843 | 13.707 | −6.894 |
| 21 | PRO | CG | 2.833 | 13.550 | −4.735 |
| 21 | PRO | HG1 | 2.144 | 14.412 | −4.664 |
| 21 | PRO | HG2 | 3.555 | 13.637 | −3.900 |
| 22 | GLN | N | 6.492 | 12.482 | −6.259 |
| 22 | GLN | CA | 7.971 | 12.242 | −6.117 |
| 22 | GLN | HN | 6.130 | 13.269 | −6.807 |
| 22 | GLN | HA | 8.237 | 11.652 | −7.014 |
| 22 | GLN | C | 8.571 | 11.380 | −4.938 |
| 22 | GLN | O | 9.183 | 10.336 | −5.185 |
| 22 | GLN | CB | 8.687 | 13.611 | −6.328 |
| 22 | GLN | HB1 | 9.776 | 13.432 | −6.440 |
| 22 | GLN | HB2 | 8.393 | 14.021 | −7.315 |
| 22 | GLN | CG | 8.480 | 14.719 | −5.249 |
| 22 | GLN | HG1 | 7.400 | 14.880 | −5.075 |
| 22 | GLN | HG2 | 8.893 | 14.382 | −4.280 |
| 22 | GLN | CD | 9.089 | 16.086 | −5.575 |
| 22 | GLN | OE1 | 9.447 | 16.412 | −6.700 |
| 22 | GLN | NE2 | 9.203 | 16.949 | −4.600 |
| 22 | GLN | HE21 | 8.880 | 16.664 | −3.672 |
| 22 | GLN | HE22 | 9.586 | 17.853 | −4.892 |
| 23 | GLN | N | 8.363 | 11.795 | −3.682 |
| 23 | GLN | CA | 8.769 | 11.029 | −2.462 |
| 23 | GLN | HN | 7.850 | 12.681 | −3.626 |
| 23 | GLN | HA | 9.766 | 10.583 | −2.655 |
| 23 | GLN | C | 7.858 | 9.817 | −2.049 |
| 23 | GLN | O | 8.366 | 8.773 | −1.628 |
| 23 | GLN | CB | 8.984 | 12.075 | −1.331 |
| 23 | GLN | HB1 | 9.753 | 12.795 | −1.680 |
| 23 | GLN | HB2 | 9.473 | 11.581 | −0.469 |
| 23 | GLN | CG | 7.730 | 12.848 | −0.815 |
| 23 | GLN | HG1 | 6.971 | 12.936 | −1.613 |
| 23 | GLN | HG2 | 7.219 | 12.273 | −0.019 |
| 23 | GLN | CD | 8.018 | 14.281 | −0.367 |

TABLE IV-continued

Orthogonal three dimensional coordinates in Ångströms for the cP226 · phospholamban (1–36) complex

| Residue | Atom | X | Y | Z |
|---|---|---|---|---|
| 23 | GLN | OE1 | 8.162 | 15.184 | -1.181 |
| 23 | GLN | NE2 | 8.113 | 14.540 | 0.911 |
| 23 | GLN | HE21 | 7.995 | 13.761 | 1.562 |
| 23 | GLN | HE22 | 8.301 | 15.524 | 1.123 |
| 24 | ALA | N | 6.527 | 9.922 | -2.191 |
| 24 | ALA | CA | 5.598 | 8.770 | -2.032 |
| 24 | ALA | HN | 6.246 | 10.756 | -2.719 |
| 24 | ALA | HA | 5.810 | 8.295 | -1.054 |
| 24 | ALA | C | 5.702 | 7.618 | -3.104 |
| 24 | ALA | O | 5.540 | 6.445 | -2.745 |
| 24 | ALA | CB | 4.202 | 9.401 | -1.926 |
| 24 | ALA | HB1 | 4.133 | 10.148 | -1.112 |
| 24 | ALA | HB2 | 3.901 | 9.909 | -2.861 |
| 24 | ALA | HB3 | 3.433 | 8.639 | -1.708 |
| 25 | ARG | N | 6.020 | 7.917 | -4.378 |
| 25 | ARG | CA | 6.491 | 6.901 | -5.368 |
| 25 | ARG | HN | 5.937 | 8.921 | -4.609 |
| 25 | ARG | HA | 5.870 | 6.003 | -5.211 |
| 25 | ARG | C | 7.958 | 6.348 | -5.212 |
| 25 | ARG | O | 8.226 | 5.246 | -5.698 |
| 25 | ARG | CB | 6.139 | 7.358 | -6.810 |
| 25 | ARG | CG | 6.910 | 8.577 | -7.389 |
| 25 | ARG | CD | 7.630 | 8.344 | -8.738 |
| 25 | ARG | NE | 8.675 | 7.276 | -8.682 |
| 25 | ARG | CZ | 9.882 | 7.391 | -8.144 |
| 25 | ARG | NH1 | 10.343 | 8.483 | -7.617 |
| 25 | ARG | NH2 | 10.647 | 6.350 | -8.127 |
| 25 | ARG | HB1 | 5.050 | 7.561 | -6.864 |
| 25 | ARG | HB2 | 6.250 | 6.485 | -7.481 |
| 25 | ARG | HG1 | 6.185 | 9.408 | -7.513 |
| 25 | ARG | HG2 | 7.623 | 8.968 | -6.640 |
| 25 | ARG | HD1 | 6.870 | 8.070 | -9.502 |
| 25 | ARG | HD2 | 8.049 | 9.297 | -9.123 |
| 25 | ARG | HE | 8.487 | 6.333 | -9.036 |
| 25 | ARG | HH12 | 9.678 | 9.253 | -7.562 |
| 25 | ARG | HH11 | 11.269 | 8.411 | -7.176 |
| 25 | ARG | HH21 | 10.262 | 5.474 | -8.478 |
| 25 | ARG | HH22 | 11.531 | 6.451 | -7.608 |
| 26 | GLN | N | 8.883 | 7.013 | -4.478 |
| 26 | GLN | CA | 10.024 | 6.300 | -3.813 |
| 26 | GLN | HN | 8.547 | 7.923 | -4.141 |
| 26 | GLN | HA | 10.567 | 5.729 | -4.593 |
| 26 | GLN | C | 9.557 | 5.221 | -2.773 |
| 26 | GLN | O | 9.940 | 4.063 | -2.908 |
| 26 | GLN | CB | 11.056 | 7.278 | -3.178 |
| 26 | GLN | HB1 | 10.541 | 7.954 | -2.472 |
| 26 | GLN | HB2 | 11.746 | 6.698 | -2.531 |
| 26 | GLN | CG | 11.938 | 8.128 | -4.132 |
| 26 | GLN | HG1 | 12.574 | 8.807 | -3.533 |
| 26 | GLN | HG2 | 11.290 | 8.808 | -4.715 |
| 26 | GLN | CD | 12.851 | 7.379 | -5.112 |
| 26 | GLN | OE1 | 12.666 | 7.434 | -6.322 |
| 26 | GLN | NE2 | 13.859 | 6.683 | -4.658 |
| 26 | GLN | HE21 | 13.951 | 6.566 | -3.644 |
| 26 | GLN | HE22 | 14.393 | 6.190 | -5.379 |
| 27 | LYS | N | 8.661 | 5.530 | -1.814 |
| 27 | LYS | CA | 7.965 | 4.488 | -0.985 |
| 27 | LYS | HN | 8.437 | 6.532 | -1.767 |
| 27 | LYS | HA | 8.749 | 3.968 | -0.397 |
| 27 | LYS | C | 7.205 | 3.320 | -1.738 |
| 27 | LYS | O | 6.925 | 2.294 | -1.118 |
| 27 | LYS | CB | 7.084 | 5.278 | 0.032 |
| 27 | LYS | CG | 6.375 | 4.464 | 1.151 |
| 27 | LYS | CD | 4.824 | 4.447 | 1.123 |
| 27 | LYS | CE | 4.146 | 3.508 | 0.100 |
| 27 | LYS | NZ | 4.039 | 4.152 | -1.240 |
| 27 | LYS | HB1 | 6.354 | 5.914 | -0.500 |
| 27 | LYS | HB2 | 7.736 | 6.020 | 0.539 |
| 27 | LYS | HG1 | 6.775 | 3.431 | 1.209 |
| 27 | LYS | HG2 | 6.683 | 4.897 | 2.125 |
| 27 | LYS | HD1 | 4.499 | 4.110 | 2.129 |
| 27 | LYS | HD2 | 4.421 | 5.479 | 1.064 |
| 27 | LYS | HE1 | 4.692 | 2.536 | 0.045 |
| 27 | LYS | HE2 | 3.132 | 3.226 | 0.470 |
| 27 | LYS | HZ1 | 3.433 | 4.985 | -1.252 |
| 27 | LYS | HZ2 | 4.943 | 4.472 | -1.617 |
| 27 | LYS | HZ3 | 3.653 | 3.537 | -1.972 |
| 28 | LEU | N | 6.852 | 3.447 | -3.034 |
| 28 | LEU | CA | 6.417 | 2.288 | -3.875 |
| 28 | LEU | HN | 7.273 | 4.279 | -3.462 |
| 28 | LEU | HA | 5.700 | 1.669 | -3.298 |
| 28 | LEU | C | 7.599 | 1.309 | -4.230 |
| 28 | LEU | O | 7.644 | 0.200 | -3.695 |
| 28 | LEU | CB | 5.656 | 2.809 | -5.135 |
| 28 | LEU | HB1 | 6.358 | 3.414 | -5.737 |
| 28 | LEU | HB2 | 5.429 | 1.941 | -5.788 |
| 28 | LEU | CG | 4.345 | 3.618 | -4.944 |
| 28 | LEU | HG | 4.521 | 4.455 | -4.242 |
| 28 | LEU | CD1 | 3.889 | 4.207 | -6.289 |
| 28 | LEU | HD11 | 3.626 | 3.417 | -7.017 |
| 28 | LEU | HD12 | 2.996 | 4.851 | -6.178 |
| 28 | LEU | HD13 | 4.664 | 4.825 | -6.770 |
| 28 | LEU | CD2 | 3.199 | 2.752 | -4.415 |
| 28 | LEU | HD21 | 2.261 | 3.324 | -4.268 |
| 28 | LEU | HD22 | 2.945 | 1.949 | -5.132 |
| 28 | LEU | HD23 | 3.435 | 2.251 | -3.461 |
| 29 | GLN | N | 8.551 | 1.701 | -5.102 |
| 29 | GLN | CA | 9.681 | 0.813 | -5.525 |
| 29 | GLN | HN | 8.445 | 2.659 | -5.444 |
| 29 | GLN | HA | 9.296 | -0.228 | -5.547 |
| 29 | GLN | C | 10.927 | 0.704 | -4.581 |
| 29 | GLN | O | 11.555 | -0.350 | -4.563 |
| 29 | GLN | CB | 10.058 | 1.100 | -7.008 |
| 29 | GLN | HB1 | 10.824 | 0.361 | -7.320 |
| 29 | GLN | HB2 | 9.184 | 0.826 | -7.631 |
| 29 | GLN | CG | 10.521 | 2.525 | -7.440 |
| 29 | GLN | HG1 | 9.707 | 3.243 | -7.230 |
| 29 | GLN | HG2 | 10.628 | 2.539 | -8.541 |
| 29 | GLN | CD | 11.813 | 3.109 | -6.855 |
| 29 | GLN | OE1 | 11.817 | 4.184 | -6.267 |
| 29 | GLN | NE2 | 12.940 | 2.471 | -7.031 |
| 29 | GLN | HE21 | 12.665 | 1.517 | -7.397 |
| 29 | GLN | HE22 | 13.731 | 2.870 | -6.518 |
| 30 | ASN | N | 11.300 | 1.729 | -3.796 |
| 30 | ASN | CA | 12.455 | 1.663 | -2.841 |
| 30 | ASN | HN | 10.673 | 2.543 | -3.835 |
| 30 | ASN | HA | 13.328 | 1.287 | -3.409 |
| 30 | ASN | C | 12.294 | 0.683 | -1.616 |
| 30 | ASN | O | 13.296 | 0.164 | -1.122 |
| 30 | ASN | CB | 12.777 | 3.128 | -2.412 |
| 30 | ASN | HB1 | 12.124 | 3.435 | -1.575 |
| 30 | ASN | HB2 | 12.518 | 3.827 | -3.229 |
| 30 | ASN | CG | 14.217 | 3.499 | -2.051 |
| 30 | ASN | OD1 | 14.740 | 4.505 | -2.512 |
| 30 | ASN | ND2 | 14.897 | 2.774 | -1.201 |
| 30 | ASN | HD21 | 14.495 | 1.861 | -0.955 |
| 30 | ASN | HD22 | 15.872 | 3.070 | -1.104 |
| 31 | LEU | N | 11.065 | 0.414 | -1.141 |
| 31 | LEU | CA | 10.771 | -0.779 | -0.283 |
| 31 | LEU | HN | 10.324 | 0.878 | -1.678 |
| 31 | LEU | HA | 11.547 | -0.852 | 0.505 |
| 31 | LEU | C | 10.791 | -2.187 | -0.999 |
| 31 | LEU | O | 11.021 | -3.200 | -0.334 |
| 31 | LEU | CB | 9.400 | -0.555 | 0.422 |
| 31 | LEU | HB1 | 8.613 | -0.511 | -0.357 |
| 31 | LEU | HB2 | 9.161 | -1.468 | 1.000 |
| 31 | LEU | CG | 9.234 | 0.657 | 1.379 |
| 31 | LEU | HG | 9.418 | 1.589 | 0.808 |
| 31 | LEU | CD1 | 7.793 | 0.696 | 1.913 |
| 31 | LEU | HD11 | 7.540 | -0.215 | 2.491 |
| 31 | LEU | HD12 | 7.624 | 1.560 | 2.582 |
| 31 | LEU | HD13 | 7.056 | 0.771 | 1.091 |
| 31 | LEU | CD2 | 10.205 | 0.614 | 2.572 |
| 31 | LEU | HD21 | 10.050 | 1.463 | 3.263 |
| 31 | LEU | HD22 | 10.099 | -0.315 | 3.165 |
| 31 | LEU | HD23 | 11.260 | 0.669 | 2.244 |
| 32 | PHE | N | 10.538 | -2.258 | -2.316 |
| 32 | PHE | CA | 10.696 | -3.495 | -3.136 |

TABLE IV-continued

Orthogonal three dimensional coordinates in Ångströms for the cP226 · phospholamban (1–36) complex

| Residue | | Atom | X | Y | Z |
|---|---|---|---|---|---|
| 32 | PHE | HN | 10.482 | −1.340 | −2.768 |
| 32 | PHE | HA | 10.395 | −4.364 | −2.515 |
| 32 | PHE | C | 12.179 | −3.811 | −3.566 |
| 32 | PHE | O | 12.658 | −4.914 | −3.301 |
| 32 | PHE | CB | 9.693 | −3.392 | −4.333 |
| 32 | PHE | HB1 | 9.145 | −2.429 | −4.348 |
| 32 | PHE | HB2 | 10.258 | −3.342 | −5.286 |
| 32 | PHE | CG | 8.648 | −4.516 | −4.425 |
| 32 | PHE | CD1 | 8.796 | −5.536 | −5.370 |
| 32 | PHE | HD1 | 9.665 | −5.563 | −6.012 |
| 32 | PHE | CD2 | 7.508 | −4.495 | −3.613 |
| 32 | PHE | HD2 | 7.370 | −3.707 | −2.887 |
| 32 | PHE | CE1 | 7.815 | −6.513 | −5.511 |
| 32 | PHE | HE1 | 7.935 | −7.287 | −6.256 |
| 32 | PHE | CE2 | 6.530 | −5.480 | −3.751 |
| 32 | PHE | HE2 | 5.644 | −5.463 | −3.137 |
| 32 | PHE | CZ | 6.679 | −6.481 | −4.707 |
| 32 | PHE | HZ | 5.903 | −7.220 | −4.840 |
| 33 | ILE | N | 12.931 | −2.860 | −4.163 |
| 33 | ILE | CA | 14.249 | −3.145 | −4.844 |
| 33 | ILE | HN | 12.381 | −2.034 | −4.432 |
| 33 | ILE | HA | 14.130 | −4.126 | −5.346 |
| 33 | ILE | C | 15.529 | −3.369 | −3.934 |
| 33 | ILE | O | 16.676 | −3.233 | −4.369 |
| 33 | ILE | CB | 14.418 | −2.106 | −6.019 |
| 33 | ILE | HB | 13.426 | −2.035 | −6.516 |
| 33 | ILE | CG1 | 15.384 | −2.601 | −7.135 |
| 33 | ILE | HG11 | 15.188 | −3.677 | −7.326 |
| 33 | ILE | HG12 | 16.434 | −2.566 | −6.789 |
| 33 | ILE | CG2 | 14.822 | −0.685 | −5.541 |
| 33 | ILE | HG21 | 14.801 | 0.051 | −6.363 |
| 33 | ILE | HG22 | 14.142 | −0.317 | −4.756 |
| 33 | ILE | HG23 | 15.844 | −0.676 | −5.117 |
| 33 | ILE | CD1 | 15.254 | −1.881 | −8.489 |
| 33 | ILE | HD11 | 14.229 | −1.989 | −8.896 |
| 33 | ILE | HD12 | 15.491 | −0.806 | −8.425 |
| 33 | ILE | HD13 | 15.936 | −2.326 | −9.236 |
| 34 | ASN | N | 15.344 | −3.823 | −2.688 |
| 34 | ASN | CA | 16.279 | −4.802 | −2.047 |
| 34 | ASN | HN | 14.332 | −3.912 | −2.532 |
| 34 | ASN | HA | 17.316 | −4.527 | −2.325 |
| 34 | ASN | C | 16.140 | −6.303 | −2.523 |
| 34 | ASN | O | 17.115 | −7.053 | −2.449 |
| 34 | ASN | CB | 16.199 | −4.624 | −0.503 |
| 34 | ASN | HB1 | 16.971 | −5.266 | −0.040 |
| 34 | ASN | HB2 | 16.514 | −3.598 | −0.235 |
| 34 | ASN | CG | 14.875 | −4.948 | −0.199 |
| 34 | ASN | OD1 | 14.645 | −6.042 | 0.695 |
| 34 | ASN | ND2 | 13.967 | −4.009 | 0.275 |
| 34 | ASN | HD21 | 14.152 | −3.184 | −0.301 |
| 34 | ASN | HD22 | 13.053 | −4.355 | 0.578 |
| 35 | PHE | N | 14.955 | −6.729 | −2.996 |
| 35 | PHE | CA | 14.720 | −8.055 | −3.644 |
| 35 | PHE | HN | 14.230 | −6.001 | −3.022 |
| 35 | PHE | HA | 15.681 | −8.604 | −3.688 |
| 35 | PHE | C | 14.267 | −7.997 | −5.150 |
| 35 | PHE | O | 14.703 | −8.857 | −5.922 |
| 35 | PHE | CB | 13.790 | −8.914 | −2.732 |
| 35 | PHE | HB1 | 14.297 | −9.051 | −1.757 |
| 35 | PHE | HB2 | 13.757 | −9.938 | −3.149 |
| 35 | PHE | CG | 12.346 | −8.419 | −2.481 |
| 35 | PHE | CD1 | 11.297 | −8.823 | −3.315 |
| 35 | PHE | HD1 | 11.490 | −9.463 | −4.149 |
| 35 | PHE | CD2 | 12.085 | −7.518 | −1.443 |
| 35 | PHE | HD2 | 12.890 | −7.171 | −0.812 |
| 35 | PHE | CE1 | 10.013 | −8.316 | −3.124 |
| 35 | PHE | HE1 | 9.216 | −8.591 | −3.799 |
| 35 | PHE | CE2 | 10.805 | −7.002 | −1.262 |
| 35 | PHE | HE2 | 10.636 | −6.252 | −0.503 |
| 35 | PHE | CZ | 9.770 | −7.402 | −2.104 |
| 35 | PHE | HZ | 8.787 | −6.965 | −2.001 |
| 36 | CYS | N | 13.391 | −7.059 | −5.568 |
| 36 | CYS | CA | 12.937 | −6.919 | −6.979 |
| 36 | CYS | C | 12.642 | −5.431 | −7.337 |
| 36 | CYS | O | 13.077 | −4.984 | −8.423 |
| 36 | CYS | CB | 11.711 | −7.838 | −7.186 |
| 36 | CYS | SG | 11.181 | −7.821 | −8.935 |
| 36 | CYS | OXT | 11.882 | −4.739 | −6.619 |
| 36 | CYS | HN | 13.082 | −6.376 | −4.869 |
| 36 | CYS | HA | 13.741 | −7.243 | −7.669 |
| 36 | CYS | HB1 | 11.954 | −8.878 | −6.906 |
| 36 | CYS | HB2 | 10.872 | −7.519 | −6.542 |
| 36 | CYS | HG | 10.855 | −6.530 | −9.009 |
| END | | | | | |
| 1 | CYS | N | 8.859 | −12.826 | −0.866 |
| 1 | CYS | CA | 7.463 | −12.830 | −1.374 |
| 1 | CYS | HN1 | 9.334 | −13.726 | −0.991 |
| 1 | CYS | HN2 | 9.421 | −12.087 | −1.305 |
| 1 | CYS | HN3 | 8.864 | −12.628 | 0.142 |
| 1 | CYS | HA | 7.468 | −13.235 | −2.407 |
| 1 | CYS | C | 6.828 | −11.396 | −1.494 |
| 1 | CYS | O | 7.522 | −10.392 | −1.317 |
| 1 | CYS | CB | 6.712 | −13.837 | −0.472 |
| 1 | CYS | SG | 6.308 | −13.188 | 1.176 |
| 1 | CYS | HB1 | 5.744 | −14.101 | −0.939 |
| 1 | CYS | HB2 | 7.235 | −14.807 | −0.360 |
| 2 | TYR | N | 5.529 | −11.294 | −1.812 |
| 2 | TYR | CA | 4.750 | −10.029 | −1.672 |
| 2 | TYR | HN | 5.009 | −12.171 | −1.934 |
| 2 | TYR | HA | 5.241 | −9.395 | −0.905 |
| 2 | TYR | C | 3.318 | −10.348 | −1.118 |
| 2 | TYR | O | 2.710 | −11.362 | −1.482 |
| 2 | TYR | CB | 4.792 | −9.194 | −2.987 |
| 2 | TYR | HB1 | 4.452 | −8.169 | −2.757 |
| 2 | TYR | HB2 | 5.851 | −9.037 | −3.272 |
| 2 | TYR | CG | 3.999 | −9.693 | −4.206 |
| 2 | TYR | CD1 | 4.589 | −10.559 | −5.132 |
| 2 | TYR | HD1 | 5.609 | −10.885 | −5.003 |
| 2 | TYR | CD2 | 2.682 | −9.266 | −4.405 |
| 2 | TYR | HD2 | 2.215 | −8.590 | −3.702 |
| 2 | TYR | CE1 | 3.859 | −11.011 | −6.232 |
| 2 | TYR | HE1 | 4.307 | −11.690 | −6.943 |
| 2 | TYR | CE2 | 1.957 | −9.716 | −5.506 |
| 2 | TYR | HE2 | 0.936 | −9.388 | −5.641 |
| 2 | TYR | CZ | 2.547 | −10.590 | −6.416 |
| 2 | TYR | OH | 1.833 | −11.038 | −7.494 |
| 2 | TYR | HH | 0.967 | −10.629 | −7.471 |
| 3 | TYR | N | 2.784 | −9.498 | −0.230 |
| 3 | TRP | CA | 1.456 | −9.732 | 0.411 |
| 3 | TRP | HN | 3.400 | −8.720 | 0.047 |
| 3 | TRP | HA | 1.393 | −10.807 | 0.685 |
| 3 | TRP | C | 0.227 | −9.448 | −0.539 |
| 3 | TRP | O | 0.394 | −9.065 | −1.703 |
| 3 | TRP | CB | 1.498 | −8.898 | 1.727 |
| 3 | TRP | HB1 | 2.506 | −8.943 | 2.193 |
| 3 | TRP | HB2 | 1.353 | −7.829 | 1.491 |
| 3 | TRP | CG | 0.519 | −9.345 | 2.820 |
| 3 | TRP | CD1 | −0.639 | −8.655 | 3.245 |
| 3 | TRP | CD2 | 0.588 | −10.478 | 3.609 |
| 3 | TRP | NE1 | −1.306 | −9.343 | 4.282 |
| 3 | TRP | CE2 | −0.520 | −10.467 | 4.493 |
| 3 | TRP | HD1 | −0.967 | −7.716 | 2.824 |
| 3 | TRP | HE1 | −2.095 | −9.033 | 4.857 |
| 3 | TRP | CE3 | 1.538 | −11.532 | 3.661 |
| 3 | TRP | HE3 | 2.409 | −11.541 | 3.020 |
| 3 | TRP | CZ2 | −0.682 | −11.505 | 5.441 |
| 3 | TRP | HZ2 | −1.510 | −11.494 | 6.133 |
| 3 | TRP | CZ3 | 1.353 | −12.549 | 4.598 |
| 3 | TRP | HZ3 | 2.088 | −13.342 | 4.654 |
| 3 | TRP | CH2 | 0.260 | −12.537 | 5.476 |
| 3 | TRP | HH2 | 0.160 | −13.332 | 6.200 |
| 4 | GLU | N | −1.026 | −9.624 | −0.065 |
| 4 | GLU | CA | −2.251 | −9.398 | −0.900 |
| 4 | GLU | HN | −1.066 | −9.985 | 0.896 |
| 4 | GLU | HA | −2.059 | −9.850 | −1.895 |
| 4 | GLU | C | −2.579 | −7.874 | −1.150 |
| 4 | GLU | O | −3.531 | −7.282 | −0.629 |
| 4 | GLU | CB | −3.423 | −10.225 | −0.289 |

TABLE IV-continued

Orthogonal three dimensional coordinates in Ångströms for the cP226 · phospholamban (1–36) complex

| Residue | Atom | | X | Y | Z |
|---|---|---|---|---|---|
| 4 | GLU | CG | −4.548 | −10.658 | −1.279 |
| 4 | GLU | CD | −5.428 | −9.594 | −1.902 |
| 4 | GLU | OE1 | −5.983 | −8.751 | −1.176 |
| 4 | GLU | OE2 | −5.630 | −9.609 | −3.130 |
| 4 | GLU | HB1 | −3.026 | −11.161 | 0.155 |
| 4 | GLU | HB2 | −3.858 | −9.678 | 0.569 |
| 4 | GLU | HG1 | −4.114 | −11.254 | −2.103 |
| 4 | GLU | HG2 | −5.235 | −11.354 | −0.770 |
| 5 | LEU | N | −1.753 | −7.242 | −1.991 |
| 5 | LEU | CA | −1.972 | −5.882 | −2.541 |
| 5 | LEU | HN | −0.922 | −7.815 | −2.212 |
| 5 | LEU | HA | −3.057 | −5.734 | −2.704 |
| 5 | LEU | C | −1.333 | −5.919 | −3.973 |
| 5 | LEU | O | −1.967 | −6.436 | −4.899 |
| 5 | LEU | CB | −1.517 | −4.805 | −1.497 |
| 5 | LEU | HB1 | −0.421 | −4.840 | −1.373 |
| 5 | LEU | HB2 | −1.897 | −5.131 | −0.508 |
| 5 | LEU | CG | −2.002 | −3.346 | −1.723 |
| 5 | LEU | HG | −3.062 | −3.370 | −2.045 |
| 5 | LEU | CD1 | −1.930 | −2.530 | −0.421 |
| 5 | LEU | HD11 | −2.500 | −2.998 | 0.402 |
| 5 | LEU | HD12 | −0.889 | −2.404 | −0.065 |
| 5 | LEU | HD13 | −2.344 | −1.512 | −0.553 |
| 5 | LEU | CD2 | −1.183 | −2.584 | −2.778 |
| 5 | LEU | HD21 | −1.272 | −3.021 | −3.788 |
| 5 | LEU | HD22 | −1.512 | −1.532 | −2.878 |
| 5 | LEU | HD23 | −0.102 | −2.555 | −2.533 |
| 6 | GLU | N | −0.102 | −5.418 | −4.147 |
| 6 | GLU | CA | 0.670 | −5.433 | −5.427 |
| 6 | GLU | HN | 0.318 | −5.068 | −3.279 |
| 6 | GLU | HA | 0.760 | −6.480 | −5.776 |
| 6 | GLU | C | 2.125 | −4.958 | −5.064 |
| 6 | GLU | O | 3.021 | −5.761 | −4.797 |
| 6 | GLU | CB | −0.062 | −4.615 | −6.547 |
| 6 | GLU | CG | 0.643 | −4.580 | −7.927 |
| 6 | GLU | CD | −0.149 | −3.863 | −8.997 |
| 6 | GLU | OE1 | −0.877 | −4.532 | −9.753 |
| 6 | GLU | OE2 | −0.072 | −2.625 | −9.100 |
| 6 | GLU | HB1 | −1.073 | −5.034 | −6.699 |
| 6 | GLU | HB2 | −0.241 | −3.577 | −6.203 |
| 6 | GLU | HG1 | 1.630 | −4.089 | −7.869 |
| 6 | GLU | HG2 | 0.842 | −5.603 | −8.299 |
| 8 | TRP | N | 2.313 | −3.638 | −4.926 |
| 8 | TRP | CA | 3.537 | −2.986 | −4.364 |
| 8 | TRP | HN | 1.515 | −3.090 | −5.263 |
| 8 | TRP | HA | 4.424 | −3.433 | −4.856 |
| 8 | TRP | C | 3.848 | −3.117 | −2.821 |
| 8 | TRP | O | 4.653 | −2.346 | −2.288 |
| 8 | TRP | CB | 3.456 | −1.496 | −4.839 |
| 8 | TRP | HB1 | 4.309 | −0.929 | −4.424 |
| 8 | TRP | HB2 | 3.659 | −1.485 | −5.927 |
| 8 | TRP | CG | 2.153 | −0.690 | −4.582 |
| 8 | TRP | CD1 | 1.178 | −0.428 | −5.575 |
| 8 | TRP | CD2 | 1.662 | −0.105 | −3.421 |
| 8 | TRP | NE1 | 0.101 | 0.325 | −5.068 |
| 8 | TRP | CE2 | 0.430 | 0.525 | −3.742 |
| 8 | TRP | HD1 | 1.240 | −0.780 | −6.598 |
| 8 | TRP | HE1 | −0.765 | 0.609 | −5.546 |
| 8 | TRP | CE3 | 2.173 | −0.038 | −2.098 |
| 8 | TRP | HE3 | 3.108 | −0.507 | −1.834 |
| 8 | TRP | CZ2 | −0.283 | 1.234 | −2.751 |
| 8 | TRP | HZ2 | −1.204 | 1.736 | −2.998 |
| 8 | TRP | CZ3 | 1.437 | 0.648 | −1.130 |
| 8 | TRP | HZ3 | 1.792 | 0.681 | −0.112 |
| 6 | TRP | CH2 | 0.230 | 1.282 | −1.455 |
| 8 | TRP | HH2 | −0.324 | 1.816 | −0.694 |
| 8 | LEU | N | 3.264 | −4.088 | −2.102 |
| 8 | LEU | CA | 3.536 | −4.329 | −0.654 |
| 8 | LEU | HN | 2.865 | −4.819 | −2.705 |
| 8 | LEU | HA | 3.941 | −3.411 | −0.189 |
| 8 | LEU | C | 4.558 | −5.516 | −0.479 |
| 8 | LEU | O | 4.209 | −6.629 | −0.884 |
| 8 | LEU | CB | 2.165 | −4.593 | 0.042 |
| 8 | LEU | HB1 | 1.4O8 | −3.926 | −0.417 |
| 8 | LEU | HB2 | 1.824 | −5.619 | −0.207 |
| 8 | LEU | CG | 2.061 | −4.358 | 1.574 |
| 8 | LEU | HG | 2.296 | −3.294 | 1.781 |
| 8 | LEU | CD1 | 3.002 | −5.228 | 2.425 |
| 8 | LEU | HD11 | 4.062 | −4.953 | 2.285 |
| 8 | LEU | HD12 | 2.805 | −5.135 | 3.510 |
| 8 | LEU | HD13 | 2.927 | −6.303 | 2.177 |
| 8 | LEU | CD2 | 0.619 | −4.623 | 2.040 |
| 8 | LEU | HD21 | 0.492 | −4.415 | 3.118 |
| 8 | LEU | HD22 | −0.111 | −3.989 | 1.507 |
| 8 | LEU | HD23 | 0.316 | −5.674 | 1.876 |
| 9 | PRO | N | 5.780 | −5.358 | 0.119 |
| 9 | PRO | CA | 6.694 | −6.502 | 0.430 |
| 9 | PRO | CD | 6.411 | −4.035 | 0.314 |
| 9 | PRO | HA | 7.030 | −6.917 | −0.541 |
| 9 | PRO | HD1 | 6.017 | −3.549 | 1.227 |
| 9 | PRO | HD2 | 6.254 | −3.346 | −0.539 |
| 9 | PRO | C | 6.165 | −7.738 | 1.234 |
| 9 | PRO | O | 4.962 | −7.953 | 1.399 |
| 9 | PRO | CB | 7.873 | −5.753 | 1.096 |
| 9 | PRO | HB1 | 8.834 | −6.283 | 0.969 |
| 9 | PRO | HB2 | 7.706 | −5.659 | 2.189 |
| 9 | PRO | CG | 7.892 | −4.373 | 0.455 |
| 9 | PRO | HG1 | 8.381 | −4.416 | −0.539 |
| 9 | PRO | HG2 | 8.450 | −3.636 | 1.059 |
| 10 | CYS | N | 7.083 | −8.610 | 1.703 |
| 10 | CYS | CA | 6.766 | −10.017 | 2.059 |
| 10 | CYS | HN | 8.045 | −8.317 | 1.519 |
| 10 | CYS | HA | 6.123 | −10.428 | 1.255 |
| 10 | CYS | C | 5.908 | −10.281 | 3.352 |
| 10 | CYS | O | 4.684 | −10.146 | 3.295 |
| 10 | CYS | CB | 8.136 | −10.743 | 1.930 |
| 10 | CYS | SG | 7.929 | −12.525 | 2.158 |
| 10 | CYS | HB1 | 8.849 | −10.378 | 2.694 |
| 10 | CYS | HB2 | 8.613 | −10.553 | 0.953 |
| 11 | ALA | N | 6.523 | −10.747 | 4.456 |
| 11 | ALA | CA | 5.941 | −11.825 | 5.306 |
| 11 | ALA | HN | 7.531 | −10.788 | 4.308 |
| 11 | ALA | HA | 6.701 | −12.037 | 6.082 |
| 11 | ALA | C | 5.832 | −13.184 | 4.541 |
| 11 | ALA | O | 6.858 | −13.901 | 4.464 |
| 11 | ALA | OXT | 4.767 | −13.516 | 3.972 |
| 11 | ALA | CB | 4.694 | −11.381 | 6.092 |
| 11 | ALA | HB1 | 3.843 | −11.199 | 5.412 |
| 11 | ALA | HB2 | 4.376 | −12.169 | 6.797 |
| 11 | ALA | HB3 | 4.873 | −10.456 | 6.664 |
| END | | | | | |

TABLE V

| Residue | NH | C$_\alpha$H | C$_\beta$H | C$_\gamma$H | C$_\delta$H | Others |
|---|---|---|---|---|---|---|
| Met1 |  | 4.159 | 2.124 | 2.566 |  | 2.012 |
| Glu2 | 8.803 | 4.572 | 1.967 | 2,510, 2.319 |  |  |
| Lys3 | 8.787 | 4.147 | 1.900 | 1.559, 1.431 | 1.729 | 2.969 |
| Val4 | 8.314 | 3.889 | 2.132 | 1.026, 0.951 |  |  |
| Gln5 | 7.846 | 4.092 | 2.364, 2.252 | 2.369 |  | 7.431, 6.823 |
| Tyr6 | 7.924 | 4.225 | 3.114 |  | 7.046 | 6.780 |
| Leu7 | 8.536 | 4.013 | 1.831 | 1,586 | 0.915 |  |
| Thr8 | 7.975 | 3.955 | 4.247 | 1.222 |  |  |
| Arg9 | 8.156 | 3.518 | 1.845, 1.725 | 1.587 | 3.092 | 7.242 |
| Ser10 | 7.991 | 4.082 | 3.936, 3.767 |  |  |  |
| Ala11 | 8.051 | 4.085 | 1.510 |  |  |  |
| Ile12 | 8.126 | 3.681 | 1.857 | 1.704, 1.014 | 0.769 | 0.860 |
| Arg13 | 8.181 | 3.983 | 1.941, 1.735 | 1.606 | 3.162 | 7.189 |
| Arg14 | 8.143 | 4.052 | 1.941, 1.733 | 1.725, 1.604 | 3.169 | 7.154 |
| Ala15 | 8.422 | 4.114 | 1.500 |  |  |  |
| Ser16 | 8.110 | 4.275 | 4.029, 3.979 |  |  |  |
| Thr17 | 7.695 | 4.316 | 4.373 | 1.270 |  |  |
| Ile18 | 7.589 | 4.102 | 1.925 | 1.576, 1.216 | 0.851 | 0.912 |
| Glu19 | 8.149 | 4.351 | 2.121, 2.011 | 2.468, 2.426 |  |  |
| Met20 | 7.958 | 4.702 | 2.088 | 2.544 |  | 2.027 |
| Pro21 |  | 4.487 | 2.539, 2.483 | 2.082, 1.948 | 3.876, 3.591 |  |
| Gln22 | 8.766 | 4.008 | 2.173 | 2.438 |  | 7.433, 6.742 |
| Gln23 | 8.954 | 4.079 | 2.084, 1.945 | 2.464 |  | 7.457, 6.784 |
| Ala24 | 7.455 | 4.155 | 1.474 |  |  |  |
| Arg25 | 7.858 | 3.944 | 1.876, 1712 | 1.604 | 3.246, 3.181 | 7.253 |
| Gln26 | 8.143 | 4.019 | 2.136, 2.115 | 2.461, 2.374 |  | 7.371, 6.721 |
| Lys27 | 7.647 | 4.069 | 1.954, 1.598 | 1.613, 1.465 | 1.682 | 2.937, 7.604 |
| Leu28 | 8.099 | 4.063 | 1.773, 1.712 | 1.510 | 0.849, 0.818 |  |
| Gln29 | 8.212 | 3.985 | 2.198, 2.117 | 2.480, 2.367 |  | 7.172, 6.668 |
| Asn30 | 7.908 | 4.482 | 2.884, 2.803 |  | 7.486, 6.821 |  |
| Leu31 | 7.878 | 4.154 | 1.718, 1.625 | 1.557 | 0.859, 0.797 |  |
| Phe32 | 8.162 | 4.430 | 3.238, 3.096 |  | 7.173 | 7.197 |
| Ile33 | 7.974 | 3.986 | 1.930 | 1.611, 1.283 | 0.900 | 0.891 |
| Asn34 | 7.801 | 4.570 | 2.588, 2.511 |  | 7.337, 6.759 |  |
| Phe35 | 8.006 | 4.694 | 3.272, 3.058 |  | 7.277 | 7.207 |
| Cys36 | 7.727 | 4.452 | 2.890 |  |  |  |

TABLE VI

NMR assignments of cP226 (SEQ ID NO: 10) in water.

1H-chemical shifts of cP226 (SEQ ID NO: 10) in 90% H$_2$O/10% D$_2$O, pH 6.50 at 10° C.

Values expressed in ppm.

| res. | HN | HA | HB1* | HB2 | HG* | HD1/ HD* | HD2/ HE* | HE3 | HZ2 |
|---|---|---|---|---|---|---|---|---|---|
| Cys 1 |  | 4.054 | 2.991 | 2.896 |  |  |  |  |  |
| Tyr 2 | 6.924 | 4.695 | 2.884 |  |  | 6.986 | 6.792 |  |  |
| Trp 3 | 8.094 | 4.599 | 3.199 | 3.087 |  | 7.106 | 10.024 | 7.427 | 7.465 |
| Glu 4 | 8.313 | 3.907 | 1.909 | 1.785 |  |  |  |  |  |
| Leu 5 | 7.857 | 4.093 | 1.495 | 1.496 | 1.132 | 0.822 |  |  |  |
| Glu 6 | 8.227 | 4.123 | 2.032 | 1.982 | 2.195 | 7.074 |  |  |  |
| Trp 7 | 7.871 | 4.398 | 3.207 |  | 0.790 | 10.188 | 7.449 | 7.458 |  |
| Leu 8 | 7.326 | 4.514 | 1.377 |  | 1.256 |  |  |  |  |
| Pro 9 |  | 4.179 | 2.214 | 1.820 | 1.974 | 3.617 | 3.505 |  |  |
| Cys 10 | 8.457 | 4.505 | 3.128 | 2.906 |  |  |  |  |  |
| Ala 11 | 8.062 | 4.115 | 1.330 |  |  |  |  |  |  |

TABLE VII

Quality of the structure of cP226 (SEQ ID NO: 10) obtained by noe data RMSD values were calculated from a family od 12 structures without NOE restrain violation bigger than 0.3 Å.

The local RMSD was calculated on 3 residues

| res. | Global displacem. | | | local RMSD | Local displacem. | | | NOEs (total) |
|---|---|---|---|---|---|---|---|---|
|  | bb | heavy | heavysc | bb | bb | heavy | heavysc |  |
| Cys 1 | 1.80 | 1.99 | 1.77 | 0.00 | 0.00 | 0.00 | 0.00 | 2 |
| Tyr 2 | 0.92 | 3.52 | 4.23 | 0.72 | 0.59 | 3.21 | 3.86 | 6 |
| Trp 3 | 0.76 | 1.36 | 1.50 | 0.35 | 0.26 | 0.73 | 0.81 | 17 |
| Glu 4 | 0.83 | 2.22 | 2.86 | 0.29 | 0.23 | 1.77 | 2.33 | 12 |
| Leu 5 | 0.63 | 1.38 | 1.78 | 0.26 | 0.20 | 1.04 | 1.44 | 23 |
| Glu 6 | 0.73 | 2.34 | 3.00 | 0.26 | 0.24 | 1.73 | 2.23 | 9 |
| Trp 7 | 0.65 | 2.06 | 2.39 | 0.27 | 0.25 | 1.67 | 1.96 | 16 |
| Leu 8 | 0.53 | 1.55 | 2.11 | 0.18 | 0.16 | 1.58 | 2.22 | 27 |
| Pro 9 | 0.60 | 0.83 | 1.04 | 0.17 | 0.12 | 0.18 | 0.21 | 15 |
| Cys 10 | 0.71 | 0.94 | 1.11 | 0.27 | 0.18 | 0.36 | 0.54 | 13 |
| Ala 11 | 1.20 | 1.67 | 1.73 | 0.00 | 0.00 | 0.00 | 0.00 | 6 |

Abbreviations

PLB, phospholamban; PLB[a.a.1–36], 36 a.a. N-terminal fragment of human phospholamban (SEQ ID NO:9); SR, sarcoplasmic reticulum; SERCA, sarco/endoplasmic reticulum Ca$^{2+}$-ATPase; SERCA_2, cardiac isoform of the sarco/endoplasmic reticulum Ca$^{2+}$-ATPase; CD, circular dichroism; COSY, correlation spectroscopy; TOCSY, total correlation spectroscopy; NOESY, nuclear Overhauser-enhancement spectroscopy; d$_3$-TFE, perdeuterated trifluoroethanol; d$_{10}$-DTT, perdeuterated dithioreitol.

What is claimed is:

1. A cyclic peptide having the structure:

(SEQ ID NO: 8)

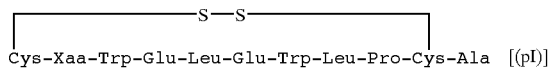

Cys-Xaa-Trp-Glu-Leu-Glu-Trp-Leu-Pro-Cys-Ala  [(pI)]

wherein Xaa is Tyr or Ala.

2. The peptide of claim 1, wherein Xaa is Tyr (SEQ ID NO:10).

3. The cyclic peptide of claim 1, wherein the cyclic peptide is in contact with an aqueous solution.

4. A method of identifying or designing a phospholamban deactivator, comprising the steps of:

(a) obtaining a three dimensional structure of a cyclic peptide (SEQ ID NO: 8)

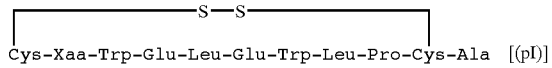

Cys-Xaa-Trp-Glu-Leu-Glu-Trp-Leu-Pro-Cys-Ala  [(pI)]

wherein Xaa is Tyr or Ala;

(b) creating a three dimensional model of a complex of the cyclic peptide bound as a phospholamban deactivator to the phospholamban cytosolic domain of phospholamban or a fragment of the phospholamban cytosolic domain that comprises a ligand binding site;

(c) employing the three dimensional model of the complex to identify the ligand binding site on the phospholamban cytosolic domain or on said fragment of the phospholamban cytosolic domain, wherein the phospholamban deactivator binds to the phospholamban cytosolic domain or to said fragment of the phospholamban cytosolic domain at said ligand binding site;

(d) selecting a candidate molecule that possesses steric and electrostatic complementarity with the ligand binding site and testing same for function as a phospholamban deactivator; and (e) identifying the selected candidate molecule as a phospholamban deactivator.

5. The method of claim 4, wherein step (d) comprises synthesizing and testing the phospholamban deactivator for activation of $Ca^{+2}$-ATPase in the presence of phospholamban.

6. The method of claim 4, wherein step (a) comprises obtaining a first set of atom coordinates defining the three dimensional structure of the cyclic peptide.

7. The method of claim 4, wherein step (b) comprises:

(i) obtaining a first set of atom coordinates defining the three dimensional structure of the cyclic peptide of step (a);

(ii) obtaining a second set of atom coordinates defining the phospholamban cytosolic domain or said fragment of the phospholamban cytosolic domain; and (iii) employing a computer-aided molecular modeling program to combine the first set of atom coordinates with the second set of atom coordinates to create a three dimensional model of a complex of the cyclic peptide bound to phospholamban cytosolic domain or said fragment of the phospholamban cytosolic domain.

8. The method of claim 4, wherein step (c) employs a computer-aided molecular modeling program to identify the ligand binding site on the phospholamban cytosolic domain or said fragment of the phospholamban cytosolic domain.

9. The method of claim 4, wherein step (d) employs a computer-aided molecular modeling program to identify the molecule that interacts with the ligand binding site of the phospholamban cytosolic domain or said fragment of the phospholamban cytosolic domain thereof.

10. The method of claim 4, wherein step (d) comprises:
   (i') providing atom coordinates defining a three-dimensional structure of the phospholamban cytosolic domain or said fragment of the phospholamban cytosolic domain that is in a conformation which allows binding of the phospholamban deactivator;
   (ii') combining the atom coordinates defining the three-dimensional structure of the phospholamban cytosolic domain or said fragment of the phospholamban cytosolic domain of step (i') with a set of atom coordinates defining a three dimensional structure of a candidate molecule;
   (iii') employing a computer-aided molecular modeling program, with the atom coordinates defining the three-dimensional structure of the phospholamban cytosolic domain or said fragment of the phospholamban cytosolic domain and the atom coordinates defining the three dimensional structure of the candidate molecule, to evaluate the ability of the candidate molecule to bind to the ligand binding site of the phospholamban cytosolic domain or said fragment of the phospholamban cytosolic domain; and
   (iv') selecting the candidate molecule that interacts favorably with the ligand binding site of the phospholamban cytosolic domain or said fragment of the phospholamban cytosolic domain, or that possesses steric and electrostatic complementarity with the ligand binding site.

11. The method of claim 10, wherein the atom coordinates defining the three-dimensional structure of the phospholamban cytosolic domain or said fragment of the phospholamban cytosolic domain are obtained from the three dimensional model of the complex created in step (b).

12. The method of claim 10, wherein step (iii') comprises:
   (iiia') performing a fitting operation between the candidate molecule and the ligand binding site of the phospholamban cytosolic domain or said fragment of the phospholamban cytosolic domain; and
   (iiib') analyzing the results of the fitting operation to quantify association between the candidate molecule and the ligand binding site of the phospholamban cytosolic domain or said fragment of the phospholamban cytosolic domain.

13. The method of claim 10, wherein step (iii') comprises:
   (iiia") displaying in a graphical format a protein structure encoded by the combination of the atom coordinates defining the three-dimensional structure of the phospholamban cytosolic domain or said fragment of the phospholamban cytosolic domain and the atom coordinates defining the three dimensional structure of the candidate molecule; and
   (iiib") visually inspecting the protein structure displayed in the graphical format to evaluate the ability of the candidate molecule to bind to the ligand binding site of the phospholamban cytosolic domain or said fragment of the phospholamban cytosolic domain.

14. The method of claim 4, wherein Xaa of the cyclic peptide is Tyr (SEQ ID NO:10).

15. A method of identifying a target area on the surface of phospholamban, at which a phospholamban deactivator binds, the method comprising the steps of:
   (a) obtaining a three dimensional structure of a cyclic peptide (SEQ ID NO: 8)

```
        ┌─────────S─S─────────┐
Cys-Xaa-Trp-Glu-Leu-Glu-Trp-Leu-Pro-Cys-Ala    [(pI)]
``` wherein Xaa is Tyr or Ala;
   (b) creating a three dimensional model of a complex of the cyclic peptide as a phospholamban deactivator bound to phospholamban cytosolic domain or a fragment of the phospholamban cytosolic domain that comprises a ligand binding site; and
   (c) employing a computer-aided molecular modeling program and the three dimensional model of the complex to identify the target area on the surface of phospholamban, wherein said phospholamban deactivator binds to the phospholamban cytosolic domain or to said fragment of the phospholamban cytosolic domain at said ligand binding site.

16. The method of claim 15, wherein Xaa of the cyclic peptide is Tyr (SEQ ID NO:10).

* * * * *

SEQUENCE LISTING

<160> NUMBER OF SEQ ID NOS: 10

<210> SEQ ID NO 1
<211> LENGTH: 52
<212> TYPE: PRT
<213> ORGANISM: Homo sapiens

<400> SEQUENCE: 1

```
Met Glu Lys Val Gln Tyr Leu Thr Arg Ser Ala Ile Arg Arg Ala Ser
  1               5                  10                  15

Thr Ile Glu Met Pro Gln Gln Ala Arg Gln Lys Leu Gln Asn Leu Phe
             20                  25                  30

Ile Asn Phe Cys Leu Ile Leu Ile Cys Leu Leu Leu Ile Cys Ile Ile
         35                  40                  45

Val Met Leu Leu
         50
```

<210> SEQ ID NO 2
<211> LENGTH: 52
<212> TYPE: PRT
<213> ORGANISM: Sus sp.

<400> SEQUENCE: 2

```
Met Asp Lys Val Gln Tyr Leu Thr Arg Ser Ala Ile Arg Arg Ala Ser
  1               5                  10                  15

Thr Ile Glu Met Pro Gln Gln Ala Arg Gln Lys Leu Gln Asn Leu Phe
             20                  25                  30

Ile Asn Phe Cys Leu Ile Leu Ile Cys Leu Leu Leu Ile Cys Ile Ile
         35                  40                  45

Val Met Leu Leu
         50
```

<210> SEQ ID NO 3
<211> LENGTH: 52
<212> TYPE: PRT
<213> ORGANISM: Canis sp.

<400> SEQUENCE: 3

```
Met Asp Lys Val Gln Tyr Leu Thr Arg Ser Ala Ile Arg Arg Ala Ser
  1               5                  10                  15

Thr Ile Glu Met Pro Gln Gln Ala Arg Gln Asn Leu Gln Asn Leu Phe
             20                  25                  30

Ile Asn Phe Cys Leu Ile Leu Ile Cys Leu Leu Leu Ile Cys Ile Ile
         35                  40                  45

Val Met Leu Leu
         50
```

<210> SEQ ID NO 4
<211> LENGTH: 52
<212> TYPE: PRT
<213> ORGANISM: Oryctolagus cuniculus

<400> SEQUENCE: 4

```
Met Glu Lys Val Gln Tyr Leu Thr Arg Ser Ala Ile Arg Arg Ala Ser
  1               5                  10                  15

Thr Ile Glu Met Pro Gln Gln Ala Arg Gln Asn Leu Gln Asn Leu Phe
             20                  25                  30

Ile Asn Phe Cys Leu Ile Leu Ile Cys Leu Leu Leu Ile Cys Ile Ile
```

```
                35              40              45

Val Met Leu Leu
    50

<210> SEQ ID NO 5
<211> LENGTH: 52
<212> TYPE: PRT
<213> ORGANISM: Rattus sp.

<400> SEQUENCE: 5

Met Glu Lys Val Gln Tyr Leu Thr Arg Ser Ala Ile Arg Arg Ala Ser
 1               5                  10                  15

Thr Ile Glu Met Pro Gln Gln Ala Arg Gln Asn Leu Gln Asn Leu Phe
            20                  25                  30

Ile Asn Phe Cys Leu Ile Leu Ile Cys Leu Leu Leu Ile Cys Ile Ile
        35                  40                  45

Val Met Leu Leu
    50

<210> SEQ ID NO 6
<211> LENGTH: 52
<212> TYPE: PRT
<213> ORGANISM: Mus sp.

<400> SEQUENCE: 6

Met Glu Lys Val Gln Tyr Leu Thr Arg Ser Ala Ile Arg Arg Ala Ser
 1               5                  10                  15

Thr Ile Glu Met Pro Gln Gln Ala Arg Gln Asn Leu Gln Asn Leu Phe
            20                  25                  30

Ile Asn Phe Cys Leu Ile Leu Ile Cys Leu Leu Leu Ile Cys Ile Ile
        35                  40                  45

Val Met Leu Leu
    50

<210> SEQ ID NO 7
<211> LENGTH: 52
<212> TYPE: PRT
<213> ORGANISM: Gallus sp.

<400> SEQUENCE: 7

Met Glu Lys Val Gln Tyr Ile Thr Arg Ser Ala Leu Arg Arg Ala Ser
 1               5                  10                  15

Thr Leu Glu Val Asn Pro Gln Ala Arg Gln Arg Leu Gln Glu Leu Phe
            20                  25                  30

Val Asn Phe Cys Leu Ile Leu Ile Cys Leu Leu Leu Ile Cys Ile Ile
        35                  40                  45

Val Met Leu Leu
    50

<210> SEQ ID NO 8
<211> LENGTH: 11
<212> TYPE: PRT
<213> ORGANISM: Artificial Sequence
<220> FEATURE:
<223> OTHER INFORMATION: Description of Artificial Sequence: cyclic
      peptide pI
<221> NAME/KEY: OTHER
<222> LOCATION: 2
<223> OTHER INFORMATION: Xaa is preferably Tyr or Ala

<400> SEQUENCE: 8
```

```
Cys Xaa Trp Glu Leu Glu Trp Leu Pro Cys Ala
 1               5                   10
```

<210> SEQ ID NO 9
<211> LENGTH: 36
<212> TYPE: PRT
<213> ORGANISM: Artificial Sequence
<220> FEATURE:
<223> OTHER INFORMATION: Description of Artificial Sequence: cystolic
      part of phospholambam peptide

<400> SEQUENCE: 9

```
Met Glu Lys Val Gln Tyr Leu Thr Arg Ser Ala Ile Arg Arg Ala Ser
 1               5                  10                  15

Thr Ile Glu Met Pro Gln Gln Ala Arg Gln Lys Leu Gln Asn Leu Phe
            20                  25                  30

Ile Asn Phe Cys
            35
```

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: linear or
      cyclic peptide cP226

<400> SEQUENCE: 10

```
Cys Tyr Trp Glu Leu Glu Trp Leu Pro Cys Ala
 1               5                  10
```